US010604551B2

(12) United States Patent
Alonso-Bedate et al.

(10) Patent No.: US 10,604,551 B2
(45) Date of Patent: Mar. 31, 2020

(54) USE OF AN L3 AND/OR L5 SOURCE AS A VACCINE OR AS A DIAGNOSTIC FOR A PARASITIC DISEASE

(75) Inventors: Carlos Alonso-Bedate, Madrid (ES); Manuel Soto-Alvarez, Madrid (ES); Laura Ramírez García, Madrid (ES)

(73) Assignee: LABORATORIES LETI S.L., Tres Cantos, Madrid (ES)

( * ) Notice: Subject to any disclaimer, the term of this patent is extended or adjusted under 35 U.S.C. 154(b) by 1675 days.

(21) Appl. No.: 13/469,636

(22) Filed: May 11, 2012

(65) Prior Publication Data
US 2012/0263746 A1 Oct. 18, 2012

Related U.S. Application Data

(63) Continuation of application No. PCT/EP2010/067380, filed on Nov. 12, 2010.
(60) Provisional application No. 61/261,020, filed on Nov. 13, 2009.

(30) Foreign Application Priority Data

Nov. 13, 2009 (EP) .................................... 09175929

(51) Int. Cl.
*C07K 14/44* (2006.01)
*A61K 39/00* (2006.01)

(52) U.S. Cl.
CPC .............. *C07K 14/44* (2013.01); *A61K 39/00* (2013.01); *A61K 2039/55561* (2013.01); *Y02A 50/41* (2018.01); *Y02A 50/412* (2018.01); *Y02A 50/58* (2018.01)

(58) Field of Classification Search
None
See application file for complete search history.

(56) References Cited

FOREIGN PATENT DOCUMENTS

EP     2499158 B1     11/2016

OTHER PUBLICATIONS

Ellis (Vaccines, W.B. Saunders Company, Chapter 29, 1988, pp. 568-574).*

(Continued)

*Primary Examiner* — Robert A Zeman
(74) *Attorney, Agent, or Firm* — Polsinelli PC; Christopher M. Cabral

(57) ABSTRACT

The invention relates to composition comprising an L3 and/or an L5 source and optionally an adjuvant for the preparation of a medicine for the treatment or prevention of a parasitic disease and to its diagnostic use of said parasitic disease.

5 Claims, 15 Drawing Sheets
Specification includes a Sequence Listing.

(56) References Cited

OTHER PUBLICATIONS

Boslego et al (Vaccines and Immunotherapy, 1991, Chapter 17).*
Skolnick et al. (Trends in Biotechnology 18: 34-39, 2000).*
Greenspan et al. (Nature Biotechnology 7: 936-937, 1999).*
Iborra et al., "Vaccination with the Leishmania major ribosomal proteins plus CpG oligodeoxynucleotides induces protection against experimental cutaneous leishmaniasis in mice," Microbes and Infection 10 (2008), 1133-1141.
Soto et al., "Multicomponent Chimeric Antigen for Serodiagnosis of Canine Visceral Leishmaniasis," Journal of Clinical Microbiology (1998), 58-63.
Baneth, G., et al., "Canine Leishmaniosis—New Concepts and Insights on an Expanding Zoonosis: Part One," Trends in Parasitology, vol. 24, No. 7, pp. 324-330 (May 29, 2008).
Clayton, Christine, E., New EMBO Member's Review, "Life Without Transcriptional Control? From fly to man and back again," The EMBO Journal, vol. 21, No. 8, pp. 1881-1888 (Apr. 15, 2002).
Ferreira, F., et al., "Allergic Cross-Reactivity: From Gene to the Clinic," Allergy, vol. 59, No. 3, pp. 243-267 (Mar. 2004).
Herwaldt, Barbara L., "Leishmaniasis," The Lancet, vol. 354, pp. 1191-1199 (Oct. 2, 1999).
Ivens, Alasdair C., et al., "The Genome of the Kinetoplastic Parasite, *Leishmania major*," Science, Author manuscript, available in PMC May 26, 2006 published in final edited form as Science, vol. 309(5733) pp. 436-442 (Jul. 15, 2005).
Ramirez, L., et al., "Evaluation of Immune Responses and Analysis of the Effect of Vaccination of the Leishmania Major Recombinant Ribosomal Proteins L3 or L5 in Two Different Murine Models of Cutaneous Leishmaniasis," Vaccine, vol. 31, pp. 1312-1319 (Jan. 10, 2013).
Ramirez, L., et al., "Cross-Protective Effect of a Combined L5 plus L3 Leishmania Major Ribosomal Protein Based Vaccine Combined with a TH1 Adjuvant in Murine Cutaneous and Visceral Leishmaniasis," Parasites & Vectors, vol. 7, No. 3, pp. 1-11 (Jan. 2, 2014).
Quinnell, R. J., et al., "Transmission, Reservoir Hosts and Control of Zoonotic Visceral Leishmaniasis," Parasitology, vol. 136, pp. 1915-1934 (Oct. 16, 2009).
Yao, C., et al., "The Major Surface Protease (MSP or GP63 of *Leishmania* sp. Biosynthesis, Regulation of Expression, and Function," Molecular & Biochemical Parasitology, vol. 132, pp. 1-16 (Jul. 31, 2003).
Darrah, P., et al., "Multifunctional TH1 Cells Define a Correlate of Vaccine-Mediated Protection against Leishmania Major," Nature Medicine, vol. 13, p. 843-850, (Jul. 2007).
Handman, E., "Leishmaniasis: Current Status of Vaccine Development," Clinical Microbiology Reviews, pp. 229-243, (Apr. 2001).
Moutaftsi, M., et al., "A Consensus Epitope Prediction Approach Identifies the Breadth of Murine TCD8+-cell Responses to Vaccinia Virus," Nature Biotechnology, vol. 24, No. 7, pp. 817-819, (Jul. 2006).
Larsen, M., et al.,. "Large-scale Validation of Methods for Cytotoxic T-Lymphocyte Epitope Prediction," BMC Bioinformatics, vol. 8, No. 424, pp. 1-12 (Oct. 31, 2007).
Martins, V., et al., "A Recombinant Chimeric Protein Composed by Human and Mice-Specific CD4+ and CD8+ T Cell Epitopes Protects Against Visceral Leishmaniasis," Parasite Immunology, vol. 39, No. 1, pp. 1-39 (Sep. 2016).

\* cited by examiner

Fig 13

| SEQ ID NO: | Primers | Restriction enzymes |
|---|---|---|
| 57 | Forward 5'- CGGGATCCATGTCTCACTGCAAGTTCGAG-3' | BamHI/EcoRV |
| 58 | Reverse 5'-GCGATATCTCCCTTCTTCGCGGCCTTTGCC-3' | |
| 59 | Forward 5'- GCGATATCGGGATGGCCAAGAAGCACCTCAAG-3' | EcoRV/EcoRI |
| 60 | Reverse 5'-CGGAATTCTCCCTTGCGGGCCCTGCGGG-3' | |
| 61 | Forward 5'- CGGAATTCGGGATGAAGCTCAACATCGCGTAC-3' | EcoRI/EcoRV |
| 62 | Reverse 5'-GCGATATCTCCCTTCTTCTGGAATGCTGCCAC-3' | |
| 63 | Forward 5'-GCGATATCGGGATGTGCACGCTGGCAAATTG-3' | EcoRV((BamHI)KpnI |
| 64 | Reverse 5'-GGGGTACCGGATCCTTACTTGCCGAGGCGCTGC-3' | |

USE OF AN L3 AND/OR L5 SOURCE AS A VACCINE OR AS A DIAGNOSTIC FOR A PARASITIC DISEASE

CROSS-REFERENCE TO RELATED APPLICATIONS

This application is a Continuation of PCT international application Ser. No. PCT/EP2010/067380, filed Nov. 12, 2010, designating the United States, which claims the benefit of European Application No. 090175929.0, filed Nov. 13, 2009, and also claims benefit of U.S. Provisional Application No. 61/261,020, filed Nov. 13, 2009. The entire contents of the aforementioned patent applications are incorporated herein by this reference.

FIELD OF THE INVENTION

The invention relates to an L3 and/or L5 source for the preparation of a medicament or a medicine for the treatment, prevention, and/or diagnostic use of a parasitic disease.

BACKGROUND OF THE INVENTION

Leishmaniasis comprises several diseases caused by intracellular protozoan parasites belonging to the genus *Leishmania* that mainly infect macrophages of a variety of mammals including humans and dogs. Depending largely on the species of the parasite and the immunocompetence state of the human host, the disease spectrum ranges from self-healing cutaneous leishmaniasis (CL) to fatal visceral leishmaniasis (VL) or kala-azar (18). Canine viscerocutaneous leishmaniasis (VCL) caused by *Leishmania infantum* and *L. chagasi* is an important emerging zoonosis found in countries around the Mediterranean basin, in the Middle East and in Latin America (16); being dogs the major reservoir of these parasites playing a central role in the transmission to humans by phebotomine sand flies (44). The outcome of infection is determined by interactions between the host immune system and the different parasite species, yet the pathogenesis of leishmaniasis remains unclear and the knowledge on the mechanisms involved in the immune response to *Leishmania* in humans and dogs is still limited.

Generally, protective immunity is associated with a classical cell mediated immune response that induces macrophage activation by T-cell derived cytokines. On the other hand, non-healing disease is associated with the generation of strong humoral responses (15, 24).

Research for the development of second generation vaccines, based on crude parasite fractions or on defined parasite antigens, was addressed to the identification of different surface or secreted parasite molecules that have been tested as vaccine candidates in several experimental models using diverse adjuvants (1, 17, 20, 43, 45, 46, 49, 50). The screening of expression libraries with sera from infected animals or humans has also enabled the selection of a few antigens as candidate vaccines (reviewed in (9)). Among them, those that elicit primarily a $Th_1$-type immune response in infected mice or human patient cells, irrespective of their cellular location, have been implicated in the generation of protective responses in different animal models (48, 51, 52). On the other hand, some of the isolated antigens are intracellular conserved proteins that predominantly stimulate humoral responses in humans or dogs suffering VL or $Th_2$-mediated humoral responses in experimentally infected mice (3, 33, 35, 37, 39). The inadequate humoral response induced against them in dogs suffering from leishmaniasis is thought to result in immunopathology, mainly due to the adverse effects of immune complexes such as uveitis (13), central nervous system lesions (14) or nephritis (21, 22, 30, 31). It has also been recently shown that the presence of IgG immune complexes in humans with VL correlates to an inability to resolve infections, demonstrating that immune complexes can be detrimental to the infected host (27). In spite of not being considered at first as good vaccine candidates, proteins that induce a high humoral response during the infectious process have been associated with the induction of a protective response. For example, parasite tubulins and the histone H2B were recognized by T-cell clones derived from an immune donor (36). In addition, rK39 causes proliferation and IFN-γ production by T cells from immune mice (23.) It has been also shown that genetic immunization with parasite H2B, H3 and H4 genes induces protection in murine visceral leishmaniasis models (62). Also, immunization of the receptor for activated C kinase (LACK) (29), some parasite cystein proteinases (38, 41) or the parasite nucleosome forming histones (11, 19) administered with $Th_1$-promoting adjuvants generate immune responses that correlate to protection against cutaneous leishmaniasis in murine models.

Among the evolutionary conserved antigens of *Leishmania*, several lines of evidence suggest that ribosomal proteins are immunologically relevant molecules during *Leishmania* infection. In some cases, ribosomal constituents can contribute to the host immune system dysfunction through their capacity to modulate cell activities and cytokine release during infection. Thus, injection of the *L. major* ribosomal protein S3a into BALB/c mice induced the polyclonal expansion of B-cell clones and inhibited T-cell proliferation (10). Also, genetic immunization with a DNA vaccine coding for the putative 60S ribosomal protein L31 exacerbated the disease in mice models by the induction of IL-10 and $Th_2$ cytokines (41, 63). In addition, some parasite ribosomal proteins like the parasite acidic P proteins have been related to the generation of strong humoral responses in dogs and humans suffering leishmaniasis (reviewed in (39)). However, it has also been shown that several ribosomal proteins tested were not able to induce an immunogenic protective response or, the immunogenic protective response obtained was sub-optimal (55, 41).

Despite all the attempts so far, there is still no valuable vaccines against a parasitic disease such as leishmaniasis. Therefore, there is still an important need for such a vaccine.

DESCRIPTION OF THE INVENTION

In this work, we surprisingly show that two *L. major* ribosomal proteins L3 and L5 are antigenic. This means that each of these two proteins was recognized by the sera from individuals affected with leishmaniasis. In addition, in the murine model of cutaneous leishmaniasis, anti-L3 and anti-L5 antibodies of the IgG1 isotype were found. Immunization of both proteins in BALB/c mice, in the presence of CpG-ODN, induced a Th1 response against them. As a result of the vaccination, mice were protected against the development of CL after challenge with *L. major*. We further demonstrate that the *L. major* proteins could also confer protection against *L. braziliensis* infection. We also demonstrate that L3 and L5 ribosomal proteins are highly conserved at least between different *Leishmania* species. Such compositions are very attractive to be used as a pharmaceutical composition preferably as a diagnostic, a vaccine, or a therapeutic application. The invention is further described below.

Use

In a first aspect of the invention, there is provided the use of a source of L3 and/or L5 and optionally an adjuvant for the preparation of a medicine or a medicament for the treatment or prevention of a parasitic disease in a subject.

L3 and L5 proteins are ribosomal proteins. Ribosomal proteins are well conserved cytosolic proteins. Therefore, an L3 and/or L5 source may be prepared from any eukaryotic organism, be it plant or animal, be it from mammals, reptiles, fish, insects, or any other chromosome bearing organism, such as protozoa. Preferably an L3 and/or L5 source is obtained from an organism which is close to the disease, preferably a parasitic disease causing organism in the evolutionary tree. Therefore, of particular interest as a source of an L3 and/or L5 source to be used in the prevention and/or treatment of a parasitic disease are protozoans like Plasmodium and in particular members of the trypanosomatid family, more in particular different species of the trypanosomatical protozoan Leishmania. There are over 20 known species of Leishmania, including species of the subgenus Leishmania, comprising the complex L. major, including L. major, the complex L. donovani, including L. chagasi, L. donovani and L. infantum, the complex L. mexicana, including L. amazonensis and L. mexicana, as well as the subspecies Viannia, comprising the complex L. braziliensis, including L. braziliensis and L. peruviana and the complex L. guyanensis, including L. guyanensis and L. panamensis. Plasmodium species of particular interest are Plasmodium falciparum and Plasmodium vivax. In a preferred embodiment, an L3 and/or L5 source is obtained from a Leishmania species, preferably Leishmania major, Leishmania infantum, Leishmania donovani, Leishmania mexicana, Leishmania chagasi and/or Leishmania braziliensis. More preferably an L3 source is obtained from a Leishmania species, preferably Leishmania major, Leishmania infantum and/or Leishmania Mexicana. More preferably an L5 source is obtained from a Leishmania species, preferably Leishmania major, Leishmania infantum, Leishmania braziliensis and/or Leishmania mexicana. In Example 2, we demonstrated the existence of highly conserved L3 and L5 homologues (identity of at least 90%, see table 1) in at least three distinct Leishmania species. In another preferred embodiment, an L3 and/or L5 source is obtained from a Plasmodium species. The skilled person will understand that a source of L3 and/or L5 may also be prepared by mixing an L3 and/or L5 source from several distinct organisms as identified herein. The use of an L3 and/or L5 source in a vaccine has been demonstrated herein to have attractive immunogenic properties since it has been shown to induce an immune protective response in a treated subject.

The term "an L3 and/or an L5 source" may be replaced by "a source of an L3 and/or of an L5". An L3 and/or an L5 source preferably comprises an L3 and/or an L5 protein, an L3 and/or an L5 derived peptide or protein fragment and/or a nucleic acid encoding an L3 and/or an L5 protein or derived peptide or protein fragment. A preferred L3 protein is represented by SEQ ID NO:1. This preferred L3 protein originates from Leishmania major and is preferably encoded by SEQ ID NO:2. Another preferred L3 protein is represented by SEQ ID NO:48. This preferred L3 protein originates from Leishmania infantum and is preferably encoded by SEQ ID NO:49. Another preferred L3 protein is represented by SEQ ID NO:50. This preferred L3 protein originates from Leishmania mexicana and is preferably encoded by SEQ ID NO:51.

A preferred L5 protein is represented by SEQ ID NO:3. This preferred L5 protein originates from Leishmania major and is preferably encoded by SEQ ID NO:4. Another preferred L5 protein is represented by SEQ ID NO:52. This preferred L5 protein originates from Leishmania infantum and is preferably encoded by SEQ ID NO:53. Another preferred L5 protein is represented by SEQ ID NO:54. This preferred L5 protein originates from Leishmania mexicana and is preferably encoded by SEQ ID NO:55. Another preferred L5 protein is represented by SEQ ID NO:56. This preferred L5 protein originates from Leishmania braziliensis and is preferably encoded by SEQ ID NO:65.

Throughout this application, each time one refers to a specific nucleotide sequence SEQ ID NO (take SEQ ID NO:2 or 4 or 49 or 51 or 53 or 55 or 65 as example), one may replace it by a nucleotide sequence comprising a nucleotide sequence that has at least 60% sequence identity or similarity with SEQ ID NO:2 or 4 or 49 or 51 or 53 or 55 or 65.

Throughout this application, each time one refers to a specific amino acid sequence SEQ ID NO (take SEQ ID NO:1 or 3 or 48 or 50 or 52 or 54 or 56 as example), one may replace it by a polypeptide comprising an amino acid sequence that has at least 60% sequence identity or similarity with amino acid sequence SEQ ID NO:1 or 3 or 48 or 50 or 52 or 54 or 56.

Accordingly, in a preferred embodiment, a L3 source is a polypeptide comprising an amino acid sequence that has at least 60% sequence identity or similarity with amino acid sequence SEQ ID NO:1 or 48 or 50 and/or which is encoded by a nucleotide sequence that has at least 60% identity with SEQ ID NO:2 or 49 or 51.

Accordingly, in a preferred embodiment a L5 source is a polypeptide comprising an amino acid sequence that has at least 60% sequence identity or similarity with amino acid sequence SEQ ID NO:3 or 52 or 54 or 56 and/or which is encoded by a nucleotide sequence that has at least 60% identity with SEQ ID NO:4 or 53 or 55 or 65.

Accordingly, in a preferred embodiment, a L3 source is a nucleic acid comprising a nucleotide sequence that has at least 60% sequence identity or similarity with nucleotide sequence SEQ ID NO:2 or 49 or 51 and/or which is encodes an amino acid sequence that has at least 60% identity with SEQ ID NO:1 or 48 or 50.

Accordingly, in a preferred embodiment a L5 source is a nucleic acid comprising a nucleic acid sequence that has at least 60% sequence identity or similarity with nucleotide sequence SEQ ID NO:4 or 53 or 55 or 65 and/or which encodes an amino acid sequence that has at least 60% identity with SEQ ID NO:3 or 52 or 54 or 56.

Preferably, said amino acid sequence or nucleotide sequence having at least 60% identity or similarity with a specific identified amino acid or nucleotide sequence are encompassed by the present invention and are said to be functional when the encoded protein or polypeptide, protein fragment, peptide is still capable of eliciting at least the immune response obtainable by SEQ ID NO:1 or 3 or 48 or 50 or 52 or 54 or 56 to at least some extent. To at least some extent preferably means that at least 50%, at least 60%, 70%, 80%, at least 90% or 100%. Eliciting an immune response is later defined herein: a compound is functional when it is able to elicit an immune response in a treated subject which preferably means that it is able to promote or trigger a $Th_1$ immune response against a given antigen L3 and/or L5 and/or that it is able to prevent and/or delay the development of a dermal or mucosal lesion and/or induces a significant reduction of the parasite load in a dermal and/or mucosal lesion and/or in an ear and/or in a draining lymph node (DLN) which preferably drains any of these infected regions (dermal, mucosal region, ear), as well as in an internal organ such as liver, spleen, bone marrow, kidney, brain, etc. An amino acid sequence encompassed by the present invention may comprise one, two, three, four, five or more substitutions and/or insertions and/or deletions and/or additional N- or C-terminal amino acids or chemical moieties to increase stability, solubility and immunogenicity.

An L3 and/or L5 protein fragment or an L3 and/or L5 derived peptide as defined herein is preferably a fragment comprising at least 2, 3, 4, 5, 6, 7, 8, 9, 10, 11, 12, 13, 14, 15, 16, 17, 18, 19, 20, 21, 22, 23, 24, 25, 26, 27, 28, 29, 30 or more contiguous amino acids of a corresponding L3 and/or L5 protein and which is able to elicit an immune response as earlier defined herein. In a preferred embodiment, therefore, an L3 and/or L5 protein fragment or an L3 and/or L5 derived peptide as defined herein is preferably a fragment comprising at least 2, 3, 4, 5, 6, 7, 8, 9, 10, 11, 12, 13, 14, 15, 16, 17, 18, 19, 20, 21, 22, 23, 24, 25, 26, 27, 28, 29, 30 or more contiguous amino acids of SEQ ID NO:1 or 3 or 48 or 50 or 52 or 54 or 56.

As a preferred embodiment, a preferred L3 protein fragment or a preferred L3-derived peptide, comprises or consists of the last 40, 39, 38, 37, 36, 35, 34, 33, 32, 31, 30, 29, 28, 27, 26, 25, 24, 23, 22, 21, 20 contiguous amino acids of the C-terminal part of an L3 protein. Even more preferably, it comprises or consists of the last 40, 39, 38, 37, 36, 35, 34, 33, 32, 31, 30, 29, 28, 27, 26, 25, 24, 23, 22, 21, 20 contiguous amino acids of SEQ ID NO:1 or 48 or 50. Even more preferably, it comprises or consists of amino acid 394-419 of SEQ ID NO:1. As another preferred embodiment, a preferred L5 protein fragment or a preferred L5-derived peptide, comprises or consists of the first 40, 39, 38, 37, 36, 35, 34, 33, 32, 31, 30, 29, 28, 27, 26, 25, 24, 23, 22, 21, 20 contiguous amino acids of the N-terminal part of an L5 protein. Even more preferably, it comprises or consists of the first 40, 39, 38, 37, 36, 35, 34, 33, 32, 31, 30, 29, 28, 27, 26, 25, 24, 23, 22, 21, 20 contiguous amino acids of SEQ ID NO:3 or 52 or 54 or 56. Even more preferably, it comprises or consists of amino acid 1-23 of SEQ ID NO:3. As another preferred embodiment, a preferred L5 protein fragment or a preferred L5-derived peptide, comprises or consists of the last 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6 contiguous amino acids of the C-terminal part of an L5 protein. Even more preferably, it comprises or consists of the last 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6 contiguous amino acids of SEQ ID NO:3 or 52 or 54 or 56. Even more preferably, it comprises or consists of amino acid 322-328 of SEQ ID NO:3. In another preferred embodiment, an L3 and L5 source comprises a protein comprising at least one protein fragment of an L3 protein and at least one protein fragment of an L5 protein. More preferably, an L3 protein fragment and an L5 protein fragment had been fused together to form a chimeric protein. Accordingly, the invention also encompass a nucleic acid or a nucleic acid encoding such an L3 and L5 source.

In a preferred embodiment, an L3 and/or an L5 source comprises at least one L3 and/or L5 protein and/or at least one protein fragment of L3 and/or L5. In a more preferred embodiment, a source of L3 and/or L5 comprises at least two L3 and/or L5 proteins and/or at least two protein fragments of L3 and/or L5. This embodiment relates to a protein-based source, preferably a protein-based vaccine.

It is to be mentioned that in a preferred embodiment a L3 and/or a L5 source as identified herein could not be understood to encompass a Ribosomal Protein Extract (RPE) as identified in WO 2009/090175. A RPE is obtainable by carrying out the following steps using a parasite cell causing a parasitic disease when present in a subject:
  a. mixing a parasite cell with a lysis buffer,
  b. centrifuging the obtained mixture to obtain a cytosolic extract,
  c. preparing a RPE from the obtained cytosolic extract.

Therefore in a preferred embodiment, a L3 and/or a L5 source is not a RPE as defined above.

In another preferred embodiment, an L3 and/or an L5 source comprises at least one nucleic acid encoding L3 and/or L5 and/or at least one nucleic acid encoding a protein fragment of L3 and/or L5. In a more preferred embodiment, a source of L3 and/or L5 comprises at least two nucleic acids encoding an L3 and/or L5 protein and/or at least two nucleic acid encoding protein fragments of L3 and/or L5. This embodiment relates to a nucleic acid-based source, preferably a nucleic acid-based vaccine.

The source of L3 and/or L5 may be a protein, a digest of the protein and/or a fragment thereof, which may be in a purified form or may be comprised within a crude composition, preferably of biological origin, such as a bacterial lysate, yeast lysate, fungal lysate, sonicate or fixate. Alternatively, an L3 and/or L5 source may be chemically synthesized or enzymatically produced in vitro. The source of an L3 and/or L5 protein, or fragment thereof, may also be a nucleic acid encoding said, or fragment thereof, from an RNA or DNA template. The RNA or DNA molecules may be 'naked' DNA, preferably comprised in vesicles or liposomes, or they may be comprised in a vector. The vector may be any (recombinant) DNA or RNA vector known in the art, and preferably is a plasmid; wherein genes encoding latency antigens are operably linked to regulatory sequences conferring expression and translation of the encoded messengers. The vector may also be any DNA or RNA virus, such as, but not limited to, Adenovirus, Adeno-Associated Virus (AAV), a retrovirus, a lentivirus, modified Vaccinia Ankara virus (MVA) or Fowl Pox virus, or any other viral vector capable of conferring expression of polypeptides into a chosen subject. DNA vectors may be non-integrating, such as episomally replicating vectors, or may be vectors integrating in the host genome by random integration or by homologous recombination.

DNA molecules comprising genes encoding an L3 and/or an L5 protein, or fragments thereof according to the current invention, optionally embedded in a vector such as a virus or plasmid, may be integrated in a genome of a subject. In a preferred embodiment of the invention, such a host may be a micro-organism. Preferably such a recombinant micro-organism is a *Mycobacterium*, for instance of the species *M. tuberculosis M. smegmatis* (Yue. Y. et al, (2007), J. Virol. Meth., 141: 41-48, Cayabiyab Y. et al, (2006), J. Virol., 80: 1645-1652) or *M. bovis* and most preferably *M. bovis* Bacillus Calmette Guerin (BCG) or *M. smegmatis*, capable of delivering to a host the polypeptides or fragments thereof according to the invention. Recombinant BCG and methods for recombination are known in the art; for instance, in WO2004094469. Such a recombinant micro-organism may be formulated as a live recombinant and/or live attenuated vaccine, as for instance in Jacobs et al. 1987, Nature, 327(6122):532-5). The vector may also be comprised in a host of bacterial origin, such as, but not limited to, live-attenuated and/or recombinant *Shigella* or *Salmonella* bacteria.

Any known adjuvant may be used in the present invention. The skilled person knows several suitable adjuvants. Adjuvants are most preferably selected from the following list of adjuvants: cationic (antimicrobial) peptides, saponine and Toll-like receptor (TLR) ligands such as, but not limited to, poly(I:C), CpG motifs, LPS, lipid A, lipopeptide Pam3Cys and bacterial flagellins or parts thereof, and their derivatives having chemical modifications. Other preferred adjuvants for use in the method and in compositions according to the invention are: mixtures with live or killed BCG, immunoglobulin complexes with the said latency antigens or parts thereof, IC31 (from www.intercell.com; in WO03047602), QS21/MPL (US2003095974), DDA/MPL (WO2005004911), DA/TDB (WO2005004911; Holten-Andersen et al, 2004 Infect Immun. 2004 March; 72(3):1608-17.) and soluble LAG3 (CD223) (from www.Immunotep.com; US2002192195) In addition, another preferred adjuvant includes the use of *Corynebacterium paryum* or *Propionobacterium acnes* (64, 65, 66).

Particularly preferred adjuvants are those that are known to act via the Toll-like receptors. Adjuvants that are capable of activation of the innate immune system, can be activated particularly well via Toll like receptors (TLR's), including TLR's 1-10 and/or via a RIG-1 (Retinoic acid-inducible gene-1) protein and/or via an endothelin receptor. Compounds capable of activating TLR receptors, and modifications and derivatives thereof, are well documented in the art. TLR1 may be activated by bacterial lipoproteins and acetylated forms thereof, TLR2 may in addition be activated by Gram positive bacterial glycolipids, LPS, LPA, LTA, fimbriae, outer membrane proteins, heatshock proteins from bacteria or from the host, and Mycobacterial lipoarabinomannans. TLR3 may be activated by dsRNA, in particular of viral origin, or by the chemical compound poly(I:C). TLR4 may be activated by Gram negative LPS, LTA, Heat shock proteins from the host or from bacterial origin, viral coat or envelope proteins, taxol or derivatives thereof, hyaluronan containing oligosaccharides and fibronectins. TLR5 may be activated with bacterial flagellae or flagellin. TLR6 may be activated by mycobacterial lipoproteins and group B Streptococcus heat labile soluble factor (GBS-F) or *Staphylococcus modulins*. TLR7 may be activated by imidazoquinolines and derivatives. TLR9 may be activated by unmethylated CpG DNA or chromatin—IgG complexes. In particular TLR3, TLR4, TLR7 and TLR9 play an important role in mediating an innate immune response against viral infections, and compounds capable of activating these receptors are particularly preferred for use in the invention. Particularly preferred adjuvants comprise, but are not limited to, synthetically produced compounds comprising dsRNA, poly (I:C), unmethylated CpG DNA which trigger TLR3 and TLR9 receptors, IC31, a TLR9 agonist, IMSAVAC, a TLR4 agonist. In another preferred embodiment, the adjuvants are physically linked to an L3 and/or L5 source as earlied defined herein. Physical linkage of adjuvants and costimulatory compounds or functional groups, to the HLA class I and HLA class II epitope comprising peptides provides an enhanced immune response by simultaneous stimulation of antigen presenting cells, in particular dendritic cells, that internalize, metabolize and display antigen. Another preferred immune modifying compound is a T cell adhesion inhibitor, more preferably an inhibitor of an endothelin receptor such as BQ-788 (67). BQ-788 is N-cis-2,6-dimethylpiperidinocarbonyl-L-gamma-methylleucyl-D-1-methoxycarbonyltryptophanyl-D-norleucine. However any derivative of BQ-788 or modified BQ-788 compound is also encompassed within the scope of this invention.

Other adjuvants include MPL-SE (Glaxo Smithkline Biologicals, Belgium) or EM005 (IDRI America).

In a preferred embodiment, an adjuvant is a $Th_1$-promoting adjuvant (like an adjuvant comprising a CpG ODN motif). A Th1-promoting adjuvant has been defined in the literature (68) as an adjuvant which is able to promote or trigger a $Th_1$ immune response against a given antigen when used together with this antigen (here an L3 and/or an L5 source) as detected by measurements of splenocytes of a treated subject when cultured with the antigen. As control, the promotion or triggering of a Th1 immune response is assessed in a splenocyte population of the same subject which has not been treated with the antigen and the adjuvant, or with same population only treated with the antigen. Triggering or promoting a $Th_1$ immune response is preferably defined by the induction of IFNγ as detected by culturing splenocytes of a treated subject with the antigen and/or by inducing the production of antigen specific IgG2a immunoglobulines. The assessment of the induction of this cytokine is preferably carried out by ELISA on splenocytes as described in the example. The assessment of the induction of IgG2a is preferably carried out by ELISA or Western Blot as described in example 1. The induction of IFNγ and/or IgG2a upon stimulation of splenocytes with an L3 and/or L5 source and an adjuvant preferably means that the adjuvant is qualified as a Th1-promoting adjuvant.

Alternatively or in combination with the first definition of triggering or promoting a $Th_1$ immune response given above, triggering or promoting a $Th_1$ immune response may further be defined by the absence (or the absence of an induction) of a $Th_2$ immune response. A $Th_2$ immune response is characterised by a detectable increase in IL-4, IL-10 induction and/or the production of detectable IgG1 immunoglobulines when compared with non-treated splenocytes. The assessment of the induction of IL-4 and/or IL-10 is preferably carried out by ELISA on splenocytes as described in the example. The assessment of the induction of an IgG1 is preferably carried out by ELISA or Western Blot as described in example 1.

Alternatively or in combination with the two first definitions of triggering or promoting a $Th_1$ immune response given above, triggering or promoting a $Th_1$ immune response may further be defined by the generation of an increase in IFNγ/IL-10 ratio and/or IFNγ/IL-4 ratio and/or a decrease in IgG1/IgG2a ratio against a defined antigen, in that case a source of L3 and/or L5. In a preferred embodiment, a change (increase or decrease as indicated above) in any of these ratios of more than 2 indicates that an adjuvant has Th1 properties. The assessment of the induction of each of the mentioned cytokines is preferably carried out by ELISA on splenocytes as described in the example. The assessment of the induction of an immunoglobuline IgG1 or IgG2a is preferably carried out by ELISA or Western Blot as described in example 1.

In a preferred embodiment, a Th-1 promoting adjuvant is, or comprises, or consists of, an oligodeoxynucleotide. More preferably, an oligodeoxynucleotide (ODN) comprises, or consists of, CpG in which the C is non-methylated (CpG ODN): 3'purine-CpG-5'pyrimidine. A preferred oligodeoxynucleotide is, or comprises, or consists of, a phosphorothioate-modified ODN sequence. The use of oligodeoxynucleotides having such modification is advantageous since the oligodeoxynucleotides hence used are more stable than non modified oligonucleotides and hence will not easily be degraded once they are in the blood stream. A preferred Th-1 promoting adjuvant consists of, or comprises, at least one CpG motif, at least two, or at least three. Preferred sequences of the immunostimulatory ODN (5' to 3') were TCAACGTTGA (SEQ ID NO:5) and GCTAGCGT-TAGCGT (SEQ ID NO:6). The skilled person is not limited to the sequences explicitly described herein. He/she may design other sequences and subsequently test them for their Th-1 promoting property as defined earlier herein. This preferred identified adjuvant CpG ODN is highly attractive since it was demonstrated in the example that the co-inoculation of LRPE with this Th1-promoting adjuvant induces protection against a challenge with *L. major* parasites in both BALB/c and C57BL/6 mouse strains. In both models, protection correlates to a specific production of IFN-γ. In BALB/c, a restriction in the production of IL-4 and IL-10 was also detected.

The invention provides a use of an L3 and/or L5 source suitable as a 1) preventive (prophylactic), 2) post-exposure/infection or 3) therapeutic/curative vaccine. One advantage of the present invention is that it allows for the preparation of a medical preparation for the treatment of a broader spectrum of parasitic diseases i.e. a medical preparation with cross-species specificity. In many parasitic diseases, a vaccine raised against a specific species, only works against that specific species. One example of a parasitic disease in which this is the case is leishmaniasis. At the moment, the disease is controlled by drugs, but drug treatment does not prevent the spread of the disease and in many cases is not very effective. In a preferred embodiment, a parasitic disease is leishmaniasis or malaria. More preferably, a parasitic disease is caused by a *Leishmania* or by a *Plasmodium* species. In a further preferred embodiment, a parasitic disease is caused by a different species than the species from which an L3 and/or an L5 source is derived. In particular, leishmaniasis caused by one species from the genus *Leishmania* may be treated by using a composition based on an L3 and/or an L5 source from another *Leishmania* species since as demonstrated in the experimental part (see example 2) L3 and L5 homologues from several *Leishmania* species are highly conserved (at least 90% identity, see table 1). In addition, we already demonstrated in the experimental part (see examples 1 and 3) that *Leishmania major* L3 and L5 proteins are able to protect against an *Leishmania major* or *Leishmania braziliensis* infection. In one embodiment, leishmaniasis caused by *L. major* is successfully treated with a composition comprising an L3 and/or an L5 source from *L. infantum, L. chagasi, L. amazonensis* or *L. braziliensis*. In another embodiment, leishmaniasis caused by *L. chagasi* or *L. amazonensis* is successfully treated with a composition comprising an L3 and/or an L5 source from *L. infantum*. In another embodiment, leishmaniasis caused by *L. major* or *L. braziliensis* is successfully treated with a composition comprising an L3 and/or an L5 source from *L. major*. Alternatively, other parasitic diseases, such as malaria, may be successfully treated with a composition based on an L3 and/or an L5 source of another species, for instance based on an L3 and/or an L5 source of *L. infantum* or *L. major* or *L. mexicana* or *L. braziliensis*.

In the context of the invention, a subject means a human or an animal. An animal which is encompassed within the scope of the invention includes a mammal, preferably a dog.

In a preferred embodiment, a medicine (or medical preparation or pharmaceutical composition or medicament) as defined herein is used to increase the ability of a human or animal immune system to fight against an infection and/or a disease, more preferably a parasitic infection and/or a parasitic disease. In particular, it may be used for administration to a human or animal subject. A medicine as defined herein is preferably administered parenterally, e.g. by injection or infusion by intravenous, subcutaneous, intraperitoneal, intramuscular, intraarterial or intralesional route. A preferred administration mode is subcutaneous. The invention is not limited to a specific mode of administration of an L3 and/or L5 source. A preferred mode of administration is oral administration using a capsule or a tablet. Alternatively an L3 and/or an L5 source may be locally administered via a catheter or a pump, or a suppository. Alternatively, an L3 and/or L5 source may be topically administered. The formulation of an L3 and/or L5 source or of a composition comprising an L3 and/or L5 source depends on the intended mode of administration and (therapeutic) application. A pharmaceutical carrier can be any compatible, non toxic substance suitable to deliver an L3 and/or L5 source to a subject. E.g. sterile water, or inert solids or excipients may be used as the carrier, usually complemented with pharmaceutically acceptable adjuvants, buffering agents, dispersing agents, and the like. Compositions will either be in liquid, e.g. a stabilized suspension of an L3 and/or L5 source, or a composition comprising an L3 and/or an L5 source, or in solid and/or dry forms: e.g. powder. For oral and rectal administration, an L3 and/or an L5 source can be administered in solid dosage forms, such as capsules, tablets, suppositories, and powders, or in liquid dosage forms, such as elixirs, syrups, cream, ointment and suspensions. Another form may be a semi-solid or semi-liquid form wherein an L3 and/or L5 is present as a liquid form in or on a solid support such as a patch.

A medicine may be combined with a pharmaceutically acceptable medium or delivery vehicle by conventional techniques known in the art. For example, an L3 and/or an L5 source and optionally an adjuvant may be dissolved in Phosphate buffer saline (PBS). Methods for preparing parenterally administrable compositions are well known in the art and described in more details in various sources, including, for example, Remington's Pharmaceutical Sciences, Ed. AR Gennaro, 20th edition, 2000, Williams & Wilkins, Pa., USA. A medicine is preferably administered in a therapeutically effective dose, i.e. one that will increase the ability of the human or animal immune system to fight an infection and/or a disease as defined herein. Preferably, a therapeutically effective dose of a medical preparation of the invention is able to elicit an immune response as defined herein: a dose is therapeutically effective when it is able to elicit an immune response in a treated subject which preferably means that it is able to promote or trigger a $Th_1$ immune response against a given antigen L3 and/or L5 and/or that it is able to prevent and/or delay the development of a dermal or mucosal lesion and/or induces a significant reduction of the parasite load in a dermal and/or mucosal lesion and/or in an ear and/or in a draining lymph node (DLN) which preferably draines any of these infected regions (dermal, mucosal region, ear), as well as in an internal organ such as liver, spleen, bone marrow, kidney, brain, etc. The assessment of the presence of a dermal lesion is described in example 1 (see FIG. 4: footpad swelling). The assessment of a parasite load is described in the example (see FIG. 4). A therapeutically effective dose of a medicine of the invention will preferably prevent the development of a dermal lesion and/or will preferably induces a parasite load reduction in an ear of approximately 3 orders of magnitude and/or of approximately a similar magnitude in a DLN after a time period comprising first one vaccination using a composition of the invention followed by one sequential infection with a parasite and a waiting time of approximately 6 weeks. In a preferred embodiment, a medicine as defined herein is a vaccine. In a more preferred embodiment, at least 12 μg of an L3 and/or an L5 source is being used in a vaccine. The amount of an L3 and/or an L5 source used refers to the total amount of L3 and L5 used. In an even more preferred embodiment, at least 12-20 μg of an L3 and/or an L5 source must be used to provide an immune response optionally in combination with at least 50 µg of an adjuvant, preferably a Th$_1$-promoting adjuvant such as for example, CpG ODN. A vaccine as defined herein may be a prophylactic or a therapeutic vaccine. The volume in which an L3 and/or an L5 source and optionally an adjuvant, preferably a Th1 promoting adjuvant may be dissolved may vary from 100-500 microliters.

Composition

In a further aspect, there is provided a composition comprising an L3 and/or an L5 source and optionally an adjuvant, preferably a Th$_1$-promoting adjuvant. An L3 and/or an L5 source and an adjuvant have already been defined herein. In a preferred embodiment, a composition consists of an L3 and/or an L5 source and a Th$_1$-promoting adjuvant. A preferred Th$_1$-promoting adjuvant is a CpG ODN. A preferred composition comprises or consists of an L3 and/or an L5 source and optionally an adjuvant, preferably a Th$_1$-promoting adjuvant dissolved in PBS. In a further preferred embodiment, it is also encompassed by the present invention that an L3 and/or an L5 source and an adjuvant, preferably a Th1-promoting adjuvant are sequentially administered. Therefore, both components do not need to be physically present in one single composition as long as they are both administered to a subject.

Such composition may further comprise a pharmaceutically acceptable adjuvant and/or carrier.

Such composition is preferably for use as a medicine. The medicine is preferably a vaccine. Medicine, adjuvant and vaccine have already been extensively defined herein. A composition may be in the liquid, solid or semi-liquid or semi-solid form as already defined herein.

In a preferred embodiment, other compounds are used sequentially or simultaneously with an L3 and/or an L5 source in order to improve the specificity of the therapeutic or prophylactic treatment. It is advantageous for example to use other compounds that will further enhance the immune response of the treated subject. More preferably, such compounds are not present in a single composition together with an L3 and/or an L5 source. For example said compounds are selected from a group consisting of a source of other proteins from a parasite causing a parasitic disease (19) such as Leishmaniasis. A source of a given protein is given the same meaning as a source of an L3 and/or an L5 as defined earlier herein. A preferred protein is in this context a histone such as a H2A, H2B, H3, H4, another ribosomal protein such as Li2A (LiP), LiP2b (LiP'), LiP0, L2, L7, L8, L16, S6, L19 and S4.

A preferred H2A protein is represented by SEQ ID NO:7. A preferred nucleic acid encoding a H2A is represented by SEQ ID NO:8. A preferred H2B protein is represented by SEQ ID NO:9. A preferred nucleic acid encoding a H2B is represented by SEQ ID NO:10. A preferred H3 protein is represented by SEQ ID NO:11. A preferred nucleic acid encoding a H3 is represented by SEQ ID NO:12. A preferred H4 protein is represented by SEQ ID NO:13. A preferred nucleic acid encoding a H4 is represented by SEQ ID NO:14. A preferred Li2A also named LiP2a protein is represented by SEQ ID NO:15 or 16. A preferred nucleic acid encoding a Li2A is represented by SEQ ID NO:17. SEQ ID NO: 17 is a genomic sequence. The skilled person could derive preferred coding sequences from this genomic sequence. Such preferred coding sequences correspond to a nucleic acid encoding a mRNA coding for a Li2A protein represented by SEQ ID NO: 15 or 16: one from nucleotide 791 to 1111 and one from 1662 to 1982 of SEQ ID NO:17.

A preferred LiP2b protein is represented by SEQ ID NO:18. A preferred nucleic acid encoding a LiP2b is represented by SEQ ID NO:19. A preferred LiP0 protein is represented by SEQ ID NO:20. A preferred nucleic acid encoding a LiP0 is represented by SEQ ID NO:21.

SEQ ID NO: 8, 10, 12, 14, 19 and 21 are genomic sequences. The skilled person could derive other preferred coding sequences from these genomic sequences. Such other preferred coding sequences correspond to a nucleic acid encoding a mRNA coding for the respective protein: These nucleic acid sequences are represented by SEQ ID NO: 68, 69, 70, 71, 72 and 73 respectively.

A preferred L2 protein is represented by SEQ ID NO:22. A preferred nucleic acid encoding L2 is represented by SEQ ID NO:23. A preferred L7 protein is represented by SEQ ID NO:24. A preferred nucleic acid encoding a L7 is represented by SEQ ID NO:25. A preferred L8 protein is represented by SEQ ID NO:26. A preferred nucleic acid encoding a L8 is represented by SEQ ID NO:27. A preferred L16 protein is represented by SEQ ID NO:28. A preferred nucleic acid encoding a L16 is represented by SEQ ID NO:29. A preferred L19 protein is represented by SEQ ID NO:30. A preferred nucleic acid encoding a L19 is represented by SEQ ID NO:31. A preferred S4 protein is represented by SEQ ID NO:32. A preferred nucleic acid encoding a S4 is represented by SEQ ID NO:33. A preferred S6 protein is represented by SEQ ID NO:34. A preferred nucleic acid encoding a S6 is represented by SEQ ID NO:35. Another example is the use of poly-proteins containing several parasite antigens (63, 65). An example of a poly-protein is protein Q as identified in EP 1 141 305. A nucleic acid molecule encoding protein Q is represented by SEQ ID NO:36 A corresponding encoded protein Q is represented by SEQ ID NO: 37. Protein Q or a part or a fragment thereof or a source of protein Q or a source of a fragment of protein Q may be used in combination with a source of L3 and/or L5. Another example of a poly-protein is Leish-110f (69). Leish-110f or a part or a fragment thereof or a source of Leish-110f or a source of a fragment of Leish-110f may be used in combination with a source of L3 and/or L5.

In coming paragraph, a source of an histone protein is taken as an example of a protein that can be used in combination a source of an L3 and/or L5 protein. The same holds for other proteins defined above, preferably other ribosomal proteins than L3 and/or L5. Preferred compounds include a histone protein or fragment thereof, or a nucleic acid molecule encoding said histone or said histone fragment. More preferably, a histone protein is H2A, H2B, H3 and/or H4 as identified in EP 1 687 023. Histones H2A, H2B, H3 and H4 are well-conserved nuclear proteins and their sequence is well-known in the art, see reference 39. Preferably the histones are obtained from an organism which is close to the disease causing organism in the evolutionary tree.

Therefore, of particular interest as a source of histones to be used in the treatment of parasitic diseases such as leishmaniasis are protozoans and in particular members of the trypanosomatid family, more in particular different species of the trypanosomatical protozoan *Leishmania*.

Other preferred compounds include other ribosomal protein or fragment thereof or a nucleic acid molecule encoding said protein or fragment thereof. Examples of other ribosomal protein include L19 and S4.

Other preferred compounds include a Ribosomal Protein Extract as identified in WO 2009/090175.

Each of the compounds or sources of each of these compounds may be used in combination with a source of an L3 and/or an L5 source. The combined use may be sequential or simultaneous.

In a preferred embodiment, a L3 and/or a L5 source is used in combination with a S4 and/or a S6 source. More preferably a L3, a L5, a S4 and a S6 source are used in combination. In another more preferred embodiment, a L3, a L5 and a S4 source are used in combination. In another more preferred embodiment, a L3, a L5 and a S6 source are used in combination. We demonstrated (see example 5) that the combined use of L3, L5 and S4 was providing synergistic protection compared to the use of L3 or L5 or S4 alone. In this context, a preferred S4 protein is represented by SEQ ID NO:32. A preferred nucleic acid encoding a S4 is represented by SEQ ID NO:33. A preferred S6 protein is represented by SEQ ID NO:34. A preferred nucleic acid encoding a S6 is represented by SEQ ID NO:35. The term "source" when used in "a S4 and/or a S6 source" has the same meaning as the term "source" when used in "a L3 and/or a L5 source".

Accordingly, in a preferred embodiment, a S4 source is a polypeptide comprising an amino acid sequence that has at least 60% sequence identity or similarity with amino acid sequence SEQ ID NO:32 and/or which is encoded by a nucleotide sequence that has at least 60% identity with SEQ ID NO:33.

Accordingly, in a preferred embodiment a S6 source is a polypeptide comprising an amino acid sequence that has at least 60% sequence identity or similarity with amino acid sequence SEQ ID NO:34 and/or which is encoded by a nucleotide sequence that has at least 60% identity with SEQ ID NO:35.

Accordingly, in a preferred embodiment, a S4 source is a nucleic acid comprising a nucleotide sequence that has at least 60% sequence identity or similarity with nucleotide sequence SEQ ID NO:33 and/or which is encodes an amino acid sequence that has at least 60% identity with SEQ ID NO:32.

Depending on the type of source used (protein-based or nucleic acid-based), the skilled person will know which type of formulation is suited. A source may be administered as such (naked protein or nucleic-acid). Alternatively, a nucleic acid-based source may be administrated using a nucleic acid construct as defined herein.

S6 Source

In a further aspect there is provided a S6 source or a composition comprising or consisting of a S6 source but not comprising a L3 and/or a L5 and/or a S4 source. We demonstrated (see example 4) that the use of S6 alone was providing protection against *Leishmania* infection.

The term "source" when used in "a S6 source" has the same meaning as the term "source" when used in "a L3 and/or a L5 source".

Each of the use or method or types of compositions defined herein comprising a L3 and/or a L5 source also apply for a S6 source.

Accordingly, in a preferred embodiment a S6 source is a polypeptide comprising an amino acid sequence that has at least 60% sequence identity or similarity with amino acid sequence SEQ ID NO:34 and/or which is encoded by a nucleotide sequence that has at least 60% identity with SEQ ID NO:35.

Accordingly, in a preferred embodiment a S6 source is a nucleic acid comprising a nucleic acid sequence that has at least 60% sequence identity or similarity with nucleotide sequence SEQ ID NO:35 and/or which encodes an amino acid sequence that has at least 60% identity with SEQ ID NO:34.

Method

In another aspect, the invention provides for a method to prevent and/or treat a parasitic disease and/or delay its progression and/or is able to elicit an immune response as defined herein: a method is therapeutically effective when it is able to elicit an immune response in a treated subject which preferably means that it is able to promote or trigger a $Th_1$ immune response against a given antigen L3 and/or L5 and/or against a given L3 and/or L5 source and/or that it is able to prevent and/or delay the development of a dermal or mucosal lesion and/or induces a significant reduction of the parasite load in a dermal and/or mucosal lesion and/or in an ear and/or in a draining lymph node (DLN) which preferably drains any of these infected regions (dermal, mucosal region, ear), as well as in an internal organ such as liver, spleen, bone marrow, kidney, brain, etc. herein. In this method, a vaccine of the invention functions as a therapeutic vaccine. Typically, there is a time period between infection and disease. In this case, a vaccine would act as a pharmacological immune product that would prevent and/or treat the disease and/or delay its progression by eliciting in the host an immune response that counteracts the pathological effect of the infection. A therapeutic vaccine differs from a prophylactic vaccine in that a therapeutic vaccine will induce protection in a patient who already has the infection or the disease. The invention encompasses either a therapeutic or a prophylactic vaccine. In this method, optionally a S4 and/or a S6 source may be used in combination with a L3 and/or a L5 source.

Use

In a further aspect, there is provided a further use of an L3 and/or an L5 source for diagnosing a parasitic disease in a subject. A parasitic disease, an L3 and/or an L5 source and a subject have been earlier defined herein. In this use, optionally a S4 and/or a S6 source may be used in combination with a L3 and/or a L5 source.

One advantage of the present invention is that it allows to reach a specific and early diagnostic of a broader spectrum of parasitic diseases. One example of a parasitic disease in which this is the case is leishmaniasis. In a preferred embodiment, a parasitic disease is leishmaniasis or malaria. More preferably, a parasitic disease is caused by a *Leishmania* or by a *Plasmodium* species. In a further preferred embodiment, a parasitic disease is caused by a different species than the species from which a L3 and/or L5 is derived. In particular, leishmaniasis caused by one species from the genus *Leishmania* may be diagnosed by using a composition based on an L3 and/or an L5 source from another *Leishmania* species. In one embodiment, leishmaniasis caused by *L. major* is successfully diagnosed with a composition comprising an L3 and/or an L5 source from *L. major, L. infantum, L. brazilienzis* or *L. mexicana*. Alternatively, other parasitic diseases, such as malaria, may be successfully diagnosed with a composition based on an L3 and/or an L5 source of another species, for instance based on an L3 and/or an L5 source of *L. infantum, L. major, L. brazilienzis* or *L. mexicana*.

In principle, any subject could be diagnosed using the invention. The diagnosis method may be applied as often as necessary in a subject. Preferably, a subject diagnosed is a subject suspected to have a risk of having been infected with said parasite causing said parasitic disease. A subject suspected to have a risk of having been infected with said parasite may live in an endemic area or has been visiting an endemic area. An endemic area includes North Africa from Algeria to Saudi Arabia, Kenya, Sudan, Ethiopia. It further includes Southern Europe: Mediterranean countries Spain, France, Greece, etc. It also includes Central (All countries) and South America: Brazil, Venezuela, Peru, Bolivia, Colombia North of Argentina, Paraguay, Uruguay, Central to South West Asia: India, Iran, Iraq, Mongolia, Afghanistan, Nepal, Bangladesh.

In the context of the invention, a use as defined herein is preferably an in vitro or ex vivo use. It preferably means that said use is carried out on a sample from said subject.

Preferred samples include blood, serum, plasma, saliva, cerebrospinal fluid or urine. More preferably, the sample is a blood or serum sample obtained from a subject.

In a preferred embodiment, a diagnosis is reached before the apparition of a symptom of said parasitic disease, so-called pre-symptomatic diagnosis or diagnosis of an asymptomatic subject. In this context, "pre-symptomatic" preferably means at least one day, at least two days, at least three days, at least four days, at least five days, at least six days, at least seven days, at least eight days, at least nine days, at least ten days at least 15 days, at least 20 days, at least 25 days, at least 30 days or more before the apparition of a first symptom. A first symptom or a first clinical sign associated with a parasitic disease such as leishmaniasis may be selected from the following list: fever, splenomegaly, hepatomegaly, lymphadenopathy, conjunctivitis, dermatitis onychogriphosis, keratoconjunctivitis, apathy and cachexia. Most of them can be simple detected by physical external examination. Each of conjunctivitis, dermatitis, onychogriphosis, keratoconjunctivitis is a form of cutaneous alteration.

A preferred first symptom linked to leishmaniasis is lymphadenopathy. It can be detected by physical external examination such as palpation.

In another preferred embodiment, a diagnosis is reached before the apparition of some of the symptoms of said parasitic disease, so-called diagnosis of an oligosymptomatic subject. In this context, "oligosymptomatic" preferably means a subject having a maximum of three of the symptoms as defined above.

In another preferred embodiment, a diagnosis is reached before the apparition of all symptoms of said parasitic disease, so-called diagnosis of a symptomatic subject. In this context, "symptomatic" preferably means a subject having at least four of the symptoms as defined above including a form of cutaneous alteration as defined above.

The skilled person will understand that the most important type of diagnosis is the diagnosis of asymptomatic subjects, since it will help preventing the further spreading of the disease and asymptomatic subjects could be helped and cured more efficiently if they are diagnosed in such a stage.

In this use, an L3 and/or L5 and/or a S4 and/or a S6 source may be an L3 and/or L5 and/or a S4 and/or a S6 protein or protein fragment that are used for detecting the presence of an antibody in a sample as explained in coming section.

Alternatively, an L3 and/or an L5 and/or a S4 and/or a S6 source may be a nucleic acid molecule that are used to detect the presence of an L3 and/or L5 and/or a S4 and/or a S6 nucleic acid in a sample as explained in coming section.

Method

In a further aspect there is provided a method for diagnosing a parasitic disease in a subject using an L3 and/or an L5 source, the method comprising determining whether an antibody recognizing an L3 and/or an L5 source is present in a sample obtained from the subject. Optionally, a S4 and/or a S6 source may also be used in combination with a L3 and/or a L5 source. A preferred method of the invention is as for a preferred use of the invention preferably carried out in vitro or ex vivo. A definition has been given earlier herein.

In a preferred method, an L3 and/or an L5 source is present in a composition. In a preferred embodiment, another compound is present is said composition. Alternatively, no other compound is present in said composition.

In a preferred embodiment, other compounds are used sequentially or simultaneously with a L3 and/or an L5 source in order to improve the specificity of the method. It is advantageous for example to use other compounds that will be able to discriminate between asymptomatic, oligosymptomatic or symptomatic subject and vaccinated subject. More preferably, such compounds are not present in a single composition together with an L3 and/or an L5 source. Each of the proteins identified in the section entitled composition may be used in this context. For example said compounds are selected from a group consisting of a source of other proteins from a parasite causing a parasitic disease (19) such as Leishmaniasis. A source of a given protein is given the same meaning as a source of an L3 and/or an L5 as defined earlier herein. A preferred protein is in this context a histone such as a H2A, H2B, H3, H4, another ribosomal protein such as Li2A (LiP), LiP2b (LiP'), LiP0, L2, L7, L8, L16, S6, L19 and S4. Another example is the use of poly-proteins containing several parasite antigens (59, 61). An example of a poly-protein is protein Q as identified in EP 1 141 305.Protein Q or a part or a fragment thereof or a source of protein Q or a source of a fragment of protein Q may be used in combination with a source of L3 and/or L5.

Preferred antigens include a histone protein or fragment thereof or a nucleic acid molecule encoding said histone. More preferably, a histone protein is H2A, H2B, H3 and/or H4 as identified in EP 1 687 023. Histones H2A, H2B, H3 and H4 are well-conserved nuclear proteins and their sequence is well-known in the art, see reference 39. Preferably the histones are obtained from an organism which is close to the disease causing organism in the evolutionary tree. Therefore, of particular interest as a source of histones to be used in the treatment of parasitic diseases such as leishmaniasis are protozoans and in particular members of the trypanosomatid family, as for example plasmodium, such as *Plasmodium falciparum* or more in particular different species of the trypanosomatical protozoan *Leishmania*.

In a more preferred diagnosis method, a parasitic disease is diagnosed when a detectable amount of an antibody recognizing an L3 and/or an L5 source, preferably protein or peptide or protein part is present and/or when an increase of the amount of said antibody is present. In a control or healthy subject, said antibody is generally not detectable.

Detection of the presence of said antibody is carried out using methods known to the skilled person such as an ELISA. Preferred ways of detection are described in example 1.

An antibody recognizing an L3 and/or an L5 source, preferably a protein or peptide or protein part preferably means that at least one antibody is present which is able to recognize at least one compound present in an L3 and/or an L5 source. Said compound may be an L3 and/or an L5 protein or an L3 and/or an L5 protein fragment or protein part or peptide. The same holds for an antibody recognizing a S4 and/or a S6 source.

In another method, an L3 and/or L5 nucleic acid molecule is detected using another nucleic acid molecule. An L3 and/or L5 nucleic acid molecule is preferably a nucleic acid molecule encoding an L3 and/or a L5 molecule as identified earlier herein or a part thereof. Another nucleic acid molecule is preferably a primer designed to be able to detect the presence of an L3 and/or an L5 nucleic acid molecule in a PCR reaction or by Northern blotting. The same holds for a primer able to detect the presence of a S4 and/or a S6 nucleic acid molecule. Preferred primers to detect the presence of an L3 and/or an L5 nucleic acid molecule comprise or consist of the following sequences: Primer sequences to specifically detect an L3 by PCR Sense, 5'-AACACGAAGGAGGGCAAGGTC-3' (nucleotides 418 to 438 of the LmL3 sequence) (SEQ ID NO:38)

Antisense 5'-CTTCTTCGCGGCCTTTGCCTTG-3' (reverse and complementary to nucleotides 1242 to 1263 of the LmL3 sequence) (SEQ ID NO:39)

Primer sequences to specifically detect an L5 by PCR

Sense, 5'-TGCACGCTGGCAAATTGGGTAC-3' (nucleotides 10 to 31 of the LmL5 sequence) (SEQ ID NO:40)

Antisense 5'-CTT CTT CGT GCG CAC AGC AG-3' (reverse and complementary to nucleotides 464 to 483 of the LmL5 sequence) (SEQ ID NO:41)

Primer sequences to specifically detect an L3 by Northern blot

5'-CTTCTTCGCGGCCTTTGCCTTG-3' (reverse and complementary to nucleotides 1242 to 1263 of the LmL3 sequence) (SEQ ID NO:42)

Primer sequences to specifically detect an L5 by Northern blot

5'-CTT CTT CGT GCG CAC AGC AG-3' (reverse and complementary to nucleotides 464 to 483 of the LmL5 sequence) (SEQ ID NO:43). Detection or an increase of the expression level of an L3 and/or L5 nucleic acid molecule is preferably defined as being a detectable change of the expression level of said nucleic acid molecule as compared to the expression level of said nucleic acid molecule in a control subject. Usually a control subject will not comprise such an L3 and/or L5 nucleic acid molecule. Preferably, an increase of the expression level of an L3 and/or L5 nucleic acid molecule means an increase of at least 5% of the expression level of the nucleotide sequence using PCR.

Assay

In a further aspect, there is provided an assay device for diagnosing a parasitic disease in a subject, wherein the device comprises an L3 and/or an L5 source. Optionally, a S4 and/or a S6 source may also be present in this assay device in combination with a L3 and/or a L5 source. The presence of an antibody specifically recognizing said source may be detected by any standard methods known to those skilled in the art (see, e.g., Harlow and Lane, Antibodies: A Laboratory Manual, Cold Spring Harbor Laboratory, 1988, which is incorporated herein by reference). Suitable methods include affinity chromatography co-electrophoresis (ACE) assays and (Enzyme-Linked Immuno Sorbent Assay) ELISA. Preferably, the assay comprises an ELISA. Several assays are more extensively described below.

In a preferred embodiment, an assay involves the use of an L3 and/or an L5 source immobilized on a solid support to bind to and remove an antibody from the sample. Said bound antibody may then be detected using a detection reagent that binds to the antibody/L3 and/or L5 source complex and contains a detectable reporter group. Suitable detection reagents include antibodies that bind to the antibody/L3 and/or L5 source complex and free polypeptide labeled with a reporter group (e.g., in a semi-competitive assay). Alternatively, a competitive assay may be utilized, in which an antibody that binds to an L3 and/or an L5 source is labelled with a reporter group and allowed to bind to the immobilized L3 and/or L5 source after incubation of the source with the sample. The extent to which components of the sample inhibit the binding of the labelled antibody to said L3 and/or L5 source is indicative of the reactivity of the sample with the immobilized L3 and/or L5 source.

A solid support may be any material known to those of ordinary skill in the art to which an L3 and/or L5 source may be attached. For example, a support may be a test well in a microtiter plate or a nitrocellulose or other suitable membrane. Alternatively, a support may be a bead or disc, such as glass, fiberglass, latex or a plastic material such as polystyrene or polyvinylchloride. A support may also be a magnetic particle or a fiber optic sensor, such as those disclosed, for example, in U.S. Pat. No. 5,359,681.

An L3 and/or an L5 source may be bound to the solid support using a variety of techniques known to those in the art. In the context of the present invention, the term "bound" refers to both non-covalent association, such as adsorption, and covalent attachment (which may be a direct linkage between the antigen and functional groups on the support or may be a linkage by way of a cross-linking agent). Binding by adsorption to a well in a microtiter plate or to a membrane is preferred. In such cases, adsorption may be achieved by contacting an L3 and/or an L5 source, in a suitable buffer, with the solid support for a suitable amount of time. The contact time varies with temperature, but is typically between 1 hour and 1 day. In general, contacting a well of a plastic microtiter plate (such as polystyrene or polyvinylchloride) with an amount of an L3 and/or an L5 source ranging from 10 ng to 1 g, and preferably 100 ng, is sufficient to bind an adequate amount of an L3 and/or an L5 source. Here also, when a quantity or amount of an L3 and/or L5 source is given, it defines the total amount of an L3 and/or an L5 source used.

Covalent attachment of an L3 and/or an L5 source to a solid support may generally be achieved by first reacting the support with a bifunctional reagent that will react with both the support and a functional group, such as a hydroxyl or amino group, on the polypeptide. For example, an L3 and/or an L5 source may be bound to a support having an appropriate polymer coating using benzoquinone or by condensation of an aldehyde group on the support with an amine and an active hydrogen on the polypeptide (see, e.g., Pierce Immunotechnology Catalog and Handbook (1991) at A12-A13).

In certain embodiments, an assay is an enzyme linked immunosorbent assay (ELISA). This assay may be performed by first contacting an L3 and/or an L5 source that has been immobilized on a solid support, commonly the well of a microtiter plate, with the sample, such that antibodies specific for said L3 and/or L5 source within the sample are allowed to bind to the immobilized L3 and/or L5 source. Unbound sample is then removed from the immobilized source and a detection reagent capable of binding to the immobilized antibody-L3 and/or L5 source complex is added. The amount of detection reagent that remains bound to the solid support is then determined using a method appropriate for the specific detection reagent.

Once the L3 and/or L5 source has been immobilized on the support, the remaining protein binding sites on the support are typically blocked. Any suitable blocking agent known to those of ordinary skill in the art, such as bovine serum albumin (BSA) or Tween 20 (Sigma Chemical Co., St. Louis, Mo.) may be employed. The immobilized L3 and/or L5 source is then incubated with the sample, and antibody (if present in the sample) is allowed to bind to said source. A sample may be diluted with a suitable diluent, such as phosphate-buffered saline (PBS) prior to incubation. In general, an appropriate contact time (i.e., incubation time) is that period of time that is sufficient to permit detect the presence of antibody within a sample. Preferably, the contact time is sufficient to achieve a level of binding that is at least 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20 Detection reagent may then be added to a solid support. An appropriate detection reagent is any compound that binds to the immobilized antibody-L3 and/or L5 source complex and that can be detected by any of a variety of means known to those in the art. Preferably, the detection reagent contains a binding agent (such as, for example, Protein A, Protein G, immunoglobulin, lectin or free antigen) conjugated to a reporter group. Preferred reporter groups include enzymes (such as horseradish peroxidase), substrates, cofactors, inhibitors, dyes, radionucleides, luminescent groups, fluorescent groups and biotin. The conjugation of binding agent to reporter group may be achieved using standard methods known to those of ordinary skill in the art. Common binding agents may also be purchased conjugated to a variety of reporter groups from many sources (e.g., Zymed Laboratories, San Francisco, Calif. and Pierce, Rockford, Ill.).

The detection reagent is then incubated with the immobilized antibody L3 and/or L5 source complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group.

The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of an antibody specific for a parasitic disease such as Leishmaniasis in a sample, the signal detected from the reporter group that remains bound to the solid support is generally compared to a signal that corresponds to a predetermined cut-off value. In one preferred embodiment, the cut-off value is preferably the average mean signal obtained when the immobilized L3 and/or L5 source is incubated with a sample from an uninfected subject. In general, a sample generating a signal that is three standard deviations above the predetermined cut-off value is considered positive (i.e., reactive with an L3 and/or L5 source). In an alternate preferred embodiment, the cut-off value is determined using a Receiver Operator Curve, according to the method of Sackett et al., Clinical Epidemiology: A Basic Science for Clinical Medicine, p. 106-7 (Little Brown and Co., 1985). Briefly, in this embodiment, the cut-off value may be determined from a plot of pairs of true positive rates (i.e., sensitivity) and false positive rates (100%-specificity) that correspond to each possible cut-off value for the diagnostic test result.

The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate.

In a related embodiment, an assay is performed in a flow-through or strip test format, wherein an L3 and/or an L5 source is immobilized on a membrane such as nitrocellulose. In the flow-through test, antibodies within the sample bind to the immobilized L3 and/or L5 source as the sample passes through the membrane. A detection reagent (e.g., protein A-colloidal gold) then binds to the antibody-L3 and/or L5 source complex as the solution containing the detection reagent flows through the membrane. The detection of bound detection reagent may then be performed as described above. In the strip test format, one end of the membrane to which source is bound is immersed in a solution containing the sample. The sample migrates along the membrane through a region containing detection reagent and to the area of immobilized polypeptide. Concentration of detection reagent at an L3 and/or L5 source indicates the presence of an antibody specific for an antigen of a parasite causing a parasitic disease such as Leishmaniasis in the sample. Typically, the concentration of detection reagent at that site generates a pattern, such as a line, that can be read visually. The absence of such a pattern indicates a negative result. In general, the amount of an L3 and/or L5 source immobilized on a membrane is selected to generate a visually discernible pattern when a sample contains a level of antibody that would be sufficient to generate a positive signal in an ELISA, as discussed above. Preferably, the amount of an L3 and/or L5 immobilized on a membrane ranges from 25 ng to 500 ng. Such tests can typically be performed with a very small amount (e.g., one drop) of subject serum or blood.

The disclosure of each element of the assay device when applied to a L3 and/or a L5 source may also applied for a S4 and/or a S6 source if a S4 and/or a S6 source is used in combination with a L3 and/or a L5 source in this assay device.

Any subject or physician could use this device at office/home, repeat the use of such device as often as necessary.

Usually additional molecules are used in an assay as a positive or negative control. A typical positive control could be an antibody recognizing a molecule which is known to be present in a sample to be tested. A typical negative control could be an antibody recognizing a molecule which is known to be absent in a sample to be tested.

General Definitions

In the context of the invention, a protein or a protein fragment is represented by an amino acid sequence.

In the context of the invention, a nucleic acid molecule is represented by a nucleic acid or nucleotide sequence which encodes a protein or a polypeptide or a protein fragment.

A nucleic acid molecule may comprise a regulatory region.

It is to be understood that each nucleic acid molecule or protein or protein fragment as identified herein by a given Sequence Identity Number (SEQ ID NO) is not limited to this specific sequence as disclosed. Each gene sequence or nucleotide sequence as identified herein encodes a given protein or polypeptide or protein fragment or is it self a protein or a protein fragment. Throughout this application, each time one refers to a specific nucleotide sequence SEQ ID NO (take SEQ ID NO:2 or 4 as example), one may replace it by:
  i. a nucleotide sequence comprising a nucleotide sequence that has at least 60% sequence identity or similarity with SEQ ID NO:2 or 4 or 49 or 51 or 53 or 55 or 65 (as example).
  ii. a nucleotide sequences the complementary strand of which hybridizes to a nucleic acid molecule of sequence of (i);
  iii. a nucleotide sequence the sequence of which differs from the sequence of a nucleic acid molecule of (iii) due to the degeneracy of the genetic code.
  iv. a nucleotide sequence that encodes an amino acid sequence that has at least 60% amino acid identity or similarity with an amino acid sequence encoded by a nucleotide sequence SEQ ID NO:2 or 4 or 49 or 51 or 53 or 55 or 65.

Throughout this application, each time one refers to a specific amino acid sequence SEQ ID NO (take SEQ ID NO:1 or 3 or 48 or 50 or 52 or 54 or 56 as example), one may replace it by:
  a polypeptide comprising an amino acid sequence that has at least 60% sequence identity or similarity with amino acid sequence SEQ ID NO:1 or 3 or 48 or 50 or 52 or 54 or 56.

Each nucleotide sequence or amino acid sequence described herein by virtue of its identity or similarity percentage (at least 60%) with a given nucleotide sequence or amino acid sequence respectively has in a further preferred embodiment an identity or a similarity of at least 65%, 70%, 75%, 80%, 85%, 90%, 95%, 97%, 98%, 99% or more identity or similarity with the given nucleotide or amino acid sequence respectively. In a preferred embodiment, sequence identity or similarity is determined by comparing the whole length of the sequences as identified herein.

"Sequence identity" is herein defined as a relationship between two or more amino acid (polypeptide or protein) sequences or two or more nucleic acid (polynucleotide) sequences, as determined by comparing the sequences. In a preferred embodiment, sequence identity is calculated based on the full length of two given SEQ ID NO or on part thereof. Part thereof preferably means at least 50%, 60%, 70%, 80%, 90%, or 100% of both SEQ ID NO. In the art, "identity" also means the degree of sequence relatedness between amino acid or nucleic acid sequences, as the case may be, as determined by the match between strings of such sequences.

"Similarity" between two amino acid sequences is determined by comparing the amino acid sequence and its conserved amino acid substitutes of one polypeptide to the sequence of a second polypeptide. "Identity" and "similarity" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm may also be used to determine identity.

Preferred parameters for polypeptide sequence comparison include the following: Algorithm: Needleman and Wunsch, J. Mol. Biol. 48:443-453 (1970); Comparison matrix: BLOSSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, Wis. The aforementioned parameters are the default parameters for amino acid comparisons (along with no penalty for end gaps).

Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to Ser; Arg to Lys; Asn to Gln or His; Asp to Glu; Cys to Ser or Ala; Gln to Asn; Glu to Asp; Gly to Pro; His to Asn or Gln; Ile to Leu or Val; Leu to Ile or Val; Lys to Arg; Gln or Glu; Met to Leu or Ile; Phe to Met, Leu or Tyr; Ser to Thr; Thr to Ser; Trp to Tyr; Tyr to Trp or Phe; and, Val to Ile or Leu.

Nucleic Acid Construct

A nucleic acid construct comprises a nucleotide sequence encoding a protein or a protein fragment as defined herein. A nucleic acid construct comprising a nucleic acid molecule coding for a given protein or protein fragment as defined herein will ensure expression of the given nucleic acid molecule, and of the corresponding protein or protein fragment in a treated subject. In a more preferred embodiment, a nucleic acid construct comprises more than one nucleic acid molecule, each nucleic acid molecule coding for a given protein or protein fragment. In an even more preferred embodiment, a nucleic acid construct comprises two, three, four nucleic acid molecules, each nucleic acid molecule coding for a given protein or protein fragment. In a preferred embodiment, a nucleic acid construct comprises an expression cassette, said expression cassette comprising each needed nucleic acid molecule. Each nucleic acid molecule is operably linked with other nucleic acid molecule present. Most preferably, a suitable promoter is operably linked with the expression cassette to ensure expression of the nucleic acid molecule in a subject.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a product or a composition or a L3 or a L5 source as defined herein may comprise additional component(s) than the ones specifically identified, said additional component(s) not altering the unique characteristic of the invention.

In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The invention is further illustrated by the following example, which should not be construed for limiting the scope of the present invention.

(a) Twelve BALB/c mice were s.c. infected with $5 \times 10^4$ *L. major* stationary-phase promastigotes in the left footpad and sera were obtained eight weeks after challenge. IgG1 and IgG2a antibody relativities of the sera from mice with cutaneous leishmaniasis (MCL) against rLmL3 and rLmL5 were determined individually by ELISA. Lack of reactivity of the sera from the same mice before infection is also represented. ELISA reactivity of sera from dogs with symptomatic CVL and control sera against rLmL3 (b) and rLmL5 (c) recombinant proteins.

FIG. 3. Cytokine production induced by vaccination in BALB/c mice. BALB/c mice (six per group) were s.c. immunized three times with 10 µg of rLmL3+50 µg of CpG-ODN (L3+CpG) or 10 µg of rLmL5+50 µg of CpG-ODN (L5+CpG), with 50 µg of CpG-ODN (CpG) or with PBS (Saline). Spleen cells were obtained four weeks after vaccination and cultured in vitro for 48 h in the presence of rLmL3 (a, c and e), rLmL5 (b, d and f) and in medium alone. The level of IFN-γ (a and b), IL-4 (c and d) and IL-10 (e and f) was assessed by ELISA in culture supernatants. Each bar represents the means±SD of data from individual mice.

Figure 4A:
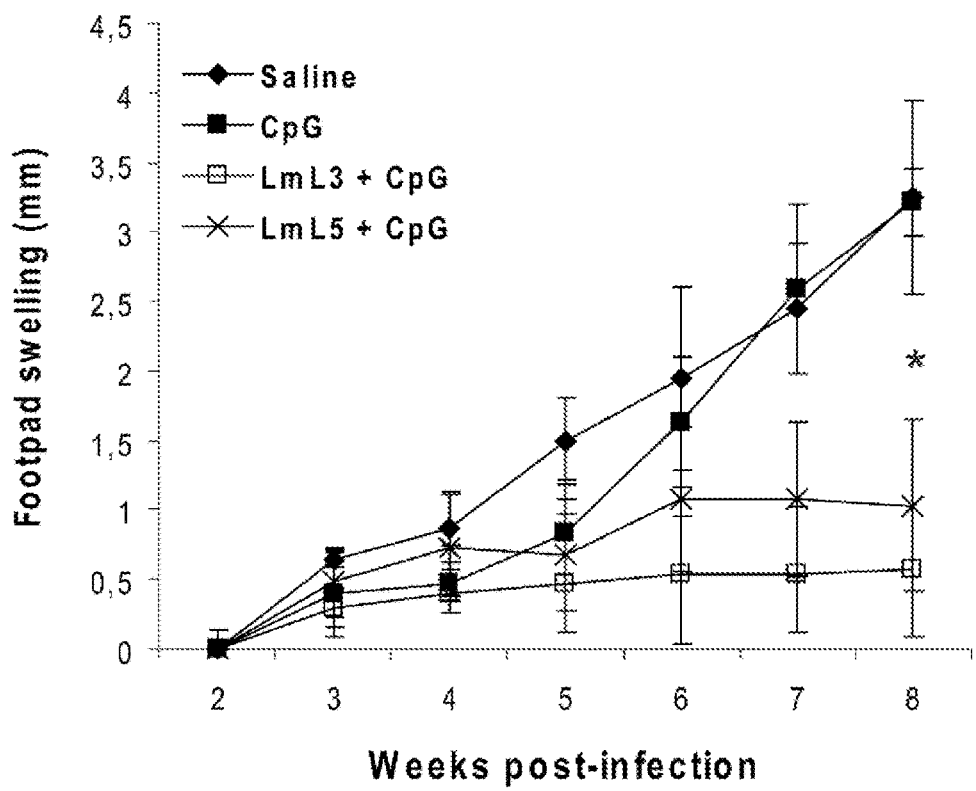
Figure 4B:
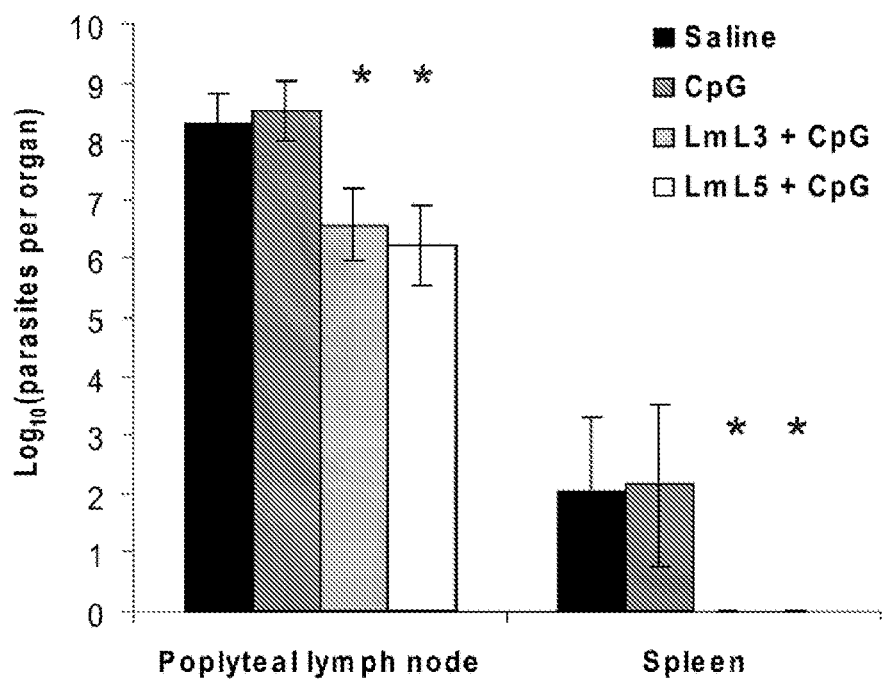

FIG. 4. Course of *L. major* infection in BALB/c vaccinated mice after challenge. (a Footpad swelling is given as the difference of thickness between the infected and the uninfected contra-lateral footpads. (b The number of viable parasites in the poplyteal draining lymph node of the infected leg and spleen were individually determined by limiting dilution at week eight post-challenge. (*, P<0.01)

FIG. 5. Cellular immune responses elicited by infection in L3+CpG ODN vaccinated mice. Spleen cells cultures were established at week eight after parasite challenge. Cells were non-stimulated (medium) or separately stimulated with LRP (*Leishmania* Ribosomal Proteins) (12 µg ml$^{-1}$), SLA (Soluble *Leishmania* Antigens) (12 µg ml$^{-1}$), MRP (Mouse Ribosomal Proteins) (12 µg ml$^{-1}$) or L3 (6 ηg ml$^{-1}$) for 48 hours in 5% $CO_2$, at 37° C. IFN-γ (a,) IL-4 (b) and IL-10 (c) levels were measured in culture supernatants by capture enzyme-linked immunosorbent assay. Each bar represents average plus standard deviation of cytokine levels determined in six individual mice per group.

FIG. 6. Cellular immune responses elicited by infection in L5+CpG ODN vaccinated mice. Spleen cells cultures were established at week eight after parasite challenge. Cells were non-stimulated (medium) or separately stimulated with LRP (12 µg ml$^{-1}$), SLA (12 µg ml$^{-1}$), MRP (12 µg ml$^{-1}$) or L5 (6 µg ml$^{-1}$) for 48 hours in 5% $CO_2$, at 37° C. IFN-γ (a), IL-4 (c) and IL-10 (b) levels were measured in culture supernatants by capture enzyme-linked immunosorbent assay. Each bar represents average plus standard deviation of cytokine levels determined in six individual mice per group.

FIG. 7 Course of *L. braziliensis* infection in BALB/c vaccinated mice after challenge. (A) Inflammatory lesions in the infected ears. Lesion sizes (in millimeters) are expressed as the mean±SD from one experiment performed with five mice. *P<0.05 between mice vaccinated with rLmL5+CpG-ODN or rLmL3+CpG-ODN and both control groups. (B) Parasite burden in the ear dermis quantitated at week five post-infection. Results are expressed as the mean±SD of five ears per group. *P<0.05 significant decrease between rLmL5+CpG-ODN and both control mice groups.

FIG. 8 Ribosomal location of the LmL3 and LmL5 proteins. One µg of the rLmL3 protein (A), 1 µg of the rLmL5 protein (B) and 10 µg of *Leishmania major* LRP extracts (A and B) were electrophoresed on linear 10-13% gradient SDS-PAGE gels. Coomasie blue staining of the gels are shown at the left panels (A and B). Equivalent gels were blotted and probed with the sera from mice immunized with rLmL3 (panel α-LmL3) (A) and with the affinity-purified an anti LmL5 antibody fraction of five canine visceral leishmaniasis sera (panel α-LmL5) (B).

FIG. 9 Analysis of the infection parameters in mice vaccinated with the ribosomal proteins S6, L2, L7, L8 and L6 in the presence of CpG. (A) Lesion development in the infected groups was monitored weekly until t week eight after infection. Differences in the footpad swelling between S6 plus CpG ODN and control (saline and adjuvant) groups were statistically significant at week eight after infection (*P<0.05). (B) Parasite burden determination in the DLNs and spleens analyzed eight weeks after infection. Differences in the parasite loads in the spleens of the S6 plus CpG ODN vaccinated group and the spleen of control (saline and adjuvant) groups were statistically significant (*P<0.05). For clarity, only the SD from saline group and the S6 plus CpG ODN vaccinated group is shown.

FIG. 10. Immune responses elicited by S6 plus CpG ODN vaccination. (A) Serum samples were obtained from mice immunized with S6 plus CpG ODN, CpG ODN and saline four weeks after the administration of the last doses. Sera were individually tested by ELISA to determine the presence of anti-S6 specific IgG, IgG1 and IgG2a antibodies.

(*P<0.05) Statistical significant differences between the S6 plus CpG ODN group and control (saline and CpG) groups. (B) Spleen cells were non-stimulated (medium) or stimulated with S6 for 48 hours in 5% $CO_2$, at 37° C. IFN-γ, IL-4 and IL-10 levels were measured in culture supernatants by capture enzyme-linked immunosorbent assay. Each bar represents average plus standard deviation of cytokine levels determined in four individual mice per group. (*P<0.05) Statistical significant differences between the S6 plus CpG ODN group and control (saline and CpG) groups.

Figure 11B:
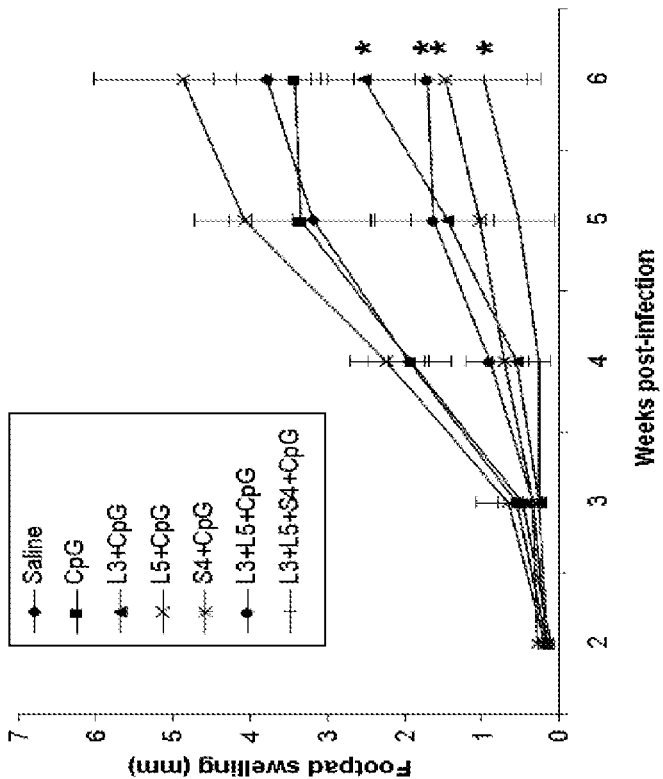
Figure 11A:
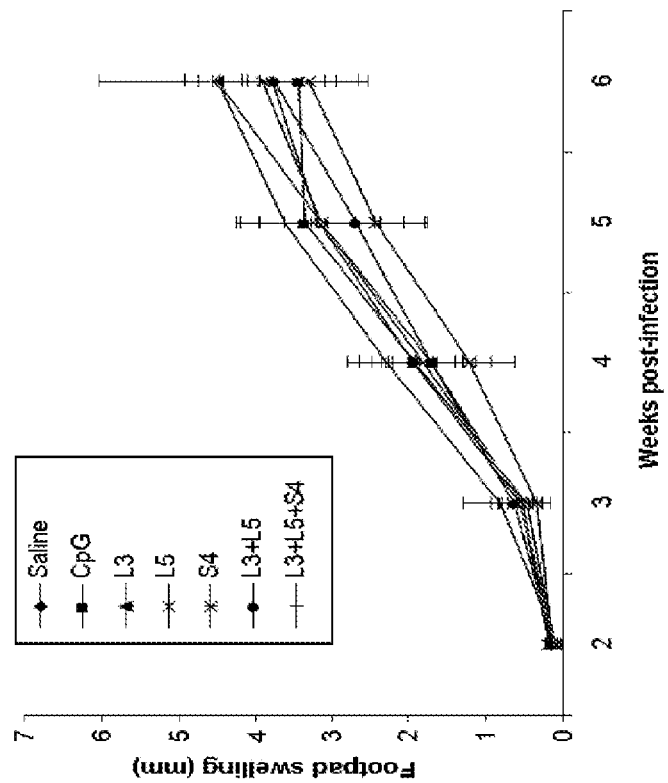

FIG. 11. Lesion development in mice immunized with L3, L5 and S4 individually or in mixed preparations in the absence or presence of CpG. Lesions was monitored weekly until week six after infection. (A) Control mice groups and mice groups vaccinated with the recombinant proteins without adjuvant. (B) Control mice groups and mice groups vaccinated with the recombinant proteins plus CpG ODN. (*P<0.05) Differences in the footpad swelling between L3 plus CpG ODN, L5 plus CpG ODN, L3 plus L5 plus CpG ODN or L3 plus L5 plus S6 plus CpG ODN and control (saline and adjuvant) groups were statistically significant at week six after infection.

FIG. 12. Parasites burdens in the vaccinated mice. Parasite loads were determined in the spleen and in the DLN at week seven after infection. (A) Control mice groups and mice groups vaccinated with the recombinant proteins without adjuvant. (B) Control mice groups and mice groups vaccinated with the recombinant proteins plus CpG ODN. (*P<0.05) Differences in the spleen parasite burdens between L3 plus CpG ODN, L5 plus CpG ODN, L3 plus L5 plus CpG ODN or L3 plus L5 plus S6 plus CpG ODN and control (saline and adjuvant) groups were statistically significant. (*P<0.05) Differences in the popliteal parasite burdens between L3 plus L5 plus CpG ODN or L3 plus L5 plus S6 plus CpG ODN and control (saline and adjuvant) groups were statistically significant.

FIG. 13. Diagrammatic representation of the proposed chimerical constructs. The designed primers and the cut sites selected for cloning is shown.

EXAMPLES

Example 1

Cloning of *Leishmania Major* L3 and L5 Proteins and Protective Effect Conferred by These Proteins Against *Leishmania Major* Infection Material and Methods Mice Strains and Parasites.

Female BALB/c mice (6-8 week old) were purchased from Harlan Interfauna Ibérica S.A. (Barcelona, Spain).

*L. major* parasites (WHOM/IR/-/173) were kept in a virulent state by passage in BALB/c mice. *L. major* amastigotes were obtained and transformed to promastigote by culturing at 26° C. in Schneider's medium (Gibco, BRL, Grand Island, N.Y., USA) supplemented with 20% fetal calf serum.

CpG-ODN.

Phosphorothioate-modified CpG-ODN (5'-TCAACGTTGA-3' and 5'-GCTAGCGTTAGCGT-3') (SEQ ID NO:5, 6) were synthesized by Isogen (The Netherlands).

Cloning of DNA Sequences Coding for *L. Major* Ribosomal Proteins L3 and L5.

The open reading frame (ORF) coding for the *L. major* L3 and L5 proteins were obtained from the *L. major* genome database (www.genedb.org/genedb/leish) using the *S. cerevisiae* L3 and L5 proteins sequences as probes (56). For expression of rLmL3 and rLmL5 proteins, their coding regions (CR) were PCR amplified using as template the DNA from *L. major* (MHOM/IL/80(Friedlin)). Amplified DNAs were cloned into the pBluescript plasmid (Stratagene, La Jolla Calif.) and sequenced before cloning into the pQE30 expression vector (QIAGEN, Hilden, Germany).

For cloning of the LmL3 CR the primers employed were: sense, 5'-CGGGATCCATGTCTCACTGCAAGTTCGAG-3' (positions 1 to 20 of the LmL3 CR (LmjF34.2880)) (SEQ ID NO: 44); antisense, 5'-AACTGCAGTTACTTCTTCGCGGCCTTTG-3' (reverse and complementary to positions 1241 to 1260 of the LmL3 CR (LmjF34.2880)) (SEQ ID NO:45). BamHI and PstI restriction sites (underlined) were included for cloning purposes.

For cloning of the LmL5 CR the primers employed were: sense, 5'-CGGGATCCATGTGCACGC TGGCAAATTG-3' (positions 1 to 20 of the LmL5 CR (LmjF35.1890)) (SEQ ID NO:46); antisense, 5'-CCCAAGCTTTTACTTGCCGAGGCGCTCGC-3' (reverse and complementary to positions 968-987 of the LmL5 CR (LmjF35.1890.319)) (SEQ ID NO:47). BamHI and HindIII restriction sites (underlined) were included for cloning purposes.

Protein Purification.

The rLmL3 and rLmL5 proteins were over-expressed in *Escherichia coli* transformed with pQE-LmL3 or with pQE-LmL5 plasmids and purified under denaturing conditions onto Ni-nitrilotriacetic acid (Ni-NTA) agarose columns (Qiagen). After binding to the Ni-NTA agarose recombinant proteins were refolded on the affinity column as described (57). The recombinant proteins were passed through a polymyxin-agarose column (Sigma, St. Louis, Mo.). Residual endotoxin content (<12 pg/μg of recombinant protein) was measured by the Quantitative Chromogenic *Limulus* Amebocyte Assay QCL-1000 (BioWhittaker, Walkersville, Md.).

Immunizations, Parasite Challenge and Parasite Quantification.

Two independent BALB/c mice groups (six per group) were subcutaneously (s.c.) inoculated in the right footpad with 10 μg of rLmL3 or 10 μg of rLmL5 mixed with 25 μg of each CpG-ODN. As control two additional mice groups were inoculated with 25 μg of each CpG-ODN alone, or with phosphate saline buffer (PBS). Each group was boosted two and four weeks later with the same dose used for priming. Parasite challenge was carried out by s.c. inoculation with $5\times10^4$ stationary-phase promastigotes of *L. major* (WHOM/IR/-/173) into the left (untreated) footpad four weeks after the last inoculation. Footpad swelling was measured with a metric caliper and calculated as thickness of the left footpad minus thickness of the right footpad. The number of parasites was determined in the ears, draining lymph nodes (DLN) and spleen by limiting dilution assay as described (70).

Leishmanial Antigens and Mouse Ribosomal Proteins.

For preparation of *L. major* LRP, $10^9$ promastigotes were harvested, washed twice in pre-chilled PBS and resuspended in 1 ml NP40 lysis buffer (10 mM Tris HCl, pH 8.0, 150 mM NaCl, 1.5 mM $MgCl_2$ and 0.5% NP40) and pipetted up and down 10 times. After lyses, samples were microfuged at 3,000×g for 2 min at 4° C. to pellet the nuclei. Supernatant was twice microfuged at 13,000×g for 15 min at 4° C. and the ribosomes were prepared from the cytosolic supernatant as described in [57]. Briefly, cytosol was submitted to high speed centrifugation at 90,000 rpm for 30 min at 4° C. in a Beckman TL100.3 rotor. The crude ribosomal pellet was resuspended in buffer A (20 mM Tris-HCl, pH 7.4, 500 mM $AcNH_4$, 100 mM $MgCl_2$, 5 mM β-mercaptoethanol) and centrifuged through a discontinuous sucrose gradient (20/40%) in buffer A at 90,000 rpm at 4° C. in a TL100.3 rotor. The pellet of washed ribosomes was dissolved in PBS and sonicated until complete ribosomal RNA degradation. Mouse ribosomal proteins extracts (MRP) were prepared from $5\times10^7$ RAW 264.7 murine macrophage cells using the same procedure.

Total proteins of *L. major* (soluble *Leishmania* antigen [SLA]) was prepared as described (70). Briefly, *L. major* promastigotes ($10^{10}$) were washed twice in PBS, resuspended in 500 ml of PBS and lysed by three freezing and thawing cycles. After cell lysis, soluble antigens were separated from the insoluble fraction by centrifugation for 15 min at 12,000×g using a microcentrifuge. Supernatants were aliquoted and stored at −70° C.

Measurement of Cytokines in Supernatants

The release of IFN-γ, IL-10 and IL-4 was measured in the supernatants of splenocytes cells cultures stimulated with the recombinant proteins using commercial ELISA kits (Diaclone, Besancon, France). Briefly, 3×10⁶ spleen cells were seeded in 48-well plates during 48 h at 37° C. in the presence of rLmL3 (6 μg ml$^{-1}$) or rLmL5 (6 μg ml$^{-1}$) or medium alone.

Detection of Anti-L3 and Anti-L5 Antibody Responses in Mice and Dogs

Canine serum samples were collected from 20 clinically symptomatic dogs naturally infected with *Leishmania infantum* in the Extremadura region (Spain). Infected animals were clinically and analytically evaluated at the Department of Parasitology of the Veterinary School, Extremadura University, Caceres, Spain. All sera were positive when tested by indirect immunofluorescence, and the presence of amastigote forms of the parasite was confirmed by direct observation in poplyteal and prescapular lymphoid nodes. Control sera were obtained from 8 healthy animals maintained at the Department of Parasitology (Extremadura University).

Sera from 12 BALB/c mice experimentally infected with 5×10⁴ stationary-phase promastigotes of *L. major* (WHOM/IR/-/173) were collected at week eight after infection. As control the sera from the same mice were collected before infection.

Standard ELISA plates were coated overnight at room temperature with 100 μl of each one of the recombinant ribosomal proteins (2 μg ml$^{-1}$ in PBS). Canine and murine serum samples were assayed at 1/200 dilution in PBS-Tween 20 (0.5%)-casein (5%). As secondary antibodies horseradish peroxidase-conjugated anti-dog-IgG (1/1000), anti-muse-IgG1 (1/1000) and anti-mouse-IgG2a (1/500) purchased from Nordic Immunological Laboratories (Tilburg, The Netherlands) were used. Ortophenyle diamine dihydrochloride (OPD) (Dako, A/S, Glostrup, Denmark) was used as peroxidase substrate for ELISA assays. After 15 min, the reaction was stopped with the addition of 100 μl of $H_2SO_4$ 1M and the absorbance was read at 450 nm.

Statistical Analysis

Statistical analysis was performed by a Student's t-test. Differences were considered significant when P<0.05.

Results and Discussion

Identification, Cloning and Expression of the LmL3 and LmL5 Proteins.

For the identification of the *L. major* L3 and L5 coding regions we performed a BLASTP search using as probes the *S. cerevisiae* L3 and L5 aminoacid sequences (YOR063w and YPL131w, respectively) [58]. Two different entries (LmjF34.2880 and LmjF35.1890) annotated as putative LmL3 and LmL5 proteins were rescued with significant values of BLAST scores. Based on the database sequence data, PCR primers were designed to amplify the LmL3 and LmL5 CR, including cut site for different restriction enzymes for cloning purposes. Amplified DNAs were subcloned in pBluescript and sequenced. The *L. major* putative L3 protein possesses 419 aminoacids having a molecular weight of 47.5 kDa and a predicted isoelectric point of 11.67. *L. major* putative L5 protein possesses 328 aminoacids, with a molecular weight of 36.6 kDa and a predicted isoelectric point of 10.69. Comparison of the *L. major* L3 and L5 deduced aminoacid sequences with their *S. cerevisiae* counterparts revealed a high degree of homology: 57% identity, 73.5% similarity for the L3 protein; 51.2% identity, 66.3% similarity for the L5 protein (See Alignments). The alignment presented herein shows that the *Leishmania* L3 and L5 proteins contain some domains with a high degree of similarity. It was also remarkable to observe that both parasite proteins were longer that the yeast proteins, presenting extra aminoacids residues in the carboxy-terminal end for the LmL3 and in both ends for the LmL5. The unusual primary structure of *Leishmania* proteins belonging to conserved protein families seems to be immunologically relevant, since the humoral and cellular responses elicited against these proteins during infection are specific against the parasite without cross-reactivity with the homologous proteins from the host counterparts (39, 36, 58).

Figure 1:
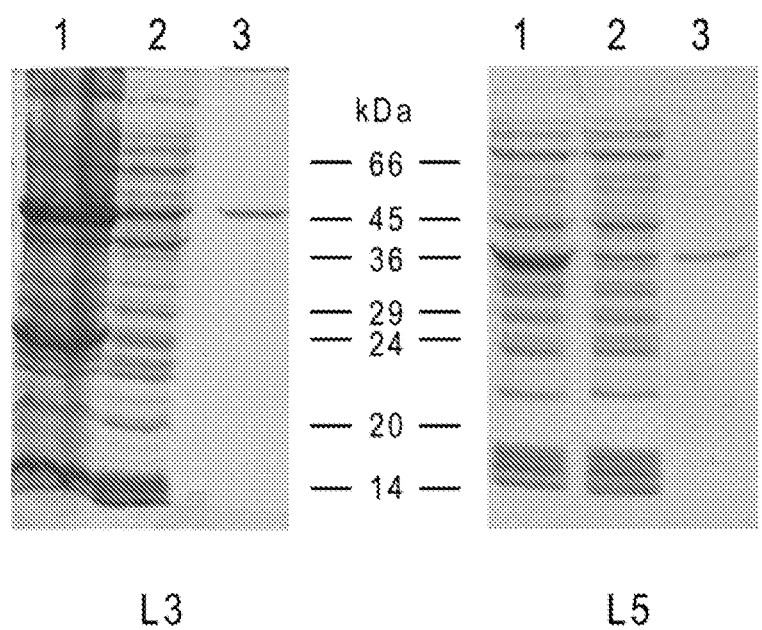
FIG. 1. Expression and purification of recombinant *Leishmania major* rLmL3 and rLmL5 proteins. Coomassie-blue-stained 13% polyacrylamide gels of lysates of pQELmL3 (panel L3) or pQELmL5 (panelL5) vector-transfected *Escherichia coli* lysates after induction (lines 1), after passage by Ni-NTA agarose columns (lines 2) and purified recombinant rLmL3 and rLmL5 (lines 3).

LmL3 and LmL5 CR were subcloned in the pQE30 expression vector. The amino acid sequences of the deduced recombinant proteins are shown in Parts C and D of the alignment. Both proteins present as the N-terminal a tag that includes the 6 histidines used for affinity chromatography purification. Subsequently, both proteins were over-expressed in *E. coli* cultures and purified. As it is shown in FIG. 1, the purified rLmL3 and rLmL5 proteins showed an apparent molecular mass of 48 kDa and 38 kDa, respectively, in accordance with the presence of 12 amino acids extra his-tag stretch on their N-terminal regions. Purity of the protein was demonstrated, since a single band was observed for both purified recombinant protein in a Coomassie blue-stained SDS-PAGE gel (FIG. 1)

LmL3 and LmL5 are Recognized by Canine Visceral Leishmaniasis (CVL) Sera and by Sera from BALB/c Mice Infected with *L. Major* (MCL).

Figure 2A:
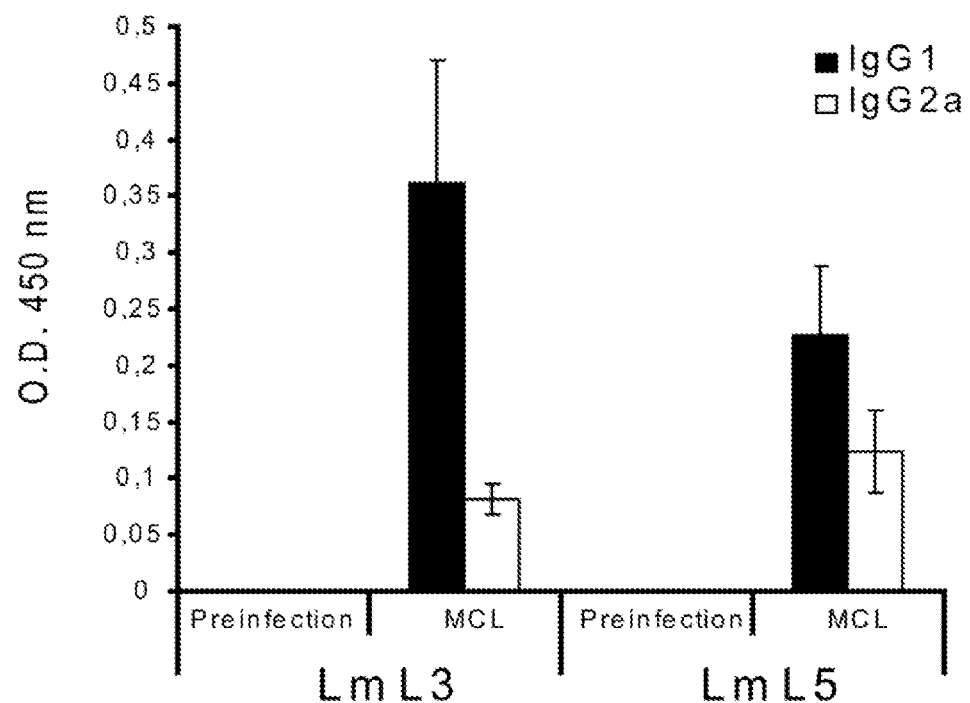
FIG. 2. Antigenicity of the L3 and L5 proteins.
Figure 2B:
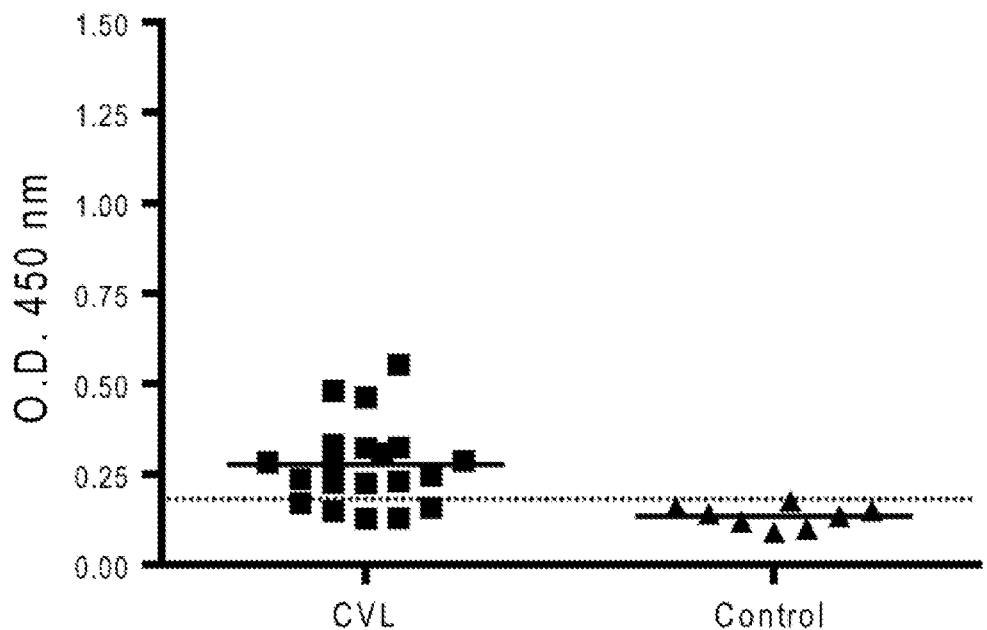
Figure 2C:
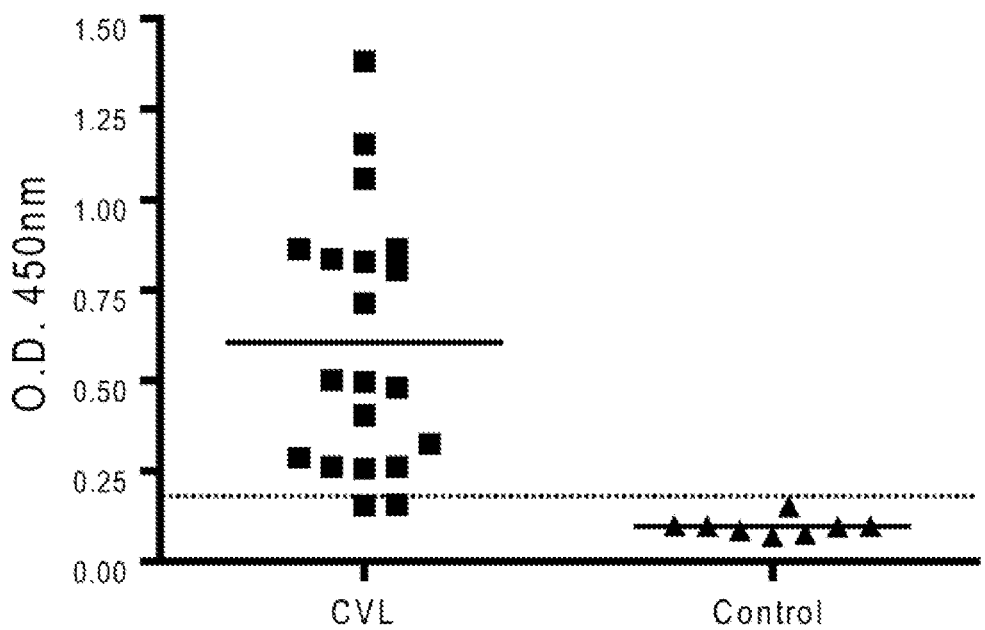

To determine the antigenicity of *L. major* L3 and L5 proteins in dogs affected by VL, the recombinant rLmL3 and rLmL5 proteins were employed as antigens in ELISA assays using the sera from 20 *L. infantum* infected dogs. As control, the reactivity of sera obtained from 8 healthy dogs against both recombinant proteins was assayed. Of the CVL sera 75% (15/20) recognized the rLmL3 protein (FIG. 2b) and 90% (18/20) recognized the rLmL5 protein with reactivity values higher than the cut off value (FIG. 2c). The spectrum of the absorbance values between that against rLmL3 and rLmL5 were different, as the reactivity of CVL sera against rLmL5 was higher (mean=0.61±0.36) than that obtained for rLmL3 (mean=0.28±0.10). It can be concluded that both parasite proteins are exposed to the immune system during canine natural leishmaniasis, being the LmL5 protein a more prevalent immunogen than LmL3. Although a limited number of sera were employed here, the data obtained can be taken as an indication that both recombinant parasite proteins may be used, in combination with other antigens, for the development of serodiagnostic tests of CVL.

Next we analyzed the antigenicity of the LmL3 and LmL5 proteins using the sera from BALB/c mice suffering cutaneous leishmaniosis (MCL) due to the infection of *L. major*. For that purpose, the presence of IgG1 and IgG2a antibodies against both recombinant proteins was analyzed by ELISA. Both proteins were recognized by the MCL sera being the antibodies elicited against them predominantly of the IgG1 isotype (FIG. 2a). No reactivity against them was observed in the same mice before infection (FIG. 2a. Since the induction of IgG1 and IgG2a antibodies is used as a marker of Th2-type and Th1-type immune responses, respectively (8), we may conclude that during *L. major* infection a Th2-like humoral response is induced against these antigens in BALB/c mice.

Immunization with the rLmL3 and rLmL5 Recombinant Ribosomal Proteins in the Presence of CpG ODN Induces a Th1-Type Response Against them in BALB/c Mice.

Figure 3A:
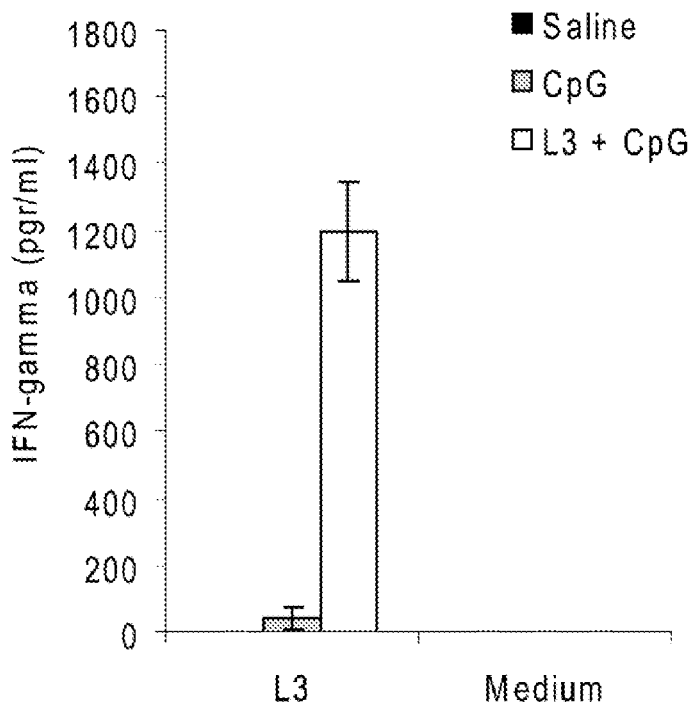
Figure 3B:
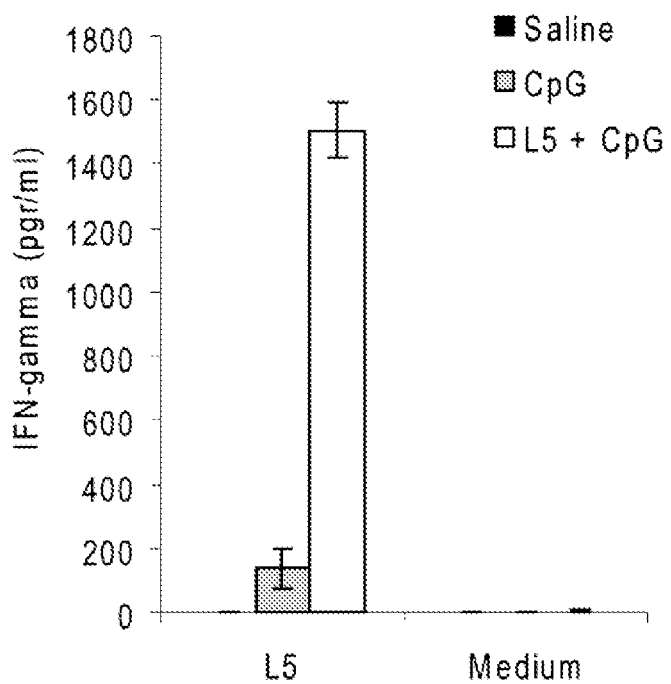
Figure 3C:
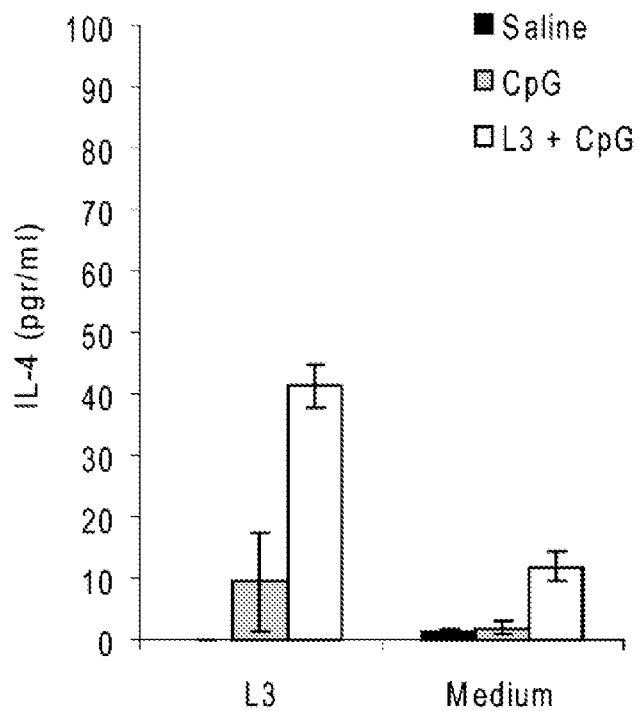
Figure 3D:
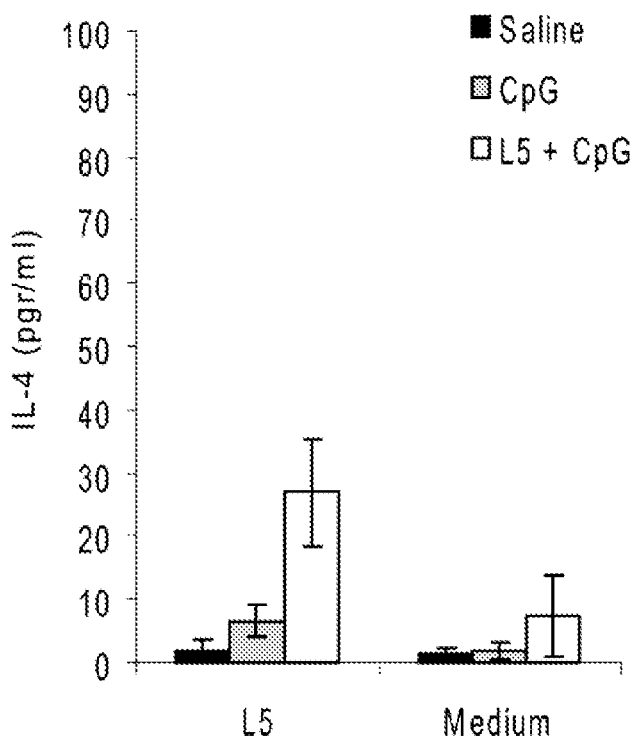
Figure 3E:
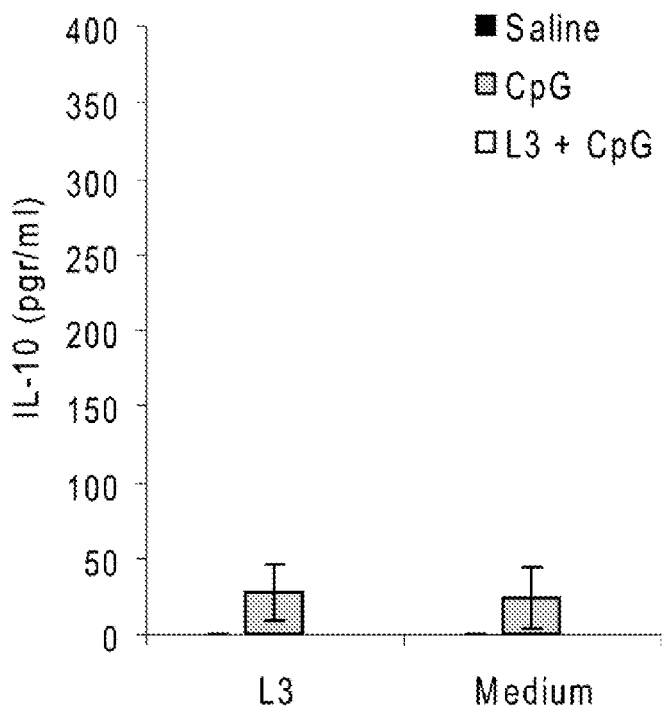
Figure 3F:
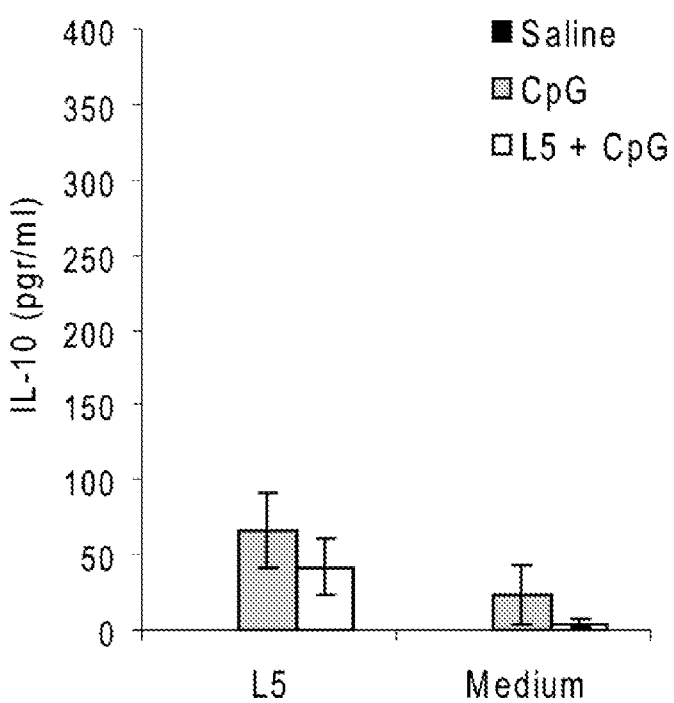

Since a Th2 mediated humoral response against them is elicited in infected BALB/c mice we analyzed the effect of the immunization of rLmL3 and rLmL5 in the presence of a Th1 inducing adjuvant (CpG-ODN). For that purpose groups of six mice were independently immunized with rLmL3 and rLmL5 in combination with CpG-ODN. As control, groups of six mice were immunized with CpG-ODN alone and with PBS (buffer employed as excipient). After three doses the cellular responses brought about by the immunization were analyzed. Spleen cells were obtained and cultured in the presence and in the absence of the corresponding rLmL3 or rLmL5 antigens. Spleen cells from mice immunized with rLmL3+CpG-ODN produced a high level of IFN-gamma after stimulation with the rLmL3 antigen (FIG. 3a). Similar IFN-gamma level was detected in the supernatants of spleen cell cultures from mice immunized with rLmL5+CpG-ODN after rLmL5 stimulation (FIG. 3b). In contrast, spleen cells from mice immunized with the adjuvant or the excipient produced low levels of IFN-gamma in response to rLmL3 or rLmL5 stimulation (FIG. 3ab). With respect to IL-4 production very low levels of this cytokine were detected after rLmL3 or rLmL5 stimulation of spleen cells obtained from mice immunized with rLmL3+CpG-ODN (FIG. 3c) or rLmL5+CpG-ODN (FIG. 4d), respectively. Finally, no IL-10 specific production was detected in any group (FIG. 3ef). Thus, it can be conclude that the CpG-ODN adjuvant skews the immune response against the recombinant antigens toward a Th1 response.

Vaccination with rLmL3+CpG-ODN and rLmL5+CpG-ODN Protects BALB/c Mice Against *L. Major* Challenge.

We analyzed whether the administration of both recombinant proteins was able to induce protection against *L. major* infection in the susceptible BALB/c mice. Footpad swelling of rLmL3+CpG-ODN or rLmL5+CpG-ODN vaccinated mice was significantly lower compared with the footpad swelling of the PBS or CpG-ODN control groups (FIG. 4a). In addition, an approximately 2-log reduction in parasite burden was observed in the draining lymph node cells from the rLmL3+CpG-ODN or rLmL5+CpG-ODN immunized mice. Finally, no parasites could be detected in spleen whereas parasites were detected in spleen of the mice from both control groups (FIG. 3b. It can be concluded that mice immunized with the parasite LmL3 and LmL5 proteins expressed as recombinant proteins mixed with CpG-ODN were protected against a *L. major* infection. In the vaccinated mice dermal pathology was absent or was very low. In these mice the presence of parasites was restricted to the poplyteal draining lymph node. The protection observed was similar to that obtained by the immunization of mice with a plasmid DNA cocktail encoding the nucleosomal histones of *Leishmania* (19), the P0 protein administered as a DNA vaccine (54) and a LRP extracts combined with CpG-ODN (55). Thus, we have characterized two ribosomal constituents whose immunization can contribute to a more rational development of effective molecular defined vaccines against leishmaniasis.

Analysis of the Immunological Parameters Associated with Protection.

Figure 5A:
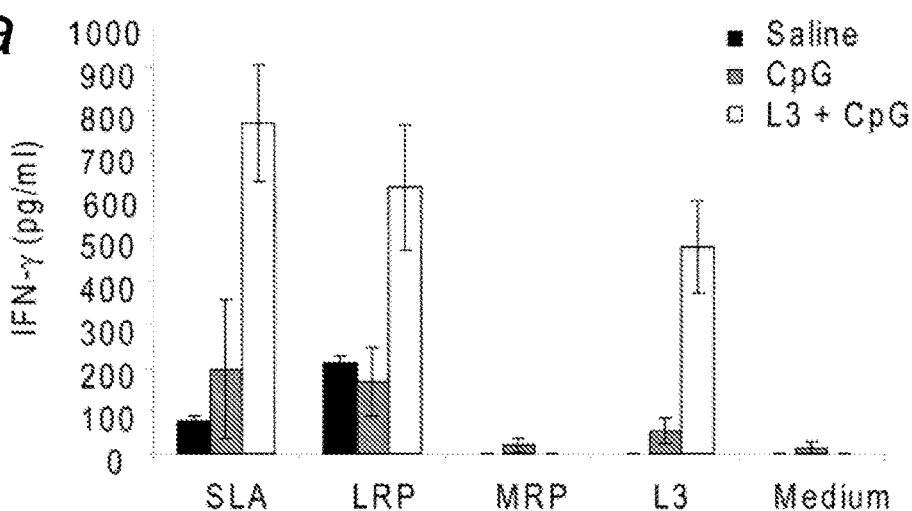
Figure 5B:
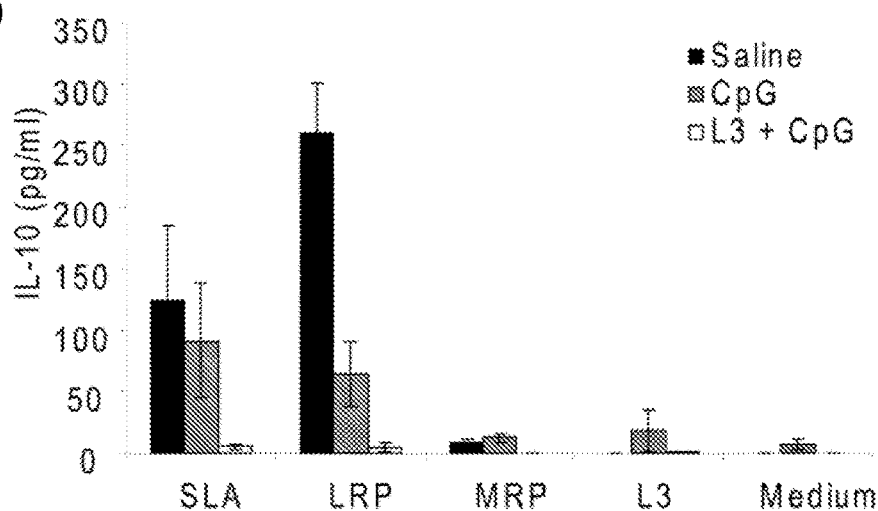
Figure 5C:
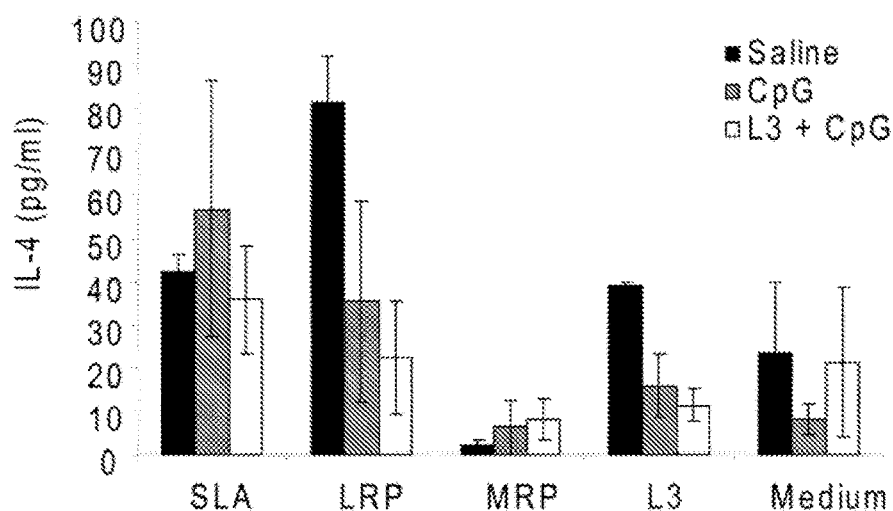
Figure 6A:
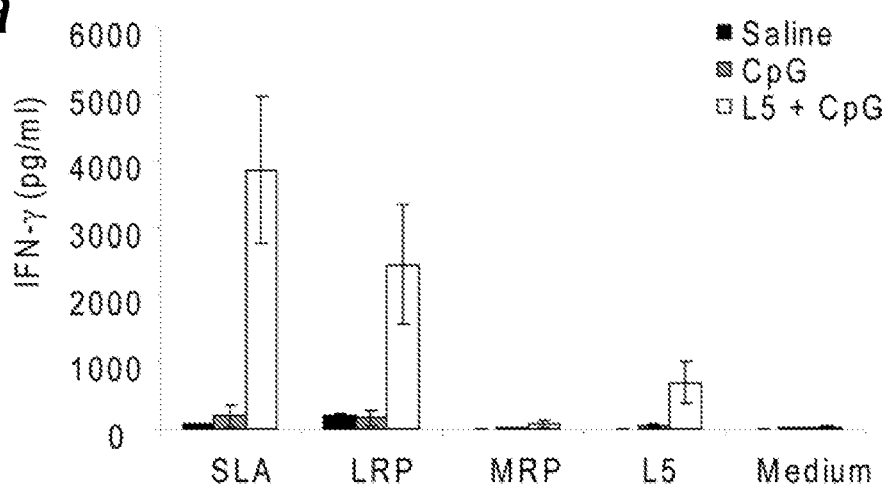
Figure 6B:
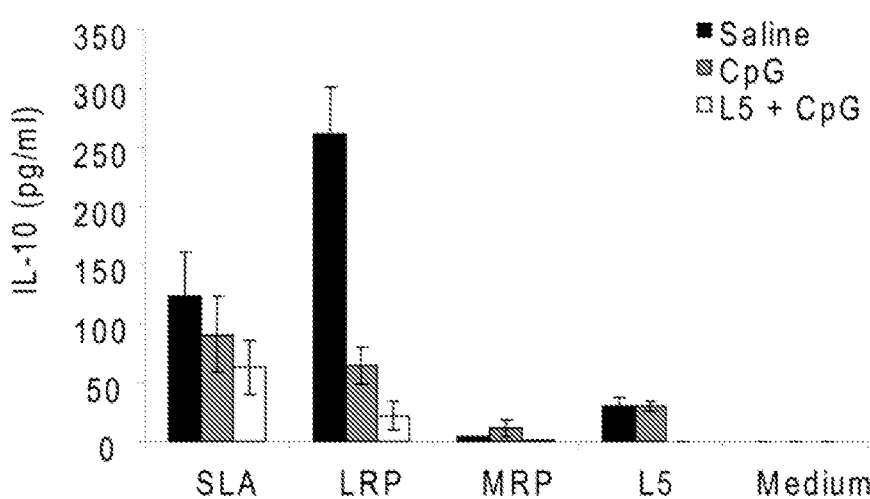
Figure 6C:
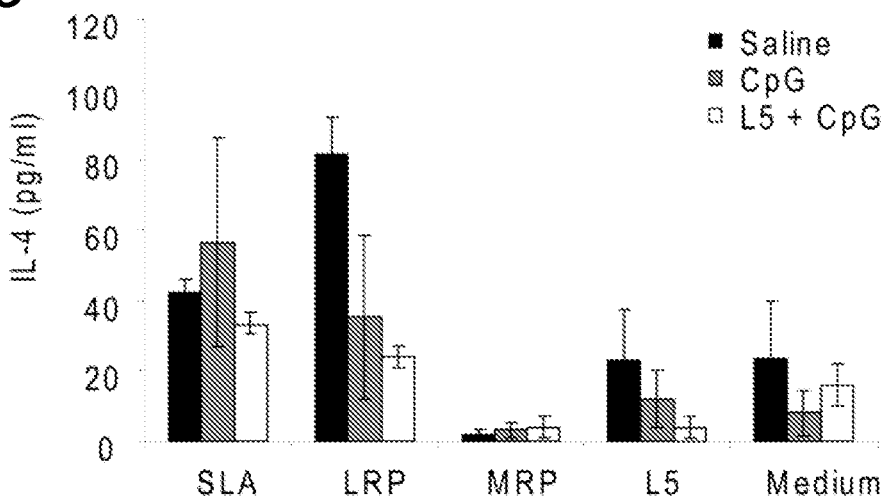

To determine the immunological parameters associated with protection the cytokine production (IFN-γ, IL-4 and IL-10) driven by the SLA, LRP, MRP and the corresponding recombinant protein (L3 and L5) was analyzed in the vaccinated and control mice groups at week 8 after challenge. Spleen cells from L3 and L5 vaccinated mice produced more SLA, LRP and recombinant antigen specific IFN-γ than those from control mice at week eight after challenge (FIG. 5a) for L3 and FIG. 6a for L5). The IFN-γ production was found to be induced specifically by *Leishmania* ribosomal proteins, since stimulation of spleen cell cultures with MRP did not resulted in the production of this cytokine (FIG. 5a for L3 and FIG. 6a for L5). In addition, lower levels of SLA and LRP specific IL-10 (FIG. 5b for L3 and FIG. 6b for L5) and IL-4 (FIG. 5c for L3 and FIG. 6c for L5) were found in the supernatants of spleen cells obtained from protected mice when compared with control mice (CpG and saline). In addition, the MRP-specific L3 and L5 dependent production of IL-10 and IL-4 was very low in the protected mice. Thus, it can be concluded that after infection the protective phenotype was associated with the induction of L3 and L5 Th1 responses that were able to control the IL-4 and IL-10 responses induced by the parasite.

Alignments of LmL3 and LmL5 sequence data. Aminoacid sequence alignments of *Leishmania major* L3 (A) and L5 (B) proteins with their *Saccharomyces cerevisiae* orthologues. Conserved aminoacids are shaded. The number of aminoacids of the LmL3 and LmL5 are indicated. The *L. major* aminoacid sequences were predicted from their corresponding DNA sequences. (C and D) Aminoacid sequences or the predicted aminoacid sequences of the recombinant LmL3 (rLmL3) (C) and LmL5 (rLmL5) (D) proteins expressed in bacteria. The extra his-tag sequence located on their N-terminal is indicated in bold and underlined. The number of aminoacids of the rLmL3 and rLmL5 proteins is indicated

A

```
LmL3  MSHCKFEHPRHGHLGPLPRKRSRQIRGRARAPPKDDATQKPHLTSFMVFKAGMTHIVRDVDRPGSKVNKK
ScL3  MSHRKYEAPRHGHLGPLPRKKAASIRARVKAPPKDDRSKPVALTSFLGYKAGMTTIVRDLDRPGSKFHKR

EVVEPVTILEAPPMVIVGIVGYRQTPVGLKTIGTVWAHHTSVEFRKRYKKNWKQSAQLAFSRQKQFANTK
      EVVEAVTVVDTPPVVVGVVGVVETPRGLRSLTTVWAEHLSDEVKRRFYKNWYKSKKKSFT--KYSAKYA

EGKVAEARTLNAFAKKASVIRVIAHTQLRKLRNHRVGVKKAHVQEIQVNGGSVAAKIALAKSLLEKEVRV
      QDGAGIERELARIKKYASVVRVLVHTQIRKT---PLAQKKAHLAEIQLNGGSISEKVDWAREHFEKTVAV

DSVEQQSEACDVCSVTKGHGTEGVVKEWGVACLPRKTHRGLRKVACIGAWHPARVMYTVARAGQHGYHHR
      DSVEEQNEMIDAIAVTKGHGFEGVTHRWGTKKLPRKTHRGLRKVACIGAWHPAHVMWSVARAGQRGYHSR

TQLNKKIYQIGRSVAVEPNQATTTYDLTAKTITPMGGEVGYGTVRNDYVMLKGSVSGPRRRVMTLRRPMA
      TSINHKIYRVGKG-DDEANGA-TSFDRTKKTITPMGGEVHYGEIKNDFIMVKGCIPGNRKRIVTLRKSLY

PQTSRQLKEKIVLKFIDTSSKISHGRPQTKKEKNQWFGPLKKDRIRREERLRKERAARAVERKAKAAKK
      TNTSRKALEEVSLKWIDTASKFGKGRPQTPAEKHAFMGTLKKDL
```

B

```
LmL5    MCTLANWVRAIIKKHSTLAHTLEMPFVKVVKNKAYFKRFQVKYRRRREGKTDYHARRQMVLQDKTKFGSP
ScL5                    MAFQKDAKSSAYSSRFQTPFRRRREGKTDYYQRKRLVTQHKAKYNTP

KYRLVVRITNKDIIAQIVQAKIVGDEVVMAAYAHELPAFGIEHGLTNYAAAYATGLLLARRTLAKLGIAD
        KYRLVVRFTNKDIICQIISSTITGDVVLAAAYSHELPRYGITHGLTNWAAAYATGLLIARRTLQKLGLDE

KFQGAKEADGSYSAVRTKKDDEGDDEERFPFKAILDVGLARTTTGARVFGVLKGAVDGGMAVPHRPNRFP
        TYKGVEEVEGEYELTEAVEDGPR------PEKVFLDIGLQRTTTGARVFGALKGASDGGLYVPHSENRFP

GYNKEKSSLDAKVHRKRIRGKHVADYLKQVKEEASSNPDEKCVQ-FSKYMAAKVLPESIEGMYKKAHAAI
        GWDFETEEIDPELLRSYIRGGHVSQYM----EELADDDEERFSELFKGYLADDIDADSLEDIYTSAHEAI

RADPS-KSLPKKAKKEGVA--HKSYKTKKLSGAEKRAAAKAKVAAIRERLGK
        RADPAFKPTEKKFTKEQYAAESKKYRQTKLSKEERAARVAAKIAAL
```

C

```
rLmL3   MRGSHHHHHHGSMSHCKFEHPRHGHLGFLPRKRSRQIRGRARAFPKDDATQKPHLTSFMV      60
        FKAGMTHIVRDVDRPGSKVNKKEVVEPVTILEAPPMVIVGIVGYRQTPVGLKTIGTVWAH     120
        HTSVEFRRRYYKNWKQSAQLAFSRQKQFANTKEGKVAEARTLNAFAKKASVIRVIAHTQL     180
        RKLRNHRVGVKKAHVQEIQVNGGSVAAKIALAKSLLEKEVRVDSVFQQSEACDVCSVTKG     240
        HGTEGVVKRWGVACLPRKTHRGLRKVACIGAWHPARVMYTVARAGQHGYHHRTQLNKKIY     300
        QIGRSVAVEPNQATTTYDLTAKTITPMGGFVGYGTVRNDYVMLKGSVSGPRRRVMTLRRP     360
        MAPQTSRQLKEKIVLKFIDTSSKIGHGRFQTKKEKNQWFGPLKKDRIRREERLRKERAAR     420
        AVERKAKAAKK                                                     431
```

D

```
rLmL5   MRGSHHHHHHGSMCTLANWVRAIIKKHSTLAHTLEMPFVKVVKNKAYFKRFQVKYRRRRE      60
        GKTDYHARRQMVLQDKTKFGSPKYRLVVRITNKDIIAQIVQAKIVGDEVVMAAYAHELPA     120
        FGIEHGLTNYAAAYATGLLLARRTLAKLGIADKFQGAKEADGSYSAVRTKKDDEGDDEER     180
        FPFKAILDVGLARTTTGARVFGVLKGAVDGGMAVPHRPNRFPGYNKEKSSLDAKVHRDRI     240
        FGKHVADYLKQVKEEASSNPDEKCVQFSKYMAAKVLPESIEGMYKKAHAAIRADPSKSLP     300
        KKAKKEGVAHKSYKTKKLSGAEKRAAAKAKVAAIRERLGK                        340
```

Example 2

Analysis of L3 and L5 Homologues

Alignment of L3 and L5 Homologues

We have analyzed the degree of conservation of L3 and L5 ribosomal proteins between different *Leishmania* species. For that purpose, the amino acid sequences of the L3 protein from *L. infantum*, and *L. mexicana* (SEQ ID NO:48 and 50) and the L5 protein from *L. infantum* (clone JPCM5 [MCAN/ES/98/LLM-877]), *L. braziliensis* (MHOM/BR/75/M2904) and *L. mexicana* (MHOM/GT/2001/U1103) (SEQ ID NO: 52, 56 and 54) were rescued by an in silico analysis from the genome database (www.genedb.org) and compared with the amino acid sequences from *L. major* orthologues (SEQ ID NO:1 for L3 and SEQ ID NO:3 for L5) (confere alignments at next page, part A and B). Except for the existence of an N-terminal extension in the *L. major* L5 protein, a high degree of conservation was observed between the different species. Table 1A-B shows the percentages of identity and similarity between the L3 and L5 orthologues, respectively.

Location of the *Leishmania Major* L3 and L5 in the Ribosomes.

Figure 8A:
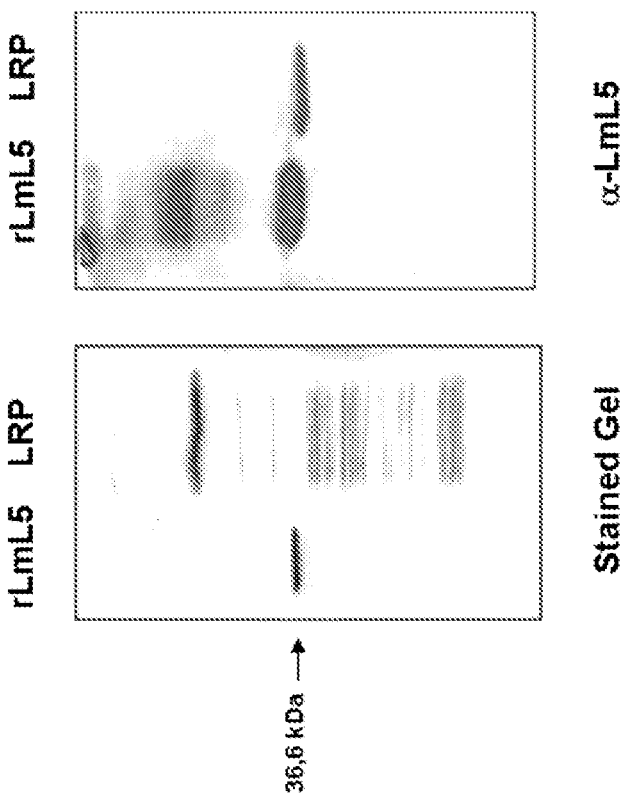
Figure 8B:
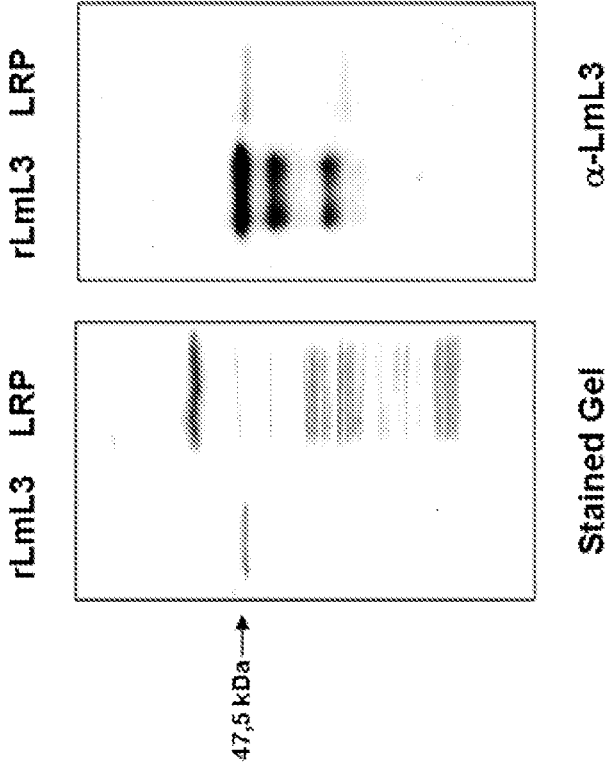

In order to demonstrate that the recombinant LmL3 and LmL5 employed in this work correspond to the proteins located in the parasite ribosomes we have employed antibodies specific for the recombinant proteins in western blot containing the recombinant proteins and LRP extracts. FIG. 8A shows that anti-LmL3 antibodies obtained from mice immunized with the recombinant protein recognized a single band with the expected molecular weight (47.5 kDa) in the LRP extracts. Similar result was observed for the L5 protein (FIG. 8B). A single band of 36.6 kDa was observed in the LRP extracts when we employed anti-LmL5 antibodies purified from *L. infantum* naturally infected dogs sera by affinity chromatography in a rLmL5-Shepharose 4B column as previously described (71). As a positive control, in both cases, the corresponding recombinant protein was recognized by the specific antibodies.

*Leishmania* L3 and L5 sequence comparisons. Aminoacid sequence alignments of *L. major, L. infantum* and *L. mexicana* L3 (A) (SEQ ID NO: 1, 48 and 50) and *L. major, L. braziliensis, L. infantum* and *L. mexicana* L5 (B) (SEQ ID NO: 3, 56, 52 and 54). The LmL3 protein, the putative L3 protein sequences of *L. infantum* (GeneDB identifier LinJ32_V3.3320) and *L. mexicana* (GeneDB identifier LmxM33.2900), and the LmL5 protein and the putative L5 protein sequences of *L. braziliensis* (GeneDB identifier LbrM34_V2.1790), *L. infantum* (GeneDB identifier LinJ35_V3.1870) and *L. mexicana* (GeneDB identifier LmxM34.1880) were aligned using the default settings of ClustalW (DNAstar program). Aminoacids substitutions are shaded.

A

| | |
|---|---|
| L. major | MSHCKFEHPRHGHLGFLPRKRSRQIRGRARAFPKDDATQKPHLTSFMVF |
| L. infantum | MSHCKFEHPRHGHLGFLPRKRSRQIRGRARAFPKDDATQKPHLTSFMVF |
| L. mexicana | MSHCKFEHPRHGHLGFLPRKRSRQIRGRARAFPKDDATQKPHLTSFMVF |
| | |
| L. major | KAGMTHIVRDVDRPGSKVNKKEVVEPVTILEAPPMVIVGIVGYRQTPVGL |
| L. infantum | KAGMTHIVRDVDRPGSKVNKKEVVEPVTILEAPPMVIVGIVGYRQTPVGL |
| L. mexicana | KAGMTHIVRDVDRPGSKVNKKEVVEPVTILEAPPMVIVGIVGYRQTPVGL |
| | |
| L. major | KTIGTVWAHHTSVEFRRRYYKNWKQSAQLAFSRQKQFANTKEGKVAEART |
| L. infantum | KTIGTVWAHHTSVEFRRRYYKNWKQSAQLAFSRQKQFANTKEGKVAEART |
| L. mexicana | KTIGTVWAHHTSVEFRRRYYKNWKQSAQLAFSRQKQFANTKEGRIAEART |
| | |
| L. major | LNAFAKKASVIRVIAHTQLRKLRNHRVGVKKAHVQEIQVNGGSVAAKIAL |
| L. infantum | LNAFAKKASVIRVIAHTQLRKLRNHRVGVKKAHVQEIQVNGGSVAAKIAL |
| L. mexicana | LNAFAKKASVIRVIAHTQLRKLRNHRVGVKKAHVQEIQINGGNVAAKIAL |
| | |
| L. major | AKSLLEKEVRVDSVFQQSEACDVCSVTKGHGTEGVVKRWGVACLPRKTHR |
| L. infantum | AKSLLEKEVRVDSVFQQSEACDVCSVTKGHGTEGVVKRWGVACLPRKTHR |
| L. mexicana | AKSLLEKEVRVDSVFQQSEACDVCSVTKGHGTEGVVKRWGVACLPRKTHR |
| | |
| L. major | GLRKVACIGAWHPARVMYTVARAGQHGYHHRTQLNKKIYQIGRSVAVEPN |
| L. infantum | GLRKVACIGAWHPARVMYTVARAGQHGYHHRTQLNKKIYQIGRSVAVEPN |
| L. mexicana | GLRKVACIGAWHPARVMYTVARAGQHGYHHRTQLNKKIYQIGRSVAVEPN |
| | |
| L. major | QATTTYDLTAKTITPMGGFVGYGTVRNDYVMLKGSVSGPRRRVMTLRRPM |
| L. infantum | QATTTYDLTAKTITPMGGFVGYGTVRNDYVMLKGSVSGPRRRVMTLRRPM |
| L. mexicana | QATTTYDLTAKTITPMGGFVGYGTVRNDYVMLKGSVSGPRRRVMTLRRPM |
| | |
| L. major | APQTSRQLKEKIVLKFIDTSSKIGHGRFQTKKEKNQWFGPLKKDRIRREE |
| L. infantum | APQTSRHLKEKIVLKFIDTSSKIGHGRFQTKKEKNQWFGPLKKDRIRREE |
| L. mexicana | APQTSRQLKEKIVLKFIDTSSKIGHGRFQTKKEKSQWFGPLKKDRIRREE |
| | |
| L. major | RLRKERAARAVERKAKAAKK |
| L. infantum | RLRKERAARAVERKAKVAKK |
| L. mexicana | RLRKERAARAVERKAKAAKK |

B

| | |
|---|---|
| L. major | ~~MCTLANWVRAIIKKHSTLAHTLE~~MPFVKVVKNK |
| L. braziliensis | MPFVKVVKNK |
| L. infantum | MPFVKVVKNK |
| L. mexicana | MPFVKVVKNK |
| | |
| L. major | AYFKRFQVKYRRRREGKTDYHARRQMVLQDKTKFGSPKYRLVVRITNKDI |
| L. braziliensis | AYFKRFQVKYRRRREGKTDYHARRQMVLQDKTKFGSPKYRLVVRTTNKDI |
| L. infantum | AYFKRFQVKYRRRREGKTDYHARRQMVLQDKTKFGSPKYRLVVRITNKDI |
| L. mexicana | AYFKRFQVKYRRRREGKTDYHARRQMVLQDKTKFGSPKYRLVVRITNKDI |
| | |
| L. major | IAQIVQAKIVGDEVVMAAYAHELPAFGIEHGLTNYAAAYATGLLLARRTL |
| L. braziliensis | IAQIVQAKIAGDEVLMAAYAHELPAFGIEHGLTNYAAAYATGLLLARRTL |
| L. infantum | IAQIVQAKIVGDEVVMAAYAHELPAFGIEHGLTNYAAAYATGLLLARRTL |
| L. mexicana | IAQIVQAKIVGDEVVMAAYAHELPAFGIEHGLTNYAAAYATGLLLARRTL |
| | |
| L. major | AKLGIADKFQGAKEADGSYSAVRTKKDDEGDDEERFPFKAILDVGLARTT |
| L. braziliensis | AKLGIADKFQGAKEADGSYSAVRTKKDDQGDDEARFPFKAILDVGLARTT |
| L. infantum | AKLGIADKFQGAKEADGSYSAVRTKKDDEGDDEERFPFKAILDVGLARTT |
| L. mexicana | AKLGIADKFQGAKEADGSYSAVRTKKDDEGDDEERFPFKAILDVGLARTT |
| | |
| L. major | ADYLKQVKEEASSNPDEKCVQFSKYMAAKVLPESIEGMYKKAHAAIRADP |
| L. braziliensis | AEYLKQVKEEASSNPDEKCVQFSKYMEAKVAPESIECMYKKAHAAIRADP |
| L. infantum | AEYLKQVKEEASSNPDEKCVQFSRYMAAKVLPESIEGMYKKAHAAIRADP |
| L. mexicana | AEYLKQVKEEASSNPDEKCVQFSKYMAAKVLPESIEGMYKKAHAAIRADP |
| | |
| L. major | SKSLPKKAKKEGVAHKSYKTKKLSGAEKRAAAKAKVAAIRERLGK |
| L. braziliensis | SKSLPKKAKKEGAKHKSYKTKKMSGAEKRAAAKAKVAAIRERLGK |
| L. infantum | SKSLPKKAKKEGVAHKSYKTKKLSGAEKRAAAKAKVAAIRERLGK |
| L. mexicana | SKSLPKKAKKEGVAHKSYKTKKLSGAEKRAAAKAKVAAIRERLGK |

TABLE 1

A
LmL3

|  | L. major | L. infantum | L. mexicana |
|---|---|---|---|
| L. major | 100.0% (100.0%) | 99.5% (99.5%) | 98.6% (99.5%) |
| L. infantum |  | 100.0% (100.0%) | 98.1% (99.0%) |
| L. mexicana |  |  | 100.0% (100.0%) |

B
LmL5

|  | L. major | L. infantum | L. braziliensis | L. mexicana |
|---|---|---|---|---|
| L. major | 100.0% (100.0%) | 99.3% (100.0%) | 94.8% (97.4%) | 99.3% (99.7%) |
| L. infantum |  | 100.0% (100.0%) | 94.8% (97.4%) | 99.3% (99.7%) |
| L. braziliensis |  |  | 100.0% (100.0%) | 94.8% (97.0%) |
| L. mexicana |  |  |  | 100.0% (100.0%) |

The identity and similarity values (between brackets) are shown.

Example 3

Figure 7A:
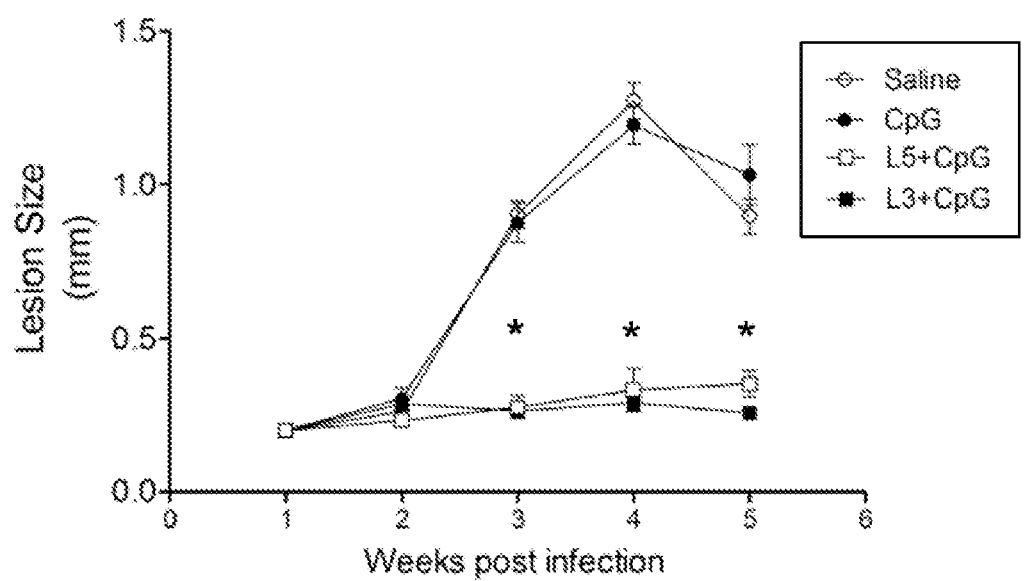
Figure 7B:
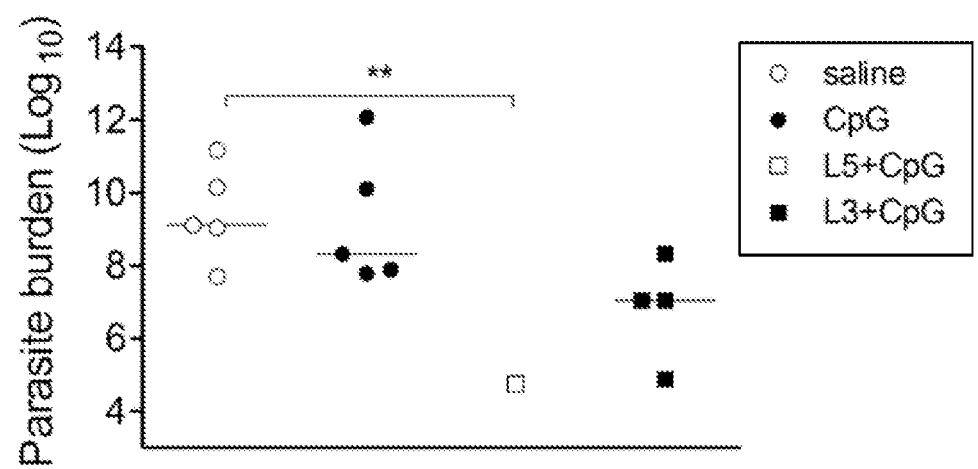

Vaccination with rLmL3+CpG-ODN and rLmL5+CpG-ODN Protects BALB/c Mice Against L. Braziliensis Challenge We have analyzed the effect of the immunization of the L. major recombinant proteins rLmL3 and rLmL5 combined with a Th1 inducing adjuvant (CpG-ODN) in the development of cutaneous leishmaniasis caused by infection with L. braziliensis. For that purpose groups of five mice were independently immunized with 10 µg of rLmL3 or 10 µg of rLmL5 in combination with 50 µg of CpG-ODN (25 µg of CpG-1 [5'-TCAACGTTGA-3']plus 25 µg of CpG-2 [5'-GCTAGCGTTAGCGT-3']) (SEQ ID NO:5 and 6)). As control, groups of five mice were immunized with 50 µg of CpG-ODN alone or with PBS (buffer employed as excipient). Mice were inoculated in the ear dermis (left ear). Each group was boosted two and four weeks later with the same dose used for priming. Parasite challenge was carried out by injection in the right (untreated) ear with $10^5$ stationary promastigotes of L. braziliensis (MHOM/BR/01/BA788) combined with two pairs of Lutzomya intermedia sand fly salivary glands. In this model of infection, after parasite challenge BALB/c mice develop inflammatory lesion in the infected ears that progressed steadily and reached a maximum of approximately at week 5. Thereafter, lesion size regressed and complete ear scarring was observed approximately at week 9 post-infection (72). We have analyzed the development of cutaneous lesion in the four mice groups up to 5 weeks after parasite challenge measuring the lesion thickness with a metric caliper. As it is shown in FIG. 7A, ear lesions of rLmL3+CpG-ODN or rLmL5+CpG-ODN vaccinated mice were significantly lower compared with PBS on CpG-ODN control groups. In addition, parasite burdens were analyzed at week 5 after infection in the infected ears. The number of parasites was determined by limiting dilution assay as described (73). A decrease in the parasite burdens were observed in vaccinated mice when compared with control groups. Differences were found to be significant in the rLmL5+CpG-ODN group with respect to both control groups (P<0.05, T-student test). Moreover, no parasites could be detected in the ear in four of five mice (rLmL5+CpG-ODN group) and one of five mice in the rLmL3+CpG-ODN group (FIG. 7B). Thus, it was concluded that mice vaccinated with the L. major L3 and L5 ribosomal proteins expressed as recombinant proteins and combined with CpG-ODN were protected against a heterologous challenge with L. braziliensis.

Example 4

Figure 9B:
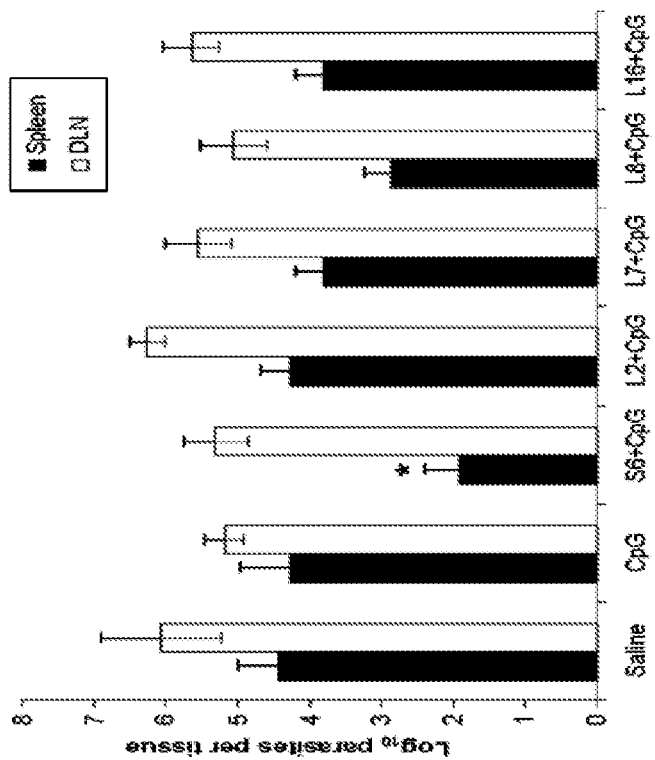
Figure 9A:
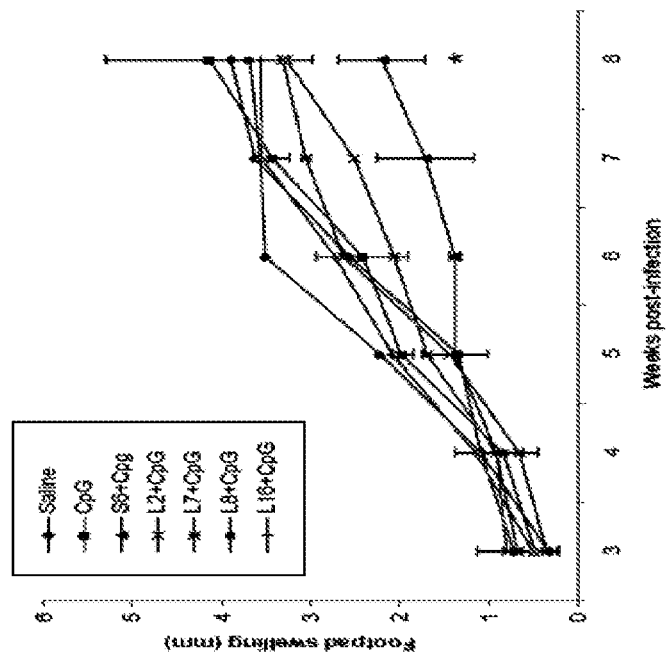

Partial Protection Conferred by Leishmania Major S6 Against Leishmania Major Infection Five mice groups (n=4 per group) were independently immunized with 10 µg of S6 (SEQ ID NO: 34), L2 (SEQ ID NO: 22), L7 (SEQ ID NO: 24), L8 (SEQ ID NO: 26) and L16 (SEQ ID NO: 28) in the presence of CpG ODN as identified earlier by SEQ ID NO:5 and 6 (50 µg). As control, a group of mice was immunized with the adjuvant and other group was immunized with the excipient (PBS-saline). Three doses were administered with 2-week intervals. All immunizations were performed in the right footpad. One month after the last dosis, mice were infected with $10^5$ stationary-phase promastigotes of L. major injected subcutaneously in the left footpad. The development of dermal lesion was evaluated by measuring footpad swelling until week eight post-challenge (FIG. 9A). Mice from all groups developed inflammatory lesions, although the footpad swelling from mice that were vaccinated with S6 plus CpG ODN was significantly lower to that observed in controls and in mice immunized with the other four proteins. Also, parasite burdens in the draining lymph nodes (DLN) and in the spleens of the mice were analyzed. Animals immunized with S6 plus CpG ODN showed a 2-log reduction in the number of parasites in spleen as compared with saline and CpG ODN groups, respectively (FIG. 9B). However, the parasite burdens found in the DLN of the S6 plus CpG ODN group were similar to that observed in controls. From this assay, it can be concluded that the vaccination with the S6 recombinant protein in the presence of CpG ODN adjuvant was inducing an immune state that result in a partial protection against CL due by L. major infection in the BALB/c mice: presence of lower inflammatory lesions in the site of infection and lower parasite burdens in the spleen than controls. On the other hand, vaccination with the other four antigens (L5, L7, L8 and L16) did not result in significant changes in the CL progression relative to controls.

Figure 10B:
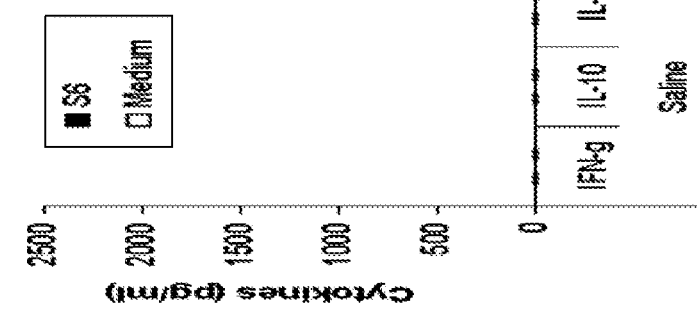
Figure 10A:
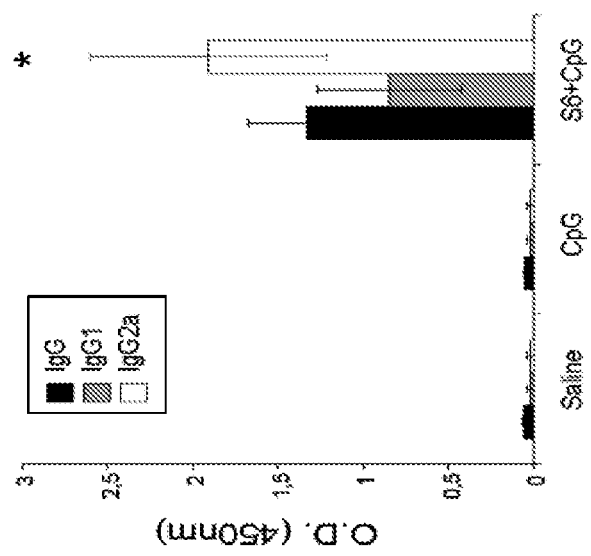

In order to analyze the immune response induced by vaccination, the humoral and cellular responses elicited in mice by vaccination with S6+CpG ODN were compared with mice immunized with the adjuvant and the vaccine diluent. FIG. 10 shows that the vaccine formulation was inducing a Th1/Th2 mixed response against the S6 protein, since anti-S6 specific IgG2a and IgG1 antibodies were detected in the sera of the vaccinated mice (see FIG. 10A). In addition, although IFNgamma was produced after S6 in vitro stimulation of spleen cells established from the vaccinated mice the presence of detectable IL-4 cytokine was also observed in the culture supernatants (see FIG. 10B).

It can be concluded that vaccination induced a predominant Th1 response against the S6 protein, but also a slightly stimulation of a Th2 response against the protein was observed (detectable levels of S6-specific IL-4 and S6-specific IgG1 antibodies).

Example 5

Vaccines Based on L3, L5 and S4 *Leishmania Major* Recombinant Proteins

In order to analyze in more detail the protection induce by the L3, L5 and S4 ribosomal proteins a new immunization-infection experiment was performed. Twelve groups of mice (n=4 per group) were included in the analysis. In all cases mice were immunized subcutaneously three times (two weeks apart) in the right footpad. The next groups were assayed:

Vaccine excipient: saline.
Vaccine adjuvant: CpG-ODN. Per dosis: 50 µg of CpG ODN (25 µg CpG-ODN-1 [5'-TCAACGTTGA-3'] (SEQ ID NO:5) and 25 µg of CpG-ODN-2 [5'-GCTAGCGTTAGCGT-3'] (SEQ ID NO:6).
L3 (SEQ ID NO:1). Per dosis: 10 µg of recombinant protein.
L3+CpG ODN. Per dosis. 10 µg of recombinant protein and 50 µg of CpG ODN.
L5 (SEQ ID NO:3). Per dosis: 10 µg of recombinant protein.
L5+CpG ODN. Per dosis. 10 µg of recombinant protein and 50 µg of CpG ODN.
S4 (SEQ ID NO: 32). Per dosis: 10 µg of recombinant protein.
S4+CpG ODN. Per dosis. 10 µg of recombinant protein and 50 µg of CpG ODN.
L3+L5. Per dosis: 10 µg total recombinant proteins; 5 µg each protein.
L3+L5+CpG ODN. Per dosis. 10 µg of total recombinant protein and 50 µg of CpG ODN.
L3+L5+S4. Per dosis: 10 µg total recombinant proteins; 3.3 µg each protein.
L3+L5+S4+CpG ODN. Per dosis. 10 µg of total recombinant protein and 50 µg of CpG ODN.

Briefly, the three antigens were assayed in the presence or in the absence of CpG ODN. In addition, combinations of L3+L5 and L3+L5+S4 were analyzed in the presence and in the absence of CpG ODN. One month after the last dosis, mice were infected with $10^5$ stationary-phase promastigotes of *L. major* injected subcutaneously in the left footpad.

The development of dermal lesion was evaluated by measuring footpad swelling until week six post-challenge. In the FIG. 11A both control groups (saline and CpG ODN) and the five groups vaccinated with the antigens without the adjuvant is shown. No differences were observed in the inflammatory lesions between control groups and the five mice groups vaccinated with the proteins in the absence of adjuvant. In the FIG. 11B both control groups (saline and CpG ODN) and the five groups vaccinated with the antigens combined with the adjuvant is shown. In this case, all mice groups vaccinated with the recombinant proteins in the presence of the adjuvant showed a reduction in the footpad swelling except the S4+CpG ODN group. The lower inflammatory lesions were observed in the L5+CpG ODN, L3+L5+CpG ODN and L3+L5+S4+CpG ODN groups.

Figure 12A:
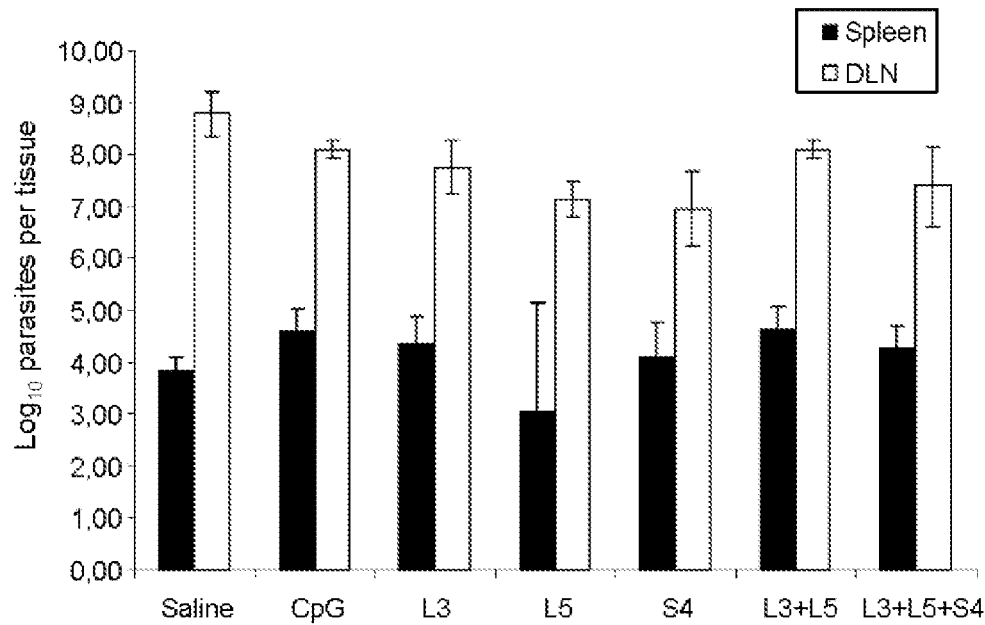
Figure 12B:
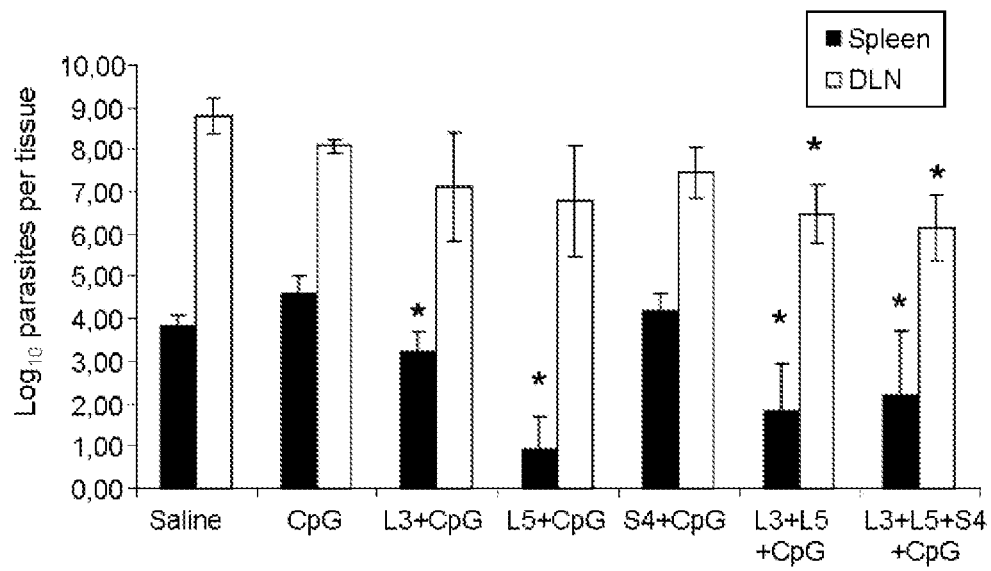

Parasite burdens in the DLN and in the spleens of all mice groups were analyzed at week seven after infection. No statistical differences were found between mice included in the control groups and mice immunized with the ribosomal proteins without adjuvant (FIG. 12A). On the other hand, mice immunized with the ribosomal proteins plus CpG ODN showed a significant decrease in the parasite burdens in spleen, except in the S4 plus CpG ODN group (FIG. 12B). Regarding the parasite loads in the in the popliteal lymph node, we only found a significant decrease in groups that were vaccinated with the combination of two (L3+L5) or three (L3+L5+S4) ribosomal proteins plus CpG ODN. Mice vaccinated with L3 plus CpG ODN and L5 plus CpG ODN also showed lower parasite burdens than controls. However, due to the high degree of variability found between the different animals, results were not statistically significant. These assays should be repeated with a higher number of mice in order to analyze the influence of the vaccines in the local parasite burdens, since in previous assays, we found statistical differences between mice vaccinated with L3 plus CpG ODN and L5 plus CpG ODN and controls.

Regarding the use of vaccines based in individual antigens or co-administration of different antigens, our results indicate that the combinatory vaccines are inducing a higher protection degree than vaccines composed on individual antigens.

Example 6

Design of Cloning Procedures for the Construction of Recombinant Molecules Combining the Four Already Characterized Protective Ribosomal Antigens (L3, L5, S4 and S6 from *Leishmania Major*)

Based on previous results, we have planned to prepare new recombinant products based on *Leishmania major* L3 (SEQ ID NO:1), L5 (SEQ ID NO:3), S4 (SEQ ID NO: 32) and S6 (SEQ ID NO:34) proteins.

First, the DNA inserts coding for the four proteins will be cloned in a eukaryotic expression vector (pcDNA-3; Stratagene). This vector, that allows the expression of the *Leishmania* proteins in mammalian cells, can be employed for testing DNA vaccines. Second, we have designed a procedure for cloning different chimerical proteins with different combination of the four antigens (FIG. 13). The gene chimeras will be first cloned in pBluescript (an analysis plasmid) and afterwards the DNA inserts will be cloned in two different expression plasmids:

- pQE30; a prokaryotic expression plasmid.
- pcDNA3, a eukaryotic expression plasmid.

This cloning strategy will allow us to have both, DNA vaccines and recombinant proteins expressed in *E. coli*, with the proposed antigenic combinations.

The following primers were used:

```
LmL3
                                     (SEQ ID NO: 57)
Forward 5'-CGGGATCCATGTCTCACTGCAAGTTCGAG-3'

(SEQ ID NO: 58)
Reverse 5'-GCGATATCTCCCTTCTTCGCGGCCTTTGCC-3'

LmS4
                                     (SEQ ID NO: 59)
Forward 5'-GCGATATCGGGATGGCCAAGAAGCACCTCAAG-3'

(SEQ ID NO: 60)
Reverse 5'-CGGAATTCTCCCTTGCGGGCCCTGCGGG-3'

LmS6
                                     (SEQ ID NO: 61)
Forward 5'-CGGAATTCGGGATGAAGCTCAACATCGCGTAC-3'

(SEQ ID NO: 62)
Reverse 5'-GCGATATCTCCCTTCTTCTGGAATGCTGCCAC-3'

LmL5
                                     (SEQ ID NO: 63)
Forward 5'-GCGATATCGGGATGTGCACGCTGGCAAATTG3'

(SEQ ID NO: 64)
Reverse 5'-GGGGTACCGGATCCTTACTTGCCGAGGCGCTCGC-3'
```

The resulting chimeric protein is represented by an amino acid sequence consisting of SEQ ID NO:67. This chimeric protein is encoded by a nucleic acid represented by a nucleic acid molecule consisting of SEQ ID NO:66.

REFERENCES

1. Aguilar-Be, I., R. da Silva Zardo, E. Paraguai de Souza, G. P. Borja-Cabrera, M. Rosado-Vallado, M. Mut-Martin, R. Garcia-Miss Mdel, C. B. Palatnik de Sousa, and E. Dumonteil. 2005. Cross-protective efficacy of a prophylactic *Leishmania donovani* DNA vaccine against visceral and cutaneous murine leishmaniasis. Infect Immun 73:812-9.
2. Anderson, C. F., M. Oukka, V. J. Kuchroo, and D. Sacks. 2007. CD4(+)CD25(−)Foxp3(−) Th1 cells are the source of IL-10-mediated immune suppression in chronic cutaneous leishmaniasis. J Exp Med 204:285-97.
3. Badaro, R., D. Benson, M. C. Eulalio, M. Freire, S. Cunha, E. M. Netto, D. Pedral-Sampaio, C. Madureira, J. M. Burns, R. L. Houghton, J. R. David, and S. G. Reed. 1996. rK39: a cloned antigen of *Leishmania chagasi* that predicts active visceral leishmaniasis. J Infect Dis 173: 758-61.
4. Belkaid, Y., K. F. Hoffmann, S. Mendez, S. Kamhawi, M. C. Udey, T. A. Wynn, and D. L. Sacks. 2001. The role of interleukin (IL)-10 in the persistence of *Leishmania major* in the skin after healing and the therapeutic potential of antiIL-10 receptor antibody for sterile cure. J Exp Med 194:1497-506.
5. Belkaid, Y., S. Kamhawi, G. Modi, J. Valenzuela, N. Noben-Trauth, E. Rowton, J. Ribeiro, and D. L. Sacks. 1998. Development of a natural model of cutaneous leishmaniasis: powerful effects of vector saliva and saliva preexposure on the long-term outcome of *Leishmania major* infection in the mouse ear dermis. J Exp Med 188:1941-53.
6. Buffet, P. A., A. Sulahian, Y. J. Garin, N. Nassar, and F. Derouin. 1995. Culture microtitration: a sensitive method for quantifying *Leishmania infantum* in tissues of infected mice. Antimicrob Agents Chemother 39:2167-8.
7. Campos-Neto, A. 2005. What about Th1/Th2 in cutaneous leishmaniasis vaccine discovery? Braz J Med Biol Res 38:979-84.
8. Coffman, R. L. 1993. Mechanisms of helper T-cell regulation of B-cell activity. Ann N Y Acad Sci 681:25-8.
9. Coler, R. N., and S. G. Reed. 2005. Second-generation vaccines against leishmaniasis. Trends Parasitol 21:244-9.
10. Cordeiro-Da-Silva, A., M. C. Borges, E. Guilvard, and A. Ouaissi. 2001. Dual role of the *Leishmania major* ribosomal protein S3a homologue in regulation of T- and B-cell activation. Infect Immun 69:6588-96.
11. Chenik, M., H. Louzir, H. Ksontini, A. Dilou, I. Abdmouleh, and K. Dellagi. 2006. Vaccination with the divergent portion of the protein histone H2B of *Leishmania* protects susceptible BALB/c mice against a virulent challenge with *Leishmania major*. Vaccine 24:2521-9.
12. Chiaramonte, M. G., M. Hesse, A. W. Cheever, and T. A. Wynn. 2000. CpG oligonucleotides can prophylactically immunize against Th2-mediated schistosome egg-induced pathology by an IL-12-independent mechanism. J Immunol 164:973-85.
13. Garcia-Alonso, M., A. Blanco, D. Reina, F. J. Serrano, C. Alonso, and C. G. Nieto. 1996. Immunopathology of the uveitis in canine leishmaniasis. Parasite Immunol 18:617-23.
14. Garcia-Alonso, M., C. G. Nieto, A. Blanco, J. M. Requena, C. Alonso, and I. Navarrete. 1996. Presence of antibodies in the aqueous humour and cerebrospinal fluid during *Leishmania* infections in dogs. Pathological features at the central nervous system. Parasite Immunol 18:539-46.
15. Gradoni, L. 2001. An update on antileishmanial vaccine candidates and prospects for a canine *Leishmania* vaccine. Vet Parasitol 100:87-103.
16. Gramiccia, M., and L. Gradoni. 2005. The current status of zoonotic leishmaniases and approaches to disease control. Int J Parasitol 35:1169-80.
17. Handman, E., A. H. Noormohammadi, J. M. Curtis, T. Baldwin, and A. Sjolander. 2000. Therapy of murine cutaneous leishmaniasis by DNA vaccination. Vaccine 18:3011-7.
18. Herwaldt, B. L. 1999. Leishmaniasis. Lancet 354:1191-9.
19. Iborra, S., M. Soto, J. Carrion, C. Alonso, and J. M. Requena. 2004. Vaccination with a plasmid DNA cocktail encoding the nucleosomal histones of *Leishmania* confers protection against murine cutaneous leishmaniosis. Vaccine 22:3865-76.
20. Jaafari, M. R., A. Ghafarian, A. Farrokh-Gisour, A. Samiei, M. T. Kheiri, F. Mahboudi, F. Barkhordari, A. Khamesipour, and W. R. McMaster. 2006. Immune response and protection assay of recombinant major surface glycoprotein of *Leishmania* (rgp63) reconstituted with liposomes in BALB/c mice. Vaccine 24:5708-17.
21. Lopez, R., R. Lucena, M. Novales, P. J. Ginel, E. Martin, and J. M. Molleda. 1996. Circulating immune complexes and renal function in canine leishmaniasis. Zentralbl Veterinarmed B 43:469-74.
22. Mancianti, F., A. Poli, and A. Bionda. 1989. Analysis of renal immune-deposits in canine leishmaniasis. Preliminary results. Parassitologia 31:213-30.
23. Martins, D. R., S. M. Jeronimo, J. E. Donelson, and M. E. Wilson. 2006. *Leishmania chagasi* T-cell antigens identified through a double library screen. Infect Immun 74:6940-8.
24. McMahon-Pratt, D., and J. Alexander. 2004. Does the *Leishmania major* paradigm of pathogenesis and protection hold for New World cutaneous leishmaniases or the visceral disease? Immunol Rev 201:206-24.
25. Mendez, S., Y. Belkaid, R. A. Seder, and D. Sacks. 2002. Optimization of DNA vaccination against cutaneous leishmaniasis. Vaccine 20:3702-8.
26. Mendez, S., S. Gurunathan, S. Kamhawi, Y. Belkaid, M. A. Moga, Y. A. Skeiky, A. Campos-Neto, S. Reed, R. A. Seder, and D. Sacks. 2001. The potency and durability of DNA- and protein-based vaccines against *Leishmania major* evaluated using low-dose, intradermal challenge. J Immunol 166:5122-8.
27. Miles, S. A., S. M. Conrad, R. G. Alves, S. M. Jeronimo, and D. M. Mosser. 2005. A role for IgG immune complexes during infection with the intracellular pathogen *Leishmania*. J Exp Med 201:747-54.
28. Moore, K. W., R. de Waal Malefyt, R. L. Coffman, and A. O'Garra. 2001. Interleukin-10 and the interleukin-10 receptor. Annu Rev Immunol 19:683-765.
29. Mougneau, E., F. Altare, A. E. Wakil, S. Zheng, T. Coppola, Z. E. Wang, R. Waldmann, R. M. Locksley, and N. Glaichenhaus. 1995. Expression cloning of a protective *Leishmania* antigen. Science 268:563-6.
30. Nieto, C. G., R. Barrera, M. A. Habela, I. Navarrete, C. Molina, A. Jimenez, and J. L. Serrera. 1992. Changes in the plasma concentrations of lipids and lipoprotein fractions in dogs infected with *Leishmania infantum*. Vet Parasitol 44:175-82.

31. Nieto, C. G., I. Navarrete, M. A. Habela, F. Serrano, and E. Redondo. 1992. Pathological changes in kidneys of dogs with natural *Leishmania* infection. Vet Parasitol 45:33-47.
32. Noben-Trauth, N., R. Lira, H. Nagase, W. E. Paul, and D. L. Sacks. 2003. The relative contribution of IL-4 receptor signaling and IL-10 to susceptibility to *Leishmania major*. J Immunol 170:5152-8.
33. Pateraki, E., R. Portocala, H. Labrousse, and J. L. Guesdon. 1983. Antiactin and antitubulin antibodies in canine visceral leishmaniasis. Infect Immun 42:496-500.
34. Peters, N., and D. Sacks. 2006. Immune privilege in sites of chronic infection: *Leishmania* and regulatory T cells. Immunol Rev 213:159-79.
35. Pollock, K. G., K. S. McNeil, J. C. Mottram, R. E. Lyons, J. M. Brewer, P. Scott, G. H. Coombs, and J. Alexander. 2003. The *Leishmania* mexicana cysteine protease, CPB2.8, induces potent Th2 responses. J Immunol 170:1746-53.
36. Probst, P., E. Stromberg, H. W. Ghalib, M. Mozel, R. Badaro, S. G. Reed, and J. R. Webb. 2001. Identification and characterization of T cell-stimulating antigens from *Leishmania* by CD4 T cell expression cloning. J Immunol 166:498-505.
37. Rafati, S., A. Nakhaee, T. Taheri, A. Ghashghaii, A. H. Salmanian, M. Jimenez, M. Mohebali, S. Masina, and N. Fasel. 2003. Expression of cysteine proteinase type I and II of *Leishmania infantum* and their recognition by sera during canine and human visceral leishmaniasis. Exp Parasitol 103:143-51.
38. Rafati, S., A. H. Salmanian, T. Taheri, M. Vafa, and N. Fasel. 2001. A protective cocktail vaccine against murine cutaneous leishmaniasis with DNA encoding cysteine proteinases of *Leishmania major*. Vaccine 19:3369-75.
39. Requena, J. M., C. Alonso, and M. Soto. 2000. Evolutionarily conserved proteins as prominent immunogens during *Leishmania* infections. Parasitol Today 16:246-50.
40. Rhee, E. G., S. Mendez, J. A. Shah, C. Y. Wu, J. R. Kirman, T. N. Turon, D. F. Davey, H. Davis, D. M. Klinman, R. N. Coler, D. L. Sacks, and R. A. Seder. 2002. Vaccination with heat-killed *Leishmania* antigen or recombinant leishmanial protein and CpG oligodeoxynucleotides induces long-term memory CD4+ and CD8+ T cell responses and protection against *Leishmania major* infection. J Exp Med 195:1565-73.
41. Roberts, M. T., C. B. Stober, A. N. McKenzie, and J. M. Blackwell. 2005. Interleukin-4 (IL-4) and IL-10 collude in vaccine failure for novel exacerbatory antigens in murine *Leishmania major* infection. Infect Immun 73:7620-8.
42. Rodriguez-Gabriel, M. A., M. Remacha, and J. P. Ballesta. 2000. The RNA interacting domain but not the protein interacting domain is highly conserved in ribosomal protein P0. J Biol Chem 275:2130-6.
43. Rosa, R., C. Marques, 0. R. Rodrigues, and G. M. Santos-Gomes. 2007. Immunization with *Leishmania infantum* released proteins confers partial protection against parasite infection with a predominant Th1 specific immune response. Vaccine 25:4525-32.
44. Santos-Gomes, G. M.-, R. Rosa, C. Leandro, S. Cortes, P. Romao, and H. Silveira. 2002. Cytokine expression during the outcome of canine experimental infection by *Leishmania infantum*. Vet Immunol Immunopathol 88:21-30.
45. Santos, W. R., V. M. de Lima, E. P. de Souza, R. R. Bernardo, M. Palatnik, and C. B. Palatnik de Sousa. 2002. Saponins, IL12 and BCG adjuvant in the FML-vaccine formulation against murine visceral leishmaniasis. Vaccine 21:30-43.
46. Saraiva, E. M., A. de Figueiredo Barbosa, F. N. Santos, G. P. Borja-Cabrera, D. Nico, L. O. Souza, C. de Oliveira Mendes-Aguiar, E. P. de Souza, P. Fampa, L. E. Parra, I. Menz, J. G. Dias, Jr., S. M. de Oliveira, and C. B. Palatnik-de-Sousa. 2006. The FML-vaccine (Leishmune) against canine visceral leishmaniasis: a transmission blocking vaccine. Vaccine 24:2423-31.
47. Serezani, C. H., A. R. Franco, M. Wajc, J. K. Umada Yokoyama-Yasunaka, G. Wunderlich, M. M. Borges, and S. R. Uliana. 2002. Evaluation of the murine immune response to *Leishmania* meta 1 antigen delivered as recombinant protein or DNA vaccine. Vaccine 20:3755-63.
48. Skeiky, Y. A., J. A. Guderian, D. R. Benson, O. Bacelar, E. M. Carvalho, M. Kubin, R. Badaro, G. Trinchieri, and S. G. Reed. 1995. A recombinant *Leishmania* antigen that stimulates human peripheral blood mononuclear cells to express a Th1-type cytokine profile and to produce interleukin 12. J Exp Med 181:1527-37.
49. Stager, S., D. F. Smith, and P. M. Kaye. 2000. Immunization with a recombinant stage-regulated surface protein from *Leishmania donovani* induces protection against visceral leishmaniasis. J Immunol 165:7064-71.
50. Tonui, W. K., J. S. Mejia, L. Hochberg, M. L. Mbow, J. R. Ryan, A. S. Chan, S. K. Martin, and R. G. Titus. 2004. Immunization with *Leishmania major* exogenous antigens protects susceptible BALB/c mice against challenge infection with *L. major*. Infect Immun 72:5654-61.
51. Webb, J. R., A. Campos-Neto, Y. A. Skeiky, and S. G. Reed. 1997. Molecular characterization of the heat-inducible LmSTI1 protein of *Leishmania major*. Mol Biochem Parasitol 89:179-93.
52. Webb, J. R., D. Kaufmann, A. Campos-Neto, and S. G. Reed. 1996. Molecular cloning of a novel protein antigen of *Leishmania major* that elicits a potent immune response in experimental murine leishmaniasis. J Immunol 157:5034-41.
53. Zimmermann, S., O. Egeter, S. Hausmann, G. B. Lipford, M. Rocken, H. Wagner, and K. Heeg. 1998. CpG oligodeoxynucleotides trigger protective and curative Th1 responses in lethal murine leishmaniasis. J Immunol 160:3627-30.
54. S. Iborra, M. Soto, J. Carrion, A. Nieto, E. Fernandez, C. Alonso, J. M. Requena, The *Leishmania infantum* acidic ribosomal protein P0 administered as a DNA vaccine confers protective immunity to *Leishmania major* infection in BALB/c mice, Infect Immun 71 (2003) 6562-6572.
55. S. Iborra, N. Parody, D. R. Abanades, P. Bonay, D. Prates, F. O. Novais, M. Barral-Netto, C. Alonso, M. Soto, Vaccination with the *Leishmania major* ribosomal proteins plus CpG oligodeoxynucleotides induces protection against experimental cutaneous leishmaniasis in mice, Microbes Infect 10 (2008) 1133-1141.
56. W. H. Mager, R. J. Planta, J. G. Ballesta, J. C. Lee, K. Mizuta, K. Suzuki, J. R. Warner, J. Woolford, A new nomenclature for the cytoplasmic ribosomal proteins of *Saccharomyces cerevisiae*, Nucleic acids research 25 (1997) 4872-4875.
57. P. Y. Shi, N. Maizels, A. M. Weiner, Recovery of soluble, active recombinant protein from inclusion bodies, BioTechniques 23 (1997) 1036-1038.
58. N. Santarem, R. Silvestre, J. Tavares, M. Silva, S. Cabral, J. Maciel, A. Cordeiro-da-Silva, Immune response regulation by leishmania secreted and nonsecreted antigens, J Biomed Biotechnol 2007 (2007) 85154.

59. Boarino, A., A. Scalone, L. Gradoni, E. Ferroglio, F. Vitale, R. Zanatta, M. G. Giuffrida, and S. Rosati. 2005. Development of recombinant chimeric antigen expressing immunodominant B epitopes of *Leishmania infantum* for serodiagnosis of visceral leishmaniasis. Clin Diagn Lab Immunol 12:647-53.
60. Porrozzi, R., M. V. Santos da Costa, A. Teva, A. Falqueto, A. L. Ferreira, C. D. dos Santos, A. P. Fernandes, R. T. Gazzinelli, A. Campos-Neto, and G. Grimaldi, Jr. 2007. Comparative evaluation of enzyme-linked immunosorbent assays based on crude and recombinant leishmanial antigens for serodiagnosis of symptomatic and asymptomatic *Leishmania infantum* visceral infections in dogs. Clin Vaccine Immunol 14:544-8.
61. Soto, M., J. M. Requena, L. Quijada, and C. Alonso. 1998. Multicomponent chimeric antigen for serodiagnosis of canine visceral leishmaniasis. J Clin Microbiol 36:58-63.
62. Melby P. C. G. B., Ogden H. A., Flores W., Zhao C., Geldmacher, N. M., Biediger S. K., Ahuja, J., Uranga and M. Melendez (2000), Identification of vaccine candidates for experimental visceral leishmaniasis by immunization with sequential fractions of a cDNA library. Infect. Immun., 68: 5595-5602.
63. Stober C. B. U. G., Lange M. T., Roberts B, Gilmartin R., Francis R., Almeida C. S., Peacock S., McCann and J. M. Blackwell, (2006), From genome to vaccines for leishmaniasis: screening 100 novel vaccine candidates against murine Leishmaniasis major infection. Vaccine., 24: 2602-2616.
64. Aebischer T., et al, (2000) Infection and Immunity., 68: 1328-1336.
65. Poot J et al, (2009), Vaccine, 27: 4439-4446.
66. Ferreira J. H. et al, (2008), Vaccine, 26: 67-685.
67. Buckanovich R. J., et al, (1994), Proc. Natl. Acad. Sci. USA, 91:4892.
68. Liu N., et al (2003), Nature Immunology, 687-693).
69. Bertholet S, Goto Y, Carter L, Bhatia A, Howard R F, Carter D, Coler R N, Vedvick T S, Reed S G. Vaccine. 2009 Nov. 23; 27(50):7036-45.
70. S. Iborra, J. Carrion, C. Anderson, C. Alonso, D. Sacks, M. Soto, Vaccination with the *Leishmania infantum* acidic ribosomal P0 protein plus CpG oligodeoxynucleotides induces protection against cutaneous leishmaniasis in C57BL/6 mice but does not prevent progressive disease in BALB/c mice, Infect Immun 73 (2005) 5842-5852
71. M. Soto, J. M. Requena, L. Quijada, M. J. Perez, C. G. Nieto, F. Guzman, M. E. Patarroyo, C. Alonso, Antigenicity of *the Leishmania infantum* histones H2B and H4 during canine viscerocutaneous leishmaniasis, Clin Exp Immunol 115 (1999) 342-349.
72. T. R. de Moura, F. O. Novais, F. Oliveira, J. Clarencio, A. Noronha, A. Barral, C. Brodskyn, C. I. de Oliveira, Toward a novel experimental model of infection to study American cutaneous leishmaniasis caused by *Leishmania braziliensis*, Infect Immun 73 (2005) 5827-5834.
73. S. Iborra, J. Carrion, C. Anderson, C. Alonso, D. Sacks, M. Soto, Vaccination with the *Leishmania infantum* acidic ribosomal P0 protein plus CpG oligodeoxynucleotides induces protection against cutaneous leishmaniasis in C57BL/6 mice but does not prevent progressive disease in BALB/c mice, Infect Immun 73 (2005) 5842-5852.

The invention claimed is:

1. A method for the development of a protective immune response against leishmaniasis caused by *Leishmania major, Leishmania braziliensis, Leishmania amazonensis* or by a species of the *Leishmania donovani* complex selected from the group consisting of *Leishmania donovani, Leishmania chagasi* and *Leishmania infantum* in a subject by administering to the subject a $TH_1$-promoting adjuvant and an effective amount of a composition comprising an L5 polypeptide,
   wherein said L5 polypeptide comprises the amino acid sequence set forth as SEQ ID NO:3.

2. The method according to claim 1, wherein said composition also comprises an L3 polypeptide,
   wherein said L3 polypeptide comprises the amino acid sequence set forth as SEQ ID NO:1.

3. The method according to claim 1, wherein said composition comprising said L5 polypeptide is a vaccine.

4. The method according to claim 1, wherein the $Th_1$-promoting adjuvant is a CpG ODN.

5. The method according to claim 1, wherein the species of the *Leishmania donovani* complex are *Leishmania chagasi* or *Leishmania infantum*.

* * * * *

SEQUENCE LISTING

```
<160> NUMBER OF SEQ ID NOS: 73

<210> SEQ ID NO 1
<211> LENGTH: 419
<212> TYPE: PRT
<213> ORGANISM: Leishmania major

<400> SEQUENCE: 1

Met Ser His Cys Lys Phe Glu His Pro Arg His Gly His Leu Gly Phe
1               5                   10                  15

Leu Pro Arg Lys Arg Ser Arg Gln Ile Arg Gly Arg Ala Arg Ala Phe
            20                  25                  30

Pro Lys Asp Asp Ala Thr Gln Lys Pro His Leu Thr Ser Phe Met Val
        35                  40                  45

Phe Lys Ala Gly Met Thr His Ile Val Arg Asp Val Asp Arg Pro Gly
    50                  55                  60

Ser Lys Val Asn Lys Lys Glu Val Val Glu Pro Val Thr Ile Leu Glu
65                  70                  75                  80

Ala Pro Pro Met Val Ile Val Gly Ile Val Gly Tyr Arg Gln Thr Pro
                85                  90                  95

Val Gly Leu Lys Thr Ile Gly Thr Val Trp Ala His His Thr Ser Val
            100                 105                 110

Glu Phe Arg Arg Arg Tyr Tyr Lys Asn Trp Lys Gln Ser Ala Gln Leu
        115                 120                 125

Ala Phe Ser Arg Gln Lys Gln Phe Ala Asn Thr Lys Glu Gly Lys Val
    130                 135                 140
```

```
Ala Glu Ala Arg Thr Leu Asn Ala Phe Ala Lys Lys Ala Ser Val Ile
145                 150                 155                 160

Arg Val Ile Ala His Thr Gln Leu Arg Lys Leu Arg Asn His Arg Val
                165                 170                 175

Gly Val Lys Lys Ala His Val Gln Glu Ile Gln Val Asn Gly Gly Ser
            180                 185                 190

Val Ala Ala Lys Ile Ala Leu Ala Lys Ser Leu Leu Glu Lys Glu Val
        195                 200                 205

Arg Val Asp Ser Val Phe Gln Gln Ser Glu Ala Cys Asp Val Cys Ser
    210                 215                 220

Val Thr Lys Gly His Gly Thr Glu Gly Val Val Lys Arg Trp Gly Val
225                 230                 235                 240

Ala Cys Leu Pro Arg Lys Thr His Arg Gly Leu Arg Lys Val Ala Cys
                245                 250                 255

Ile Gly Ala Trp His Pro Ala Arg Val Met Tyr Thr Val Ala Arg Ala
            260                 265                 270

Gly Gln His Gly Tyr His His Arg Thr Gln Leu Asn Lys Lys Ile Tyr
        275                 280                 285

Gln Ile Gly Arg Ser Val Ala Val Glu Pro Asn Gln Ala Thr Thr Thr
    290                 295                 300

Tyr Asp Leu Thr Ala Lys Thr Ile Thr Pro Met Gly Gly Phe Val Gly
305                 310                 315                 320

Tyr Gly Thr Val Arg Asn Asp Tyr Val Met Leu Lys Gly Ser Val Ser
                325                 330                 335

Gly Pro Arg Arg Arg Val Met Thr Leu Arg Arg Pro Met Ala Pro Gln
            340                 345                 350

Thr Ser Arg Gln Leu Lys Glu Lys Ile Val Leu Lys Phe Ile Asp Thr
        355                 360                 365

Ser Ser Lys Ile Gly His Gly Arg Phe Gln Thr Lys Lys Glu Lys Asn
    370                 375                 380

Gln Trp Phe Gly Pro Leu Lys Lys Asp Arg Ile Arg Arg Glu Glu Arg
385                 390                 395                 400

Leu Arg Lys Glu Arg Ala Ala Arg Ala Val Glu Arg Lys Ala Lys Ala
                405                 410                 415

Ala Lys Lys

<210> SEQ ID NO 2
<211> LENGTH: 1260
<212> TYPE: DNA
<213> ORGANISM: Leishmania major

<400> SEQUENCE: 2
atgtctcact gcaagttcga gcaccccgc cacggccatc tcggcttcct gccgcgcaag      60
cgctcgcgcc agatccgcgg ccgtgcgcgc gcgttcccca aggacgacgc gacgcagaag     120
ccccacctga cgagcttcat ggtgttcaag gccggtatga cgcacattgt gcgtgatgtc     180
gatcgccctg gatcgaaggt gaacaagaag gaagtggtgg agccggtgac gatcctggag     240
gcgccgccga tggtgattgt cggcattgtg ggctaccgcc aaacgccggt tggcctgaag     300
acgatcggca ccgtgtgggc gcaccacacg agcgtcgagt ccgccgccg ctactacaag     360 aactggaagc agtctgcgca actggccttc tcccgccaga gcagtttgc gaacacgaag     420 gagggcaagt cgccgaggc gcgcacgctg aacgcgttcg cgaagaaggc gtccgtcatc     480
cgcgtgatcg cgcacacgca gctgcgcaag cttcgcaacc accgcgtggg cgtgaagaag     540
```

```
gcgcacgtgc aggagatcca ggtcaacggc ggcagcgttg cggcgaagat cgcgctggcc    600
aagtccctgc tggagaagga ggtgcgcgtc gactccgtgt ccagcagtc cgaggcgtgc    660 gacgtgtgct ccgtcacgaa aggccacggt acggagggcg tggtgaagcg ctgggcgtt    720 gcctgcctgc cacgcaagac gcaccgcggt ctgcgcaagg ttgcgtgcat cggcgcgtgg    780
caccctgccc gcgtcatgta cactgtcgcg cgcgccggtc agcacggtta ccaccaccgc    840
acgcagctga acaagaagat ctaccagatc ggccgctccg ttgctgtgga gccgaaccag    900
gcgacgacga cctacgatct gacagccaag acgatcacgc ccatgggtgg cttcgtcggc    960
tacggtacgg tgcgcaacga ctacgtgatg ctgaagggct ccgtgtctgg cccgcgccg    1020 cgtgtgatga cgctgcgccg cccgatggcg ccgcagacgt cgcgccagct gaaggagaag    1080
atcgtgctga agttcatcga cacgagctcg aagatcggcc acggccgctt ccagacgaag    1140
aaggagaaga accagtggtt cggcccgctc aagaaggacc gcatccgccg cgaggagcgc    1200
ctgcgcaagg agcgcgctgc ccgcgccgtg gagcgcaagg caaaggccgc gaagaagtaa    1260
```

<210> SEQ ID NO 3
<211> LENGTH: 328
<212> TYPE: PRT
<213> ORGANISM: Leishmania major

<400> SEQUENCE: 3

```
Met Cys Thr Leu Ala Asn Trp Val Arg Ala Ile Ile Lys Lys His Ser
1               5                   10                  15

Thr Leu Ala His Thr Leu Glu Met Pro Phe Val Lys Val Val Lys Asn
            20                  25                  30

Lys Ala Tyr Phe Lys Arg Phe Gln Val Lys Tyr Arg Arg Arg Arg Glu
        35                  40                  45

Gly Lys Thr Asp Tyr His Ala Arg Arg Gln Met Val Leu Gln Asp Lys
    50                  55                  60

Thr Lys Phe Gly Ser Pro Lys Tyr Arg Leu Val Val Arg Ile Thr Asn
65                  70                  75                  80

Lys Asp Ile Ile Ala Gln Ile Val Gln Ala Lys Ile Val Gly Asp Glu
                85                  90                  95

Val Val Met Ala Ala Tyr Ala His Glu Leu Pro Ala Phe Gly Ile Glu
            100                 105                 110

His Gly Leu Thr Asn Tyr Ala Ala Ala Tyr Ala Thr Gly Leu Leu Leu
        115                 120                 125

Ala Arg Arg Thr Leu Ala Lys Leu Gly Ile Ala Asp Lys Phe Gln Gly
    130                 135                 140

Ala Lys Glu Ala Asp Gly Ser Tyr Ser Ala Val Arg Thr Lys Lys Asp
145                 150                 155                 160

Asp Glu Gly Asp Asp Glu Glu Arg Phe Pro Phe Lys Ala Ile Leu Asp
                165                 170                 175

Val Gly Leu Ala Arg Thr Thr Thr Gly Ala Arg Val Phe Gly Val Leu
            180                 185                 190

Lys Gly Ala Val Asp Gly Gly Met Ala Val Pro His Arg Pro Asn Arg
        195                 200                 205

Phe Pro Gly Tyr Asn Lys Glu Lys Ser Ser Leu Asp Ala Lys Val His
    210                 215                 220

Arg Asp Arg Ile Phe Gly Lys His Val Ala Asp Tyr Leu Lys Gln Val
225                 230                 235                 240

Lys Glu Glu Ala Ser Ser Asn Pro Asp Glu Lys Cys Val Gln Phe Ser
                245                 250                 255
```

```
Lys Tyr Met Ala Ala Lys Val Leu Pro Glu Ser Ile Glu Gly Met Tyr
            260                 265                 270
Lys Lys Ala His Ala Ala Ile Arg Ala Asp Pro Ser Lys Ser Leu Pro
        275                 280                 285
Lys Lys Ala Lys Lys Glu Gly Val Ala His Lys Ser Tyr Lys Thr Lys
    290                 295                 300
Lys Leu Ser Gly Ala Glu Lys Arg Ala Ala Lys Ala Lys Val Ala
305                 310                 315                 320
Ala Ile Arg Glu Arg Leu Gly Lys
                325
```

<210> SEQ ID NO 4
<211> LENGTH: 987
<212> TYPE: DNA
<213> ORGANISM: Leishmania major

<400> SEQUENCE: 4

```
atgtgcacgc tggcaaattg ggtacgcgct atcatcaaga acactcaac actcgcccac      60
acactcgaga tgccgttcgt caaggtcgtg aagaacaagg cgtacttcaa gcgcttccag    120
gtgaagtacc gccgtcgccg cgagggcaag acggactacc acgcgcgccg gcagatggtg    180
ctgcaggaca agacgaagtt cggctcgccc aagtaccgcc ttgttgtgcg catcacgaac    240
aaggacatca ttgcgcagat cgtgcaggcg aagatcgtcg cgacgaggt ggtgatggcc    300
gcgtacgcgc acgagctgcc tgcgttcggc attgagcacg gcctgacaaa ctacgctgct    360
gcgtacgcga ctggtctgct gctggcgcgc cgcacgctgg cgaagctggg catcgcggac    420
aagttccagg gcgcgaagga ggcggacggc tcgtactctg ctgtgcgcac gaagaaggac    480
gacgagggcg acgacgagga gcgctttccg ttcaaggcga tcctggacgt cggccttgcg    540
cgcacgacga ccggcgcccg cgtgttcggc gtgctgaagg gcgcggtgga cggcggtatg    600
gctgtgccgc accgccccaa ccgcttcccc ggctacaaca aggagaagag ctcgctggac    660
gcgaaggtgc accgcgaccg catctttggc aagcacgtgg cggactacct gaagcaggtg    720
aaggaggagg cgagctcgaa ccctgacgag aagtgcgtgc agttctcgaa gtacatggcc    780
gcgaaggttt tgccggagag catcgagggc atgtacaaga aggcgcacgc ggcgatccgc    840
gcggacccgt cgaagtcgct gccgaagaag gcgaagaagg agggcgtcgc cacaagagc    900
tacaagacga agaagctgag cggcgcggag aagagggccg ccgcgaaggc gaaggtcgcg    960
gccatccgcg agcgcctcgg caagtaa                                        987
```

<210> SEQ ID NO 5
<211> LENGTH: 10
<212> TYPE: DNA
<213> ORGANISM: artificial
<220> FEATURE:
<223> OTHER INFORMATION: adjuvant

<400> SEQUENCE: 5

```
tcaacgttga                                                            10
```

<210> SEQ ID NO 6
<211> LENGTH: 14
<212> TYPE: DNA
<213> ORGANISM: artificial
<220> FEATURE:
<223> OTHER INFORMATION: adjuvant

```
<400> SEQUENCE: 6
gctagcgtta gcgt                                                        14

<210> SEQ ID NO 7
<211> LENGTH: 132
<212> TYPE: PRT
<213> ORGANISM: Leishmania infantum

<400> SEQUENCE: 7

Met Ala Thr Pro Arg Ser Ala Lys Lys Ala Val Arg Lys Ser Gly Ser
1               5                   10                  15

Lys Ser Ala Lys Cys Gly Leu Ile Phe Pro Val Gly Arg Val Gly Gly
            20                  25                  30

Met Met Arg Arg Gly Gln Tyr Ala Arg Arg Ile Gly Ala Ser Gly Ala
        35                  40                  45

Val Tyr Leu Ala Ala Val Leu Glu Tyr Leu Thr Ala Glu Leu Leu Glu
    50                  55                  60

Leu Ser Val Lys Ala Ala Ala Gln Ser Gly Lys Lys Arg Cys Arg Leu
65                  70                  75                  80

Asn Pro Arg Thr Val Met Leu Ala Ala Arg His Asp Asp Asp Ile Gly
                85                  90                  95

Thr Leu Leu Lys Asn Val Thr Leu Ser His Ser Gly Val Val Pro Asn
            100                 105                 110

Ile Ser Lys Ala Met Ala Lys Lys Gly Gly Lys Lys Gly Lys Ala
        115                 120                 125

Thr Pro Ser Ala
    130

<210> SEQ ID NO 8
<211> LENGTH: 691
<212> TYPE: DNA
<213> ORGANISM: Leishmania infantum

<400> SEQUENCE: 8
gcctcatccg tcatccgtca tctttgtgct acagctttac tctcactccc ctccaaccta      60
cccatcgcag ccatggctac tcctcgcagc gccaagaagg ccgtccgcaa gagcggctcc     120
aagtccgcga aatgtggtct gatcttcccg gtgggccgcg tcggcgggat gatgcgccgc     180
ggccagtacg ctcgccgcat cggtgcctct ggcgccgtgt acctggccgc cgtgctggag     240
tacctgacgg cggagctgct ggagctgtcc gtgaaggcgg ccgcgcagag cgggaagaag     300
cggtgccgcc tgaacccgcg caccgtgatg ctggccgcgc gccacgacga cgacatcggc     360
acgcttctga agaacgtgac cttgtctcac agcggcgttg tgccgaacat cagcaaggcg     420
atggcaaaga agaagggcgg caagaagggc aagcgacac cgagcgcgta agtcctccgg     480
cctgacagcg cacacgcgcc gctgtattgt gcgcgtgcgc gcgggtcccg actgggaccg     540
gcgatgaggc gcatcatacc tccatagaga ccctatcttt tgttttatgg cttctcagat     600
gaccacttgg ttcttcctgc ctttgtttgg tttgtttctc tcctcccctc cgccgagggt     660
acgagtcagg gtaggctcgg acaaaaaaaa a                                    691

<210> SEQ ID NO 9
<211> LENGTH: 111
<212> TYPE: PRT
<213> ORGANISM: Leishmania infantum
```

-continued

<400> SEQUENCE: 9

Met Ala Ser Ser Arg Ser Ala Pro Arg Lys Ala Ser His Ala His Lys
1               5                   10                  15

Ser His Arg Lys Pro Lys Arg Ser Trp Asn Val Tyr Val Gly Arg Ser
            20                  25                  30

Leu Lys Ala Ile Asn Ala Gln Met Ser Met Ser His Arg Thr Met Ser
        35                  40                  45

Ile Val Asn Ser Tyr Val Asn Asp Val Met Glu Arg Ile Cys Met Glu
    50                  55                  60

Ala Ala Ser Ile Val Arg Ala Asn Lys Lys Arg Thr Leu Gly Ala Arg
65                  70                  75                  80

Glu Val Gln Thr Ala Val Arg Ile Val Leu Pro Ala Glu Leu Ala Lys
                85                  90                  95

His Ala Met Ala Glu Gly Thr Lys Ala Val Ser Ser Ala Ser Ala
            100                 105                 110

<210> SEQ ID NO 10
<211> LENGTH: 894
<212> TYPE: DNA
<213> ORGANISM: Leishmania infantum

<400> SEQUENCE: 10
ccaagccagc caaatccttc gcactttcac gctgtccctc ctttccaacc aacccacatc      60
accatggcct cttctcgctc tgctccccgc aaggcttccc acgcgcacaa gtcgcaccgc     120
aagccgaagc gctcgtggaa cgtgtacgtg ggccgctcgc tgaaggcgat caacgcccag     180
atgtcgatgt cgcaccgcac gatgagcatc gtgaactcgt acgtgaacga cgtgatggag     240
cgcatctgca tggaggccgc gtcgatcgtt cgcgcgaaca agaagcgcac gttgggtgcg     300
cgcgaggtgc agacggcggt gcgcattgtg ctgccggcgg agctcgcgaa gcacgccatg     360
gctgagggca cgaaggccgt gtcgagcgcg tcggcttgag cggctcagtt agagggtttg     420
tccacgcctc ggccgtgtgt ccggggtgtg gggtaccctc aactcccctc tccccgccta     480
cgccgtgggt tttcatagag atttattgtt tcttttttcga ttctctttcc ttgaaggtga    540
tgtctcgtcc tttgctggag tgcgtgccgg gttcgcgggc ggtagaaagc agcggcggag     600
gaggcagcgg cggcgcgaga cggtgaaggg gaggagaggc gggccgaaag cacagatgcg     660
cttctccgtc tctttctccc ttctctgcat tcgccctcgc tgctcctctc tgatgccctc     720
gtacctcgtg gtgcgcgcgt ctcccgctcg ccgtccgcgc cacgctgcac agaggcgtgc     780
acggtttgtc ttctatctca gaacgagtga cacacacgtt ttcttgttcc cccctccccc     840
cttcgtcatc gcttcttcgt tttcgttgtc gtctcgacgc ccaaaaaaaa aaaa            894

<210> SEQ ID NO 11
<211> LENGTH: 129
<212> TYPE: PRT
<213> ORGANISM: Leishmania infantum

<400> SEQUENCE: 11

Met Ser Arg Thr Lys Glu Thr Ala Arg Ala Lys Arg Thr Ile Thr Ser
1               5                   10                  15

Lys Lys Ser Lys Lys Ala Pro Ser Gly Ala Ser Gly Val Lys Arg Ser
            20                  25                  30

```
His Arg Arg Trp Arg Pro Gly Thr Cys Ala Ile Arg Glu Ile Arg Lys
            35                  40                  45

Phe Gln Lys Ser Thr Ser Leu Leu Ile Gln Cys Ala Pro Phe Gln Arg
 50                  55                  60

Leu Val Arg Gly Val Glu Arg Gln Lys Glu Gly Leu Arg Phe Gln Ser
 65                  70                  75                  80

Ser Ala Ile Met Ala Leu Gln Glu Ala Thr Glu Ala Tyr Ile Val Ser
                 85                  90                  95

Leu Met Ala Asp Thr Asn Leu Ala Cys Ile His Ala Lys Arg Val Thr
            100                 105                 110

Ile Gln Pro Lys Asp Ile Gln Leu Ala Leu Arg Leu Arg Gly Glu Arg
            115                 120                 125

His

<210> SEQ ID NO 12
<211> LENGTH: 587
<212> TYPE: DNA
<213> ORGANISM: Leishmania infantum

<400> SEQUENCE: 12
gtttcactac cgccatccaa cccoctgcca ctcccacccc caccgcacca ccatgtcccg      60
caccaaggag accgcccgcg cgaagcgcac catcacgtcg aagaagagca agaaggcgcc     120
gagcggggcg tccggcgtga agaggtcgca tcgccgctgg cgcccgggca cctgcgcgat     180
ccgcgagatc cgcaagttcc agaagagtac gagcctgctg atccagtgcg cgccgttcca     240
gcgcctggtg cgaggtgtcg agcggcagaa ggagggcctg cgcttccaga gcagcgctat     300
catggcgctg caggaggcga cggaggcgta cattgtgtcg ctgatggcgg acacgaacct     360
cgcctgcatc cacgcgaagc gcgtgacgat ccagccgaag gacatccagc tggcgctgcg     420
cctgcgcggt gagcgccact agggcgggcc cgctctcccc ccctcatag ataccatgtt      480 tttgtttcct ttcttttcgc cttccctaag tcgtgcacgc tgccctgccg cggcagccga     540
gagagtgaga gggtcattga acctctagag cccgccaaaa aaaaaaa                   587

<210> SEQ ID NO 13
<211> LENGTH: 100
<212> TYPE: PRT
<213> ORGANISM: Leishmania infantum

<400> SEQUENCE: 13

Met Ala Lys Gly Lys Arg Ser Thr Asp Ala Lys Gly Ser Gln Arg Arg
  1               5                  10                  15

Gln Lys Lys Val Leu Arg Asp Asn Ile Arg Gly Ile Thr Arg Gly Cys
             20                  25                  30

Val Arg Arg Met Ala Arg Arg Gly Gly Val Lys Arg Ile Ser Thr Glu
             35                  40                  45

Val Tyr Glu Glu Val Arg Arg Val Leu Lys Ala Tyr Val Glu Asp Ile
 50                  55                  60

Val Arg Cys Ser Thr Ala Tyr Thr Glu Tyr Ala Arg Lys Lys Thr Val
 65                  70                  75                  80

Thr Ala Cys Asp Val Val Thr Ala Leu Arg Lys Gln Gly His Ile Leu
                 85                  90                  95

Tyr Gly Tyr Ala
            100
```

-continued

<210> SEQ ID NO 14
<211> LENGTH: 531
<212> TYPE: DNA
<213> ORGANISM: Leishmania infantum

<400> SEQUENCE: 14

```
gctcccttt c ttgcctcctc tccccccac gcctcctccc ttcacatatc caccatggcc      60
aagggcaagc gttccactga tgccaagggc agccagaggc gccagaagaa ggtgctgcgc     120
gacaacatcc gcggcatcac tcgcggctgc gtccgccgca tggcgcgccg cggtggcgtg     180
aagcgcatct cgaccgaggt gtacgaagag gtgcgccgtg tgctgaaggc ctacgtggag     240
gacattgtgc gctgcagcac ggcctacacc gagtacgcgc gcaagaagac cgtgacggcg     300
tgcgatgttg tgaccgcgct gcgcaagcaa ggccacatcc tgtacggcta cgcgtaaatg     360
ctcgcagagc cgctgcacac tcatagatac accttctttg ttcatgccgt cgtttcgttg     420
gctttcttgg ttttcgactt cccttccccc cactatggct tttctttcgt ctcgtgctgg     480
caccctttcc ctactcatcgc tgtttgctga aggcagtaca gaacgaagcg g            531
```

<210> SEQ ID NO 15
<211> LENGTH: 106
<212> TYPE: PRT
<213> ORGANISM: Leishmania infantum

<400> SEQUENCE: 15

Met Gln Tyr Leu Ala Ala Tyr Ala Leu Val Ala Leu Ser Gly Lys Thr
1               5                   10                  15

Pro Ser Lys Ala Asp Val Gln Ala Val Leu Lys Ala Ala Gly Val Ala
            20                  25                  30

Val Asp Ala Ser Arg Val Asp Ala Val Phe Gln Glu Val Glu Gly Lys
        35                  40                  45

Ser Phe Asp Ala Leu Val Ala Glu Gly Arg Thr Lys Leu Val Gly Ser
    50                  55                  60

Gly Ser Ala Ala Pro Ala Gly Ala Val Ser Thr Ala Gly Ala Gly Ala
65                  70                  75                  80

Gly Ala Val Ala Glu Ala Lys Lys Glu Glu Pro Glu Glu Glu Glu Ala
                85                  90                  95

Asp Asp Asp Met Gly Phe Gly Leu Phe Asp
            100                 105

<210> SEQ ID NO 16
<211> LENGTH: 106
<212> TYPE: PRT
<213> ORGANISM: Leishmania infantum

<400> SEQUENCE: 16

Met Gln Tyr Leu Ala Ala Tyr Ala Leu Val Ala Leu Ser Gly Lys Thr
1               5                   10                  15

Pro Ser Lys Ala Asp Val Gln Ala Val Leu Lys Ala Ala Gly Val Ala
            20                  25                  30

Val Asp Ala Ser Arg Val Asp Ala Val Phe Gln Glu Val Glu Gly Lys
        35                  40                  45

Ser Phe Asp Ala Leu Val Ala Glu Gly Arg Thr Lys Leu Val Gly Ser
    50                  55                  60

Gly Ser Ala Ala Pro Ala Gly Ala Val Ser Thr Ala Gly Ala Gly Ala
65                  70                  75                  80

Gly Ala Val Ala Glu Ala Lys Lys Glu Glu Pro Glu Glu Glu Ala
            85                  90                  95

Asp Asp Asp Met Gly Phe Gly Leu Phe Asp
            100                 105

<210> SEQ ID NO 17
<211> LENGTH: 2850
<212> TYPE: DNA
<213> ORGANISM: Leishmania infantum

<400> SEQUENCE: 17

| | | | | | |
|---|---|---|---|---|---|
| gtcgacggcg | acatggctag | agcagtttgt | gcagctcccg | ctgagcgaca | agaaacacga | 60 |
| tctgccgcgt | cgccacggag | gtgtttctcc | atgcctttgc | ccagtgcatc | aatgagtccg | 120 |
| ggatctttgt | cgcaccacca | gcaaaagagg | agcagtgcct | actcgcggcc | ttaggaacgg | 180 |
| caatgcgacc | ttttgcacag | taccccgagg | agacgatcgc | ccaggcaaat | gcgtttctgc | 240 |
| atcaaggagg | gcttccgcat | gtcccgttcg | cagctgaggc | ggtggagcag | caggttatga | 300 |
| atctccagcg | gctgcattaa | tcgccgcctg | ccagacaccg | ggaggtcct | ctgtttctgt | 360 |
| ttttgcgtgt | tgcgtctttc | tctttatgtt | tgctcctttg | tgtctgtcgg | ttaagagctc | 420 |
| ctcccttgcc | cagaaaacag | gagtaaccga | gtacgccgca | gcgcctgcgc | cacacgttgt | 480 |
| ccatggaacc | cctcccctcc | tcgctcctcc | cttctccact | ccctccttct | gggtgctgca | 540 |
| tgtgtgtgtg | catgtgtgtg | taactttgcc | tcggtgtggc | tggcacgctg | cgcccctcc | 600 |
| ccccccccc | ccaaaaaaaa | aaaacagcat | catcagtggg | ctgacctgga | tacatctcct | 660 |
| cctctccttg | tgttccccat | cccctcttcg | ctcttcctct | atgcacctcg | cccactgcgc | 720 |
| gcatcacgca | cgcatcatcg | cggctacgga | acacgcgacc | cccacccac | ataggttttt | 780 |
| tcaacgagaa | atgcagtacc | ttgccgcgta | cgccctcgtg | gcgctgtctg | caagacgcc | 840 |
| gtcgaaggcg | gacgttcagg | ctgtcctgaa | ggccgccggc | gttgccgtgg | atgcctcccg | 900 |
| cgtggatgcc | gtcttccagg | aggtggaggg | caagagcttc | gatgcgctgg | tggccgaggg | 960 |
| ccgcacgaag | ctggtgggct | ctggctctgc | cgctcctgct | ggcgctgtct | ccactgctgg | 1020 |
| tgccggcgct | ggcgcggtgg | ccgaggcgaa | gaaggaggag | cccgaggagg | aggaggccga | 1080 |
| tgatgacatg | ggcttcggtc | tctttgacta | agcagccccg | cactgcgctg | caggcgcctc | 1140 |
| tgccgaagat | tctcacgcgg | gcctgctctc | attgttgtga | tgcatcgttt | ctttcttgc | 1200 |
| ttgtgacttc | ggttcgtctt | ttgatttcga | gtggaaagac | tctgcaaatc | gaacaacccg | 1260 |
| tgcgagatga | gctgggagcg | taggcgaggt | ggctgctcgc | gaggctgtaa | cgaaaaaaaa | 1320 |
| aagacagcag | cggcgccctc | ggcacaaaca | cagcgagccc | tcccctcccc | cgcttcgtcc | 1380 |
| ctcctcgaga | agagagagac | aaagaatctc | cacagacgct | gtacgagagg | caccggcctc | 1440 |
| gtcatcgaga | gaagcaaccg | cgctttcgtg | ccgtgacccg | ctgaccttcg | ataaccgaga | 1500 |
| gagggtgtct | tctcttctca | aagtgggttc | attgcgaagt | gctgctctac | tgtccctcct | 1560 |
| gctcgtcttc | cccagttct | cgtttcgtct | ctttttttgtt | cgttccatgc | actttctctc | 1620 |
| atactgtttt | tgcctcttgt | cgtacaagag | gtgtatcaaa | catgcagtac | ctcgccgcgt | 1680 |
| acgcctcgt | ggcgctgtct | ggcaagacgc | cgtcgaaggc | ggacgttcag | gctgtcctga | 1740 |
| aggccgccgg | cgttgccgtg | gatgcctccc | gcgtggatgc | cgtcttccag | gaggtggagg | 1800 |
| gcaagagctt | cgatgcgctg | gtggccgagg | gtcgcacgaa | gctggtgggc | tctggctctg | 1860 |
| ccgctcctgc | tggcgctgtc | tccactgctg | gtgccggcgc | tggcgcggtg | gccgaggcga | 1920 |
| agaaggagga | gcccgaggag | gaggaggccg | atgatgacat | gggcttcggt | ctctttgact | 1980 |

| | |
|---|---|
| aagcagcctc cgtgagtggt ctactgtcgt tacttttga cttgtttcat ttgacttgtt | 2040 |
| ttcttcccgt aagcaaagaa cagagtaagc aagcatccat gcacgtcgaa gcgatgctac | 2100 |
| gaaccggtct ccctgctgcc catatcccct cagcgacggc gaccctccct cctttccacg | 2160 |
| tgctgacctc atctcctcca atctttcacc ttctcttctg tctctcttct tgggttccct | 2220 |
| cttgaccgat cctgcatcga ccatgaccag gtaattgcta tggctcttca agagaatagg | 2280 |
| gactcctaca aggtcaaagc ttttccttg tccgagtttg tgcggcagtg ttccgactgc | 2340 |
| caccagctgt gcctcgagaa gacggcccgc gttgtggaaa acagcagtcg tgccccgcgg | 2400 |
| ggatgggaag ccctattcaa ctccgttgcg gaggagcggc ggtctgagga cttggacctc | 2460 |
| tgcgagtcgc gatgccggta catgcaggcc acctgcccgt cacaggagaa ggtccagcag | 2520 |
| tacgagcagg ctctcgccgc cgcgttactc aagccgaaaa agagcacgcc cccaaacccg | 2580 |
| tctgtcttgc aagacgcttc ccggtgcggc acgcggtcga ggttttctcg aacgtcctgt | 2640 |
| tgcccgtggc gcacaaaccc agaaggtatc cttcccaacc aaagacctga acgggaggc | 2700 |
| acaccgacgc cggtcccacg ccggacggcc gacggaggcg accgaaggtg ctcgagggga | 2760 |
| ccaagacatg gacaacgata tttcgcgccg ctggagcaag cttcgccaag agcgcttcgg | 2820 |
| ctcaaaggca gagcacgttg ctccgtcgac | 2850 |

<210> SEQ ID NO 18
<211> LENGTH: 111
<212> TYPE: PRT
<213> ORGANISM: Leishmania infantum

<400> SEQUENCE: 18

```
Met Ser Thr Lys Tyr Leu Ala Ala Tyr Ala Leu Ala Ser Leu Ser Lys
1               5                   10                  15

Ala Ser Pro Ser Gln Ala Asp Val Glu Ala Ile Cys Lys Ala Val His
            20                  25                  30

Ile Asp Val Asp Gln Ala Thr Leu Ala Phe Val Met Glu Ser Val Thr
        35                  40                  45

Gly Arg Asp Val Ala Thr Leu Ile Ala Glu Gly Ala Ala Lys Met Ser
    50                  55                  60

Ala Met Pro Ala Ala Ser Ser Gly Ala Ala Gly Val Thr Ala Ser
65                  70                  75                  80

Ala Ala Gly Asp Ala Ala Pro Ala Ala Ala Ala Lys Lys Asp Glu
                85                  90                  95

Pro Glu Glu Glu Ala Asp Asp Asp Met Gly Phe Gly Leu Phe Asp
            100                 105                 110
```

<210> SEQ ID NO 19
<211> LENGTH: 2936
<212> TYPE: DNA
<213> ORGANISM: Leishmania infantum

<400> SEQUENCE: 19

| | |
|---|---|
| gtcgacgccg cacctccgtc tctccccctc ctcgcccgcc atgcgtcgta tgtcgatgct | 60 |
| tccggtgggg gggtgcagtg aacgtagtcg atgatccatg ccgcgtcatc tctctataag | 120 |
| tacgtggcac atgcacctac acccaccacc accgttaccc atccacccct ggcaccgcat | 180 |
| gcacccgcca ctcgcggctt ttctctcttt ttgatctcac ccatcccacc ttgcccagta | 240 |
| ttgttcctct gcgactcccc gagtgttctc acgcacgcct cctcccacga tcgcttactt | 300 |
| tcgaatcttc gcttcaccat gtccaccaag tacctcgccg cgtacgctct ggcctccctg | 360 |

-continued

| | |
|---|---|
| agcaaggcgt ccccgtctca ggcggacgtg gaggctatct gcaaggccgt ccacatcgac | 420 |
| gtcgaccagg ccaccctcgc ctttgtgatg gagagcgtta cgggacgcga cgtggccacc | 480 |
| ctgatcgcgg agggcgccgc gaagatgagc gcgatgccgg cggccagctc tggtgccgct | 540 |
| gctggcgtca ctgcttccgc tgcgggtgat gcggcccgg ctgccgccgc cgcgaagaag | 600 |
| gacgagcccg aggaggaggc cgacgacgac atgggcttcg gtctgttcga ctaagcccat | 660 |
| cgacgcgttg tttgcgtgtg tgcgtgtatg taagggtgga tgcggggggc ttgctgtttc | 720 |
| ggtaaagttt cttctggcgt ggccccgcgt gcgcccagtc gttcccttga gggcatgaca | 780 |
| gaagcacacg aaaccggcat gcgcggctcc gtgactgaag aggggggcgc ccgtctctct | 840 |
| ttctgcgcgt gtgtcactca ttttttttt gccgtcttaa ctcacaggaa aacgccgccg | 900 |
| agatggtgtt gcggtgtctg atgtagggag gccaatcagg gatgaggatg gcacggttgg | 960 |
| tgctcacaac agcggaggca gcccttcaag acgcgtacgc ggtcctctct gtctttctca | 1020 |
| cgtgcatcca ccatcgcgcc caagcacgcg cccagcgaag gcgcacacgc gacgaacaga | 1080 |
| tgcgcggcgg atagcggaat ggaggaagag gaaggcgggt gggcgcacgc actgaaagct | 1140 |
| gcgagatagg cgagcaatga acgcgttgat gggtcgatcc cccttcctcg tgcagccctg | 1200 |
| tcgtccatgc ggggaggagg tggtgtcagc agcgcagcga aaaggatgga agcgagggag | 1260 |
| agagagagag agagacgtgc ataatctcgc gggcgggggc ggggaggagt gatgatggtg | 1320 |
| ctgatggacg ggcggagcac ggatggcgag cagtcggcgc atgcctgtct ctcttggcag | 1380 |
| tgcagcaccc ggtggagagt ctccctcctc caccctgccc cgcccttccc acattgctgg | 1440 |
| tccgccatgt gtgcacgcct gtgcctgtat gcctttacac gaaccttcc tactgttcct | 1500 |
| cacacgccca caactctatc gaacgtctcc tccccccccc cctcgacgca tccgtgctaa | 1560 |
| ccacacaacg cgcacacacg cacgcacgca atacacacac acgtatatct gcatatacgc | 1620 |
| atgccaccca ccgctgctcg ggtgtcgacg tggacgtaaa gctttctgtc tcgttttacg | 1680 |
| ccagtcgcac actctccacc atgtccacca agtacctcgc cgcgtacgct ctggcctccc | 1740 |
| tgagcaaggc gtccccgtct caggcggacg tggaggctat ctgcaaggcc gtccacatcg | 1800 |
| acgtcgacca ggccaccctc gccttttgtga tggagagcgt tacgggacgc gacgtggcca | 1860 |
| ccctgatcgc ggagggcgcc gcgaagatga gcgcgatgcc ggcggccagc tctggtgccg | 1920 |
| ctgctggcgt cactgcttcc gctgcgggtg atgcggcccc ggctgccgcc gccgcgaaga | 1980 |
| aggacgagcc cgaggaggag gccgacgacg acatgggctt cggtctgttc gactaagccc | 2040 |
| atcgacgcgt tggcagctgt gacatgtgac acggcggcgg tcctgcttct ctcctgccca | 2100 |
| ccttcatctt ctcggaagcc gagccgctta tcatctctct gtcttctcgc gcgcgcggct | 2160 |
| gccgcctctc tgtgagcatg cgtgcgtgta cgtcgtgtcg tcccatagcg agctgctggc | 2220 |
| gcgcgccgcg agagagagag agagagcacg aggcgcgggg gaagtggagg cgaatgggga | 2280 |
| atagagtggg ggccctgcgc acgggaaaag ccttctcccg gaaagtgata ccgacacatg | 2340 |
| cgtatgggag gaggggtgg gagaggatgc gagacgtcgt tgtctgcatc ctctccaacc | 2400 |
| ccaccccgc gtgtgtgcct gcacttattt ttcgttttc gataatttct tcgtcactta | 2460 |
| ccagcatctg gcatatatga catacctgca gacacacaag acaggcgcgc agcacacgac | 2520 |
| gacgggcgcc ggtgcggtgc cgacagacat gttcactgtg cctaacctgt gtatgcgtgt | 2580 |
| gtgtgtgtgt gtgtgtgtgt gtgcatgggt gggtgaatac gtctctctca cggcggtggt | 2640 |
| gcgacaacgc agacgcgatag ggagaggaga aggggcagg aggggcggc actcctcgtg | 2700 |
| cgcccgcttc ccgcgtcgcc gacctccact cccttgctca ctcactctcg ataccagtct | 2760 |

```
cgtggcggag aggaggcggg agtcactctg gatatcgccc tgtgagagcg gcccaacacg    2820
ctcacatgag ccccaccgct ctccatctca tctcctcacg gccatcacac atacgcacgc    2880
gccactgcct ctccttcaac ttcctcccac atgattgctt cgacgccact gtcgac       2936
```

<210> SEQ ID NO 20
<211> LENGTH: 323
<212> TYPE: PRT
<213> ORGANISM: Leishmania infantum

<400> SEQUENCE: 20

```
Met Pro Ser Ile Thr Thr Ala Lys Arg Glu Tyr Glu Glu Arg Leu Val
1               5                   10                  15

Asp Cys Leu Thr Lys Tyr Ser Cys Val Leu Phe Val Gly Met Asp Asn
            20                  25                  30

Val Arg Ser Gln Gln Val His Asp Val Gly Arg Ala Leu Arg Ala Lys
        35                  40                  45

Ala Glu Phe Met Met Gly Lys Lys Thr Leu Gln Gly Lys Ile Val Glu
    50                  55                  60

Lys Arg Ala Gln Ala Lys Asp Ala Ser Pro Glu Ala Lys His Phe Asn
65                  70                  75                  80

Asp Gln Cys Glu Glu Tyr Asn Leu Leu Ser Gly Asn Thr Gly Leu Ile
                85                  90                  95

Phe Thr Asn Asn Ala Val Gln Glu Ile Thr Ser Val Leu Asp Ala His
            100                 105                 110

Arg Val Lys Arg Ala Ala Arg Val Gly Ala Ile Ser Pro Cys Asp Val
        115                 120                 125

Ile Val Ala Ala Gly Ser Thr Gly Met Glu Pro Thr Gln Thr Ser Phe
    130                 135                 140

Phe Gln Ala Leu Asn Ile Ala Thr Lys Ile Ala Lys Gly Met Val Glu
145                 150                 155                 160

Ile Val Thr Glu Lys Lys Val Leu Ser Val Gly Asp Lys Val Asp Asn
                165                 170                 175

Ser Thr Ala Thr Leu Leu Gln Lys Leu Asn Ile Ser Pro Phe Tyr Tyr
            180                 185                 190

Gln Val Asn Val Leu Ser Val Trp Asp Arg Gly Val Leu Phe Thr Arg
        195                 200                 205

Glu Asp Leu Met Met Thr Glu Asp Met Val Glu Lys Met Leu Met Glu
    210                 215                 220

Gly Leu Ser Asn Val Ala Ala Met Ala Leu Gly Ala Gly Ile Pro Thr
225                 230                 235                 240

Ser Ser Thr Ile Gly Pro Met Leu Val Asp Ala Phe Lys Asn Leu Leu
                245                 250                 255

Ala Val Ser Val Ala Thr Ser Tyr Glu Phe Glu His Asn Gly Lys
            260                 265                 270

Glu Leu Arg Glu Ala Ala Ile Asn Gly Leu Leu Ala Gly Ser Cys Ser
        275                 280                 285

Ala Ala Ala Glu Pro Ala Ala Ala Pro Ala Ala Pro Ser Ala Ala
    290                 295                 300

Ala Lys Glu Glu Pro Glu Glu Ser Asp Glu Asp Asp Phe Gly Met Gly
305                 310                 315                 320

Gly Leu Phe
```

<210> SEQ ID NO 21
<211> LENGTH: 3790
<212> TYPE: DNA
<213> ORGANISM: Leishmania infantum

<400> SEQUENCE: 21

| | | | | | | |
|---|---|---|---|---|---|---|
| atgcgcgcgc | gcgcgcgaga | gagcatgtat | ccctgcgtgc | cttcaatgga | gacttgacac | 60 |
| ccctcttctc | tgctctctgc | tttctgctcc | gtccctaat | taccttgact | gccttttact | 120 |
| tgttcccttt | ctatttcctc | gggttttggc | aaccttcctt | atgcgcccaa | cacccacaac | 180 |
| atacccaccc | acaaatcgtt | gcttcacggc | ctcccctcgt | gctttgcagc | tccctttagc | 240 |
| aacgatgccg | tctatcacca | ctgccaagcg | cgagtacgag | gagcgcctcg | tcgactgcct | 300 |
| gaccaagtac | agctgcgtgc | tgttcgtggg | catggacaac | gtccgctcgc | agcaggtgca | 360 |
| cgatgtcggc | cgtgcgctgc | gcgcgaaggc | cgagttcatg | atgggcaaga | gacgctgca | 420 |
| gggcaagatc | gtggagaagc | gcgcgcaagc | caaggacgcg | agccccgagg | cgaagcactt | 480 |
| caacgatcag | tgtgaggagt | acaacctgct | gagcggcaac | accggcctca | tcttcacgaa | 540 |
| caacgctgtc | caggagatca | cgtctgtgct | tgacgcgcac | cgcgtgaagc | gcgcggcgcg | 600 |
| tgtcggagcg | atttccccgt | gtgacgtgat | tgtcgctgct | ggcagcaccg | gcatggagcc | 660 |
| gacccagacg | tccttcttcc | aggcgctgaa | cattgcgacg | aagattgcca | agggtatggt | 720 |
| ggagatcgtg | acggagaaga | aggtgctgag | cgtcggcgac | aaggtggaca | ctcgacggc | 780 |
| gacgctgctg | caaaagctga | acatcagccc | gttctactac | caggtgaatg | tgctgtccgt | 840 |
| gtgggaccgc | ggtgtgctgt | tcacccgcga | ggacctgatg | atgacggagg | acatggtgga | 900 |
| gaagatgctg | atggaaggcc | tgagcaacgt | tgcggcgatg | gcgctgggtg | ctggcatccc | 960 |
| gacgtcttcg | acgattggcc | cgatgctggt | ggacgccttc | aagaacctgc | tggctgtctc | 1020 |
| tgtggcgacc | tcgtacgagt | tcgaggagca | caacggcaag | gagctgcgcg | aggccgcgat | 1080 |
| caacggcctg | ctggccggct | cttgctcggc | tgctgcggag | cccgccgctg | ccgcgccggc | 1140 |
| cgcccctagc | gccgctgcca | aggaggagcc | ggaggagagc | gacgaggacg | acttcggcat | 1200 |
| gggcggtctc | ttctaagcga | ctcgccatct | cttagcctcc | ttgtggtgcg | cttgaggtgc | 1260 |
| tctcgctctg | cttctccttg | cagtgttggc | tgactctagc | gggtatgtgt | cgtcgcatta | 1320 |
| cacccacctc | tcccacccct | ttgctctacg | cgctcgcatg | cgcaatccgt | gaatcatcga | 1380 |
| gggaagtctc | tctgggtggc | agtgggtaag | cttgtgagga | aagaggtgtg | tgtgtgagcg | 1440 |
| ggcaggtacg | tcggaccact | taaacaaaca | aacacacaca | cacacggaaa | gactcacgta | 1500 |
| cagcatccgt | ccggcgcaac | agcaacgtcc | gccgcgcgaa | gcagagcgcg | tgcgctcatt | 1560 |
| gtaccgctgt | gaacggagga | gggggggact | cttcgctttt | ttcttttct | tttttttgtt | 1620 |
| tcggtagttt | attcttcatt | ttccgtctca | actcaaaaaa | cagcacaaaa | acgcggaaac | 1680 |
| gcagcatgag | tggcgccgtt | gcaatcgggg | acggtggcgg | cgcaacgcgt | cgtggcaact | 1740 |
| gcgcatgggt | tgctatctga | tggatggttg | cactgctgct | cgaacacagg | tggacctccc | 1800 |
| cccccccgc | aacgacgacg | tccggtcgag | tcgcgggcgt | gtggccgtga | gcacagggta | 1860 |
| gcctttcttt | gcgtcgcaca | gcacctatcg | tcgtcgtcgg | cactcctcat | cacatctccc | 1920 |
| tcgtgtcgca | cgaaggtgtg | ctgtctgtga | ggacgcttcc | gtgtgagtag | gtgcgtgcaa | 1980 |
| acatgcgtgc | atcggcaccg | gatcgcggtc | gggtaggttc | cacgctcctg | gagggtcgca | 2040 |
| agtgtcttgc | tgctccaggt | gactgatgac | caaggccata | tcctcacgca | acaccttcac | 2100 |
| tgctgccgcg | ctgctttcct | ccagcacgaa | gcgagcacag | gggcacgggt | ggggcggca | 2160 |

```
agcgagtagc ctctgaggtt gtgcgtaggc gacacgtcgt gtgccagtgg gcactgcgca    2220
ccttttcagt gttgtgtgtg gaacacaggg tcggcgcacg ctgtcttcgg tgatgctttc    2280
tcattatgag ccgcttgccg agcgtgcgcg cgaccccggg ccctcctca cctcctcgcg     2340 cggagttaac gcgtgcacgc tgtgtcccct gtgtaaagac agcttccccc accccttgt    2400 caactccctc tcggtccgtc tttctcgcgt tcattctctc ttcttcgtga acgaaacacg    2460
accactcgcc tcgcatattc cgcgtgccca atatcccact cactccctta cacatgcatt    2520
gtccgtgcca aacccggcg cacacttcgg cacacgaaaa acaccttccc cgaccccacg     2580
acagatagcc aaggctattg caagtctcac aagatgccgt ctatcaccac tgccaagcgc    2640
gagtacgagg agcgcctcgt cgactgcctg accaagtaca gctgcgtgct gttcgtgggc    2700
atggacaacg tccgctcgca gcaggtgcac gatgtcggcc gtgcgctgcg cgcgaaggcc    2760
gagttcatga tgggcaagaa gacgctgcag ggcaagatcg tggagaagcg cgcgcaagcc    2820
aaggacgcga gccccgaggc gaagcacttc aacgatcagt gtgaggagta caacctgctg    2880
agcggcaaca ccggcctcat cttcacgaac aacgctgtcc aggagatcac gtctgtgctt    2940
gacgcgcacc gcgtgaagcg cgcggcgcgt gtcggagcga tttccccgtg tgacgtgatt    3000
gtcgctgctg gcagcaccgg catggagccg acccagacgt ccttcttcca ggcgctgaac    3060
attgcgacga agattgccaa gggtatggtg gagatcgtga cggagaagaa ggtgctgagc    3120
gtcggcgaca aggtggacaa ctcgacgcg acgctgctgc aaaagctgaa catcagcccg     3180
ttctactacc aggtgaatgt gctgtccgtg tgggaccgcg gtgtgctgtt cacccgcgag    3240
gacctgatga tgacggagga catggtggag aagatgctga tggaaggcct gagcaacgtt    3300
gcggcgatgg cgctgggtgc tggcatcccg acgtcttcga cgattggccc gatgctggtg    3360
gacgccttca agaacctgct ggctgtctct gtggcgacct cgtacgagtt cgaggagcac    3420
aacggcaagg agctgcgcga ggccgcgatc aacggcctgc tggccggctc ttgctcggct    3480
gctgcggagc ccgccgctgc cgcgccggcc gcccctagcg ccgctgccaa ggaggagccg    3540
gaggagagcg acgaggacga cttcggcatg gcggtctctt tctaagcgac tcgccatctc    3600
ccactgagca ccgtcgagtg ttcgtgtgtt cgcagggtgg acagcggcga gcgtgtgatg    3660
cccttggatc atcaggaagc aactctctcc ctttctctct gtgttcttcg tttcttcttt    3720
cattagtttt ggatcgccgt gcgctgcgca tcgctcagtt ctcatttata tcaataacaa    3780
caacgaagac                                                          3790
```

<210> SEQ ID NO 22
<211> LENGTH: 260
<212> TYPE: PRT
<213> ORGANISM: Leishmania major

<400> SEQUENCE: 22

Met Gly Lys Thr Val Leu Ser Cys Arg Lys Gly Asn Gly Ser Val Tyr
1               5                   10                  15

Gln Val His Gly His Lys Arg Leu Gly Pro Ala Lys Leu Arg Ile Leu
            20                  25                  30

Asp Tyr Ala Glu Arg His Gly Tyr Met Arg Gly Val Val Lys Ser Ile
        35                  40                  45

Glu His Glu Ala Gly Arg Gly Ala Ala Leu Ala Arg Val Glu Phe Arg
    50                  55                  60

His Pro Tyr Lys Phe Arg Arg Val Lys Glu Leu Met Val Ala Pro Glu
65                  70                  75                  80

Gly Met Phe Thr Gly Gln Ser Val Phe Cys Gly Gln Lys Ala Pro Leu
            85                  90                  95

Ala Ile Gly Asn Val Leu Pro Leu Gly Gln Ile Thr Glu Gly Cys Ile
        100                 105                 110

Val Cys Asn Val Glu Ala Lys Pro Gly Asp Arg Gly Thr Leu Ala Arg
    115                 120                 125

Ala Ser Gly Asp Tyr Cys Ile Ile Ser His Asn His Glu Thr Gly
130                 135                 140

Arg Thr Arg Leu Lys Leu Pro Ser Gly Gln Lys Lys Ser Val Pro Ser
145                 150                 155                 160

Thr Ser Arg Ala Met Ile Gly Ile Ser Gly Gly Arg Ile Glu
                165                 170                 175

Lys Pro Val Leu Lys Ala Gly Asn Ser Phe Tyr Arg Phe Arg Gly Lys
                180                 185                 190

Arg Asn Cys Trp Pro Lys Val Arg Gly Val Ala Arg Asn Pro Val Glu
            195                 200                 205

His Pro His Gly Gly Gly Asn His Gln His Ile Gly His Pro Ser Thr
            210                 215                 220

Val Ser Arg His Ser Pro Pro Gly Gln Lys Val Gly Leu Ile Ala Ala
225                 230                 235                 240

Arg Arg Thr Gly Arg Ile Arg Gly Gly Lys Ala Val Lys Gly Ala Trp
                245                 250                 255

His Pro Glu Glu
            260

<210> SEQ ID NO 23
<211> LENGTH: 783
<212> TYPE: DNA
<213> ORGANISM: Leishmania major

<400> SEQUENCE: 23
atgggtaaga ctgtgctgag ctgccgtaag gcaacggct ccgtgtacca ggtgcacggc      60
cacaagcgcc ttggccccgc caagctgcgc attctggact acgccgagcg ccacggctac    120
atgcgcggtg tggtgaagtc gatcgagcac gaggctggcc gcgtgcggc gctggcgcgc     180 gtggagttcc gccacccgta caagttccgc cgcgtgaagg agctgatggt ggcgccggag    240
ggcatgttca ccggccagtc ggtgttctgc ggccagaagg ccccgctcgc gatcggcaac    300
gtgctgcccc ttggccagat cacggagggc tgcattgtgt gcaacgtgga ggcgaagccc    360
ggtgaccgcg gcacgctggc gcgcgcgtcc ggcgactact gcatcatcat ctcgcacaac    420
cacgagacag gccgcacgcg cctgaagctg ccgagcgggc agaagaagtc cgtgccgagc    480
acgagccgcg cgatgatcgg catcatcagc ggcggtggcc gcatcgagaa gcccgtgctg    540
aaggccggta actcgttcta ccgcttccgc ggcaagcgca actgctgcc caaggtgcgt    600 ggtgttgccc gcaacccggt ggagcacccg cacgtggtg gtaaccatca gcacattggc    660
cacccgtcga cggtgtcgcg ccactcgccg ccgggccaga aggtgggtct gatcgctgcc    720
cgtcgcaccg gccgtattcg cggtggtaag gctgtcaagg gcgcgtggca cccggaggag    780
taa                                                                    783

<210> SEQ ID NO 24
<211> LENGTH: 252
<212> TYPE: PRT
<213> ORGANISM: Leishmania major

<400> SEQUENCE: 24

```
Met Ala Thr His Ser Val Tyr Gly Asn Ala Ser Asp Met Pro Ala Val
1               5                   10                  15

Pro Ala Pro Glu Ser Ala Ile Lys Arg Ala Ala Phe Lys Gln Gln Gln
                20                  25                  30

Thr Glu Ser Phe Lys Lys Ala Val Ala Arg Lys Ala Ala Lys Ala
            35                  40                  45

Ala Leu Lys Lys Thr Ala Tyr Leu Arg Ala Arg Lys Tyr Ser Arg Glu
    50                  55                  60

Tyr Arg Gly Ala Glu Lys Lys Leu Val Thr Leu Arg Arg Gln Ala Ala
65                  70                  75                  80

Ser His Gly Asn Tyr Tyr Leu Glu Ala Lys Pro Lys Val Ala Val Val
                85                  90                  95

Thr Arg Ile Arg Gly Ile Ala Lys Val Asn Pro Lys Gln Arg Lys Ile
                100                 105                 110

Leu Gln Leu Leu Arg Leu Arg Gln Ile Phe Asn Thr Val Phe Val Lys
            115                 120                 125

Met Asn Lys Pro Met Glu Asn Met Leu Arg Ala Val Glu Pro Tyr Ile
130                 135                 140

Ala Tyr Gly Tyr Pro Ser Leu Ala Thr Val Arg Ala Met Val Tyr Lys
145                 150                 155                 160

Arg Gly Tyr Leu Lys Ile Asn Gly Gln Arg Val Lys Ile Thr Asp Asn
                165                 170                 175

Gln Met Ile Lys Asp Lys Tyr Asn Asn Val Asp Ile Val Cys Ala Glu
            180                 185                 190

Asp Met Val Asn Gln Ile Tyr Thr Cys Gly Lys His Phe Arg Thr Val
        195                 200                 205

Thr His Gly Met Trp Pro Phe Lys Leu Ala Pro Ala Gly Gly Met
    210                 215                 220

Arg Gln Lys Arg Arg His Phe Val Glu Gly Gly Asp Tyr Gly Asn Arg
225                 230                 235                 240

Asp Thr Leu Ile Asn Arg Phe Leu Ala Arg Met Ile
                245                 250
```

<210> SEQ ID NO 25
<211> LENGTH: 759
<212> TYPE: DNA
<213> ORGANISM: Leishmania major

<400> SEQUENCE: 25

```
atggccacac actcagttta cggcaacgca tccgacatgc ccgctgtccc tgcccctgag      60
tccgcgatca gcgtgctgc gttcaagcag cagcagacgg agagcttcaa gaaggccgtg     120
gtggccagaa aggctgccaa ggctgccctg aagaagaccg cctacctgcg tgcccgcaaa    180
tactcccgcg agtaccgcgg tgcggagaag aagctggtga cgctgcgccg ccaggccgcc    240
tctcacggta actactacct ggaggcgaag ccgaaggttg ccgtggtgac tcgcatccgc    300
ggtatcgcca aggtgaaccc gaagcagcgc aagattcttc agttgctgcg cctgcgccag    360
atcttcaaca cggtgtttgt gaagatgaac aagccgatgg agaacatgct gcgtgcggtg    420
gagccctaca tcgcgtacgg ctacccgtcc ctggccaccg tccgcgcgat ggtgtacaag    480
cgcggctacc tgaagatcaa cggccagcgc gtgaagatca ccgacaacca gatgatcaag    540
gataagtaca acaacgtgga cattgtgtgt gccgaggata tggtgaacca gatctacacc    600
tgcggcaagc acttccgcac ggtgacgcac ggcatgtggc ccttcaagct ggccccctcg    660
```

```
gccggtggca tgcgccagaa gcgccgtcac ttcgtggagg gtggcgacta tggtaaccgc    720
gacaccttga tcaaccgctt cctcgcccgc atgatctga                          759
```

<210> SEQ ID NO 26
<211> LENGTH: 264
<212> TYPE: PRT
<213> ORGANISM: Leishmania major

<400> SEQUENCE: 26

```
Met Pro Gly Lys Glu Val Lys Lys Val Thr Gln Pro Ala Lys Ala Ala
1               5                   10                  15

Ser Pro Tyr Lys Lys Pro Ala Val Ala Ser His Phe Ala Arg Pro
            20                  25                  30

Lys Asn Phe Gly Ile Gly Gln Asp Val Pro Tyr Ala Arg Asp Leu Ser
            35                  40                  45

Arg Phe Met Arg Trp Pro Thr Phe Val Thr Met Gln Arg Lys Lys Arg
    50                  55                  60

Val Leu Gln Arg Arg Leu Lys Val Pro Pro Ala Leu Asn Gln Phe Thr
65                  70                  75                  80

Lys Val Leu Asp Arg Ala Ser Arg Asn Glu Ala Leu Lys Leu Ile Lys
                85                  90                  95

Lys Tyr Ala Pro Glu Thr Arg Lys Ala Arg Arg Glu Arg Leu Gln Lys
            100                 105                 110

Val Ala Glu Glu Lys Lys Lys Asp Pro Lys Lys Thr Val Ser Thr Lys
        115                 120                 125

Ala Pro Leu Ala Val Val Thr Gly Leu Gln Glu Val Thr Arg Ala Ile
    130                 135                 140

Glu Lys Lys Gln Ala Arg Met Val Val Ile Ala Asn Asn Val Asp Pro
145                 150                 155                 160

Val Glu Leu Val Leu Trp Met Pro Asn Leu Cys Arg Ala Asn Lys Ile
                165                 170                 175

Pro Tyr Ala Ile Val Lys Asp Met Ala Arg Leu Gly Asp Ala Ile Gly
            180                 185                 190

Arg Lys Thr Ala Thr Cys Val Ala Leu Thr Asp Val Asn Ala Glu Asp
        195                 200                 205

Glu Ala Thr Leu Lys Asn Leu Ile Arg Ser Val Asn Ala Arg Phe Leu
    210                 215                 220

Ser Arg Ser Asp Val Ile Arg Arg Gln Trp Gly Gly Leu Gln Leu Ser
225                 230                 235                 240

Leu Arg Ser Arg Ala Glu Leu Arg Lys Lys His Ala Arg Asn Ala Gly
                245                 250                 255

Val Asp Ala Ala Ala Ile Ile Gln
            260
```

<210> SEQ ID NO 27
<211> LENGTH: 795
<212> TYPE: DNA
<213> ORGANISM: Leishmania major

<400> SEQUENCE: 27

```
atgcccggca aggaagtgaa gaaggtgacg cagcccgcga aggccgcgtc tccgtacaag    60
aagcccgccg ttgcgtcgca tttcgcggcc cgcccgaaga acttcggtat tggccaggat    120
```

-continued

```
gtgccgtacg cgcgtgacct gtcccgcttc atgcggtggc cgacgttcgt gacgatgcag    180
cgcaagaagc gcgtgctgca gcgccgcctg aaggtgccgc cggcgctgaa ccagttcacg    240
aaggtgctgg accgcgcgag ccgaaacgag gcgctgaagc tgattaagaa gtacgcgccg    300
gagacccgca aggctcgccg cgagcgcctg cagaaggttg ccgaggagaa gaagaaggac    360
ccgaagaaga cggtatcgac gaaggctccc ctggctgttg tgaccggtct gcaggaggtg    420
acgcgcgcga tcgagaagaa gcaggctcgc atggttgtga tcgcgaacaa cgtgaccct    480
gtggagctcg tgctgtggat gccgaacctg tgccgcgcga acaagatccc gtatgccatc    540
gtgaaggaca tggcgcgcct gggcgatgcg atcgggcgga agacggcgac gtgcgttgcg    600
ctcaccgacg tgaacgccga ggatgaggcg acgctgaaga acctgatccg ctccgtgaac    660
gctcgcttct tgtcccgctc ggacgtgatc cgccgccagt ggggtggtct gcagctgtct    720
ctgcgatccc gcgcggagct gcgcaagaag catgcccgca cgctggtgt ggacgccgcg    780
gccatcatcc agtaa                                                    795
```

<210> SEQ ID NO 28
<211> LENGTH: 222
<212> TYPE: PRT
<213> ORGANISM: Leishmania major

<400> SEQUENCE: 28

Met Ala Phe Pro Ser Arg Lys Asp Ala Phe Arg Ala Gln Arg Lys Gly
1               5                   10                  15

Ala Lys Lys His Arg Pro Glu Ile Ile Val Ile Asp Leu Lys Asp His
                20                  25                  30

Val Leu Gly Arg Ala Ala Ala Val Ala Lys Gln Leu Leu Leu Gly
            35                  40                  45

Lys Lys Ile Thr Val Val Arg Cys Glu Gln Leu Asn Ile Ala Gly Thr
    50                  55                  60

Glu Ile Arg Asn Lys Ile Lys Tyr Leu Gln Tyr Leu Arg Lys Arg Lys
65                  70                  75                  80

Leu Thr Asn Pro Thr Lys Gly Pro Phe His His Arg Ala Pro Ser Asp
                85                  90                  95

Val Phe Val Arg Thr Val Arg Ser Met Leu Pro Arg Tyr Thr Lys Arg
            100                 105                 110

Gly Met Lys Ala Leu Asn Ser Leu Val Ala Tyr Glu Gly Ile Pro Pro
        115                 120                 125

Asn Val Val Arg Thr Gly Gly Arg Val Val Ile Pro Arg Ala Gln Arg
    130                 135                 140

His Val Cys Tyr Arg Ser Glu Arg Pro Tyr Thr Val Leu Gly Asn Met
145                 150                 155                 160

Cys Lys His Val Gly Trp Lys Tyr Ser Asp Val Val Ala Asn Leu Glu
                165                 170                 175

Lys Ala Arg Val Glu Lys Ala Ser Arg His His Glu Lys Gln Ala Lys
            180                 185                 190

Leu Arg Asp Ala Trp Lys Ser Ala Arg Lys Glu Ala Leu Ala Lys Met
        195                 200                 205

Pro Lys His Asn Val Glu Val Leu Lys Lys Phe Gly Tyr Ala
    210                 215                 220

<210> SEQ ID NO 29
<211> LENGTH: 669
<212> TYPE: DNA
<213> ORGANISM: Leishmania major

<400> SEQUENCE: 29

```
atggcctttc ctagccgcaa ggatgcgttc cgcgcgcagc gcaagggcgc caagaagcac      60
cgccccgaga tcatcgtgat cgacctgaag gatcacgtgc ttggtcgcgc ggcggctgtg     120
gttgccaagc agctgctcct gggtaagaag atcaccgtgg tgcgctgcga gcagctcaac     180
attgccggta cggagatccg caacaagatc aagtacctgc agtacctgcg caagcggaag     240
ctgacgaacc ccacaaaggg tcccttccac caccgtgccc cgtccgacgt gtttgtccgc     300
actgtgcgca gcatgctgcc ccggtacacg aagcgcggca tgaaggcgct taactcgctg     360
gtggcctacg agggaattcc gcccaacgtg gtgcgcacgg gcgggcgcgt ggtgatcccg     420
cgcgcccagc gccatgtgtg ctaccgctcg agcgtccttt acacagtgct cggcaacatg     480
tgcaagcacg tgggctggaa gtacagcgac gtcgtcgcca atctcgagaa ggctcgcgtg     540
gagaaggcgt cccgccacca cgaaaagcag gcgaagcttc gcgacgcgtg gaagtcggcc     600
cgcaaggagg cgctcgccaa gatgcccaag cacaacgtgg aggtgctgaa gaagtttggc     660
tacgcgtag                                                              669
```

<210> SEQ ID NO 30
<211> LENGTH: 267
<212> TYPE: PRT
<213> ORGANISM: Leishmania major

<400> SEQUENCE: 30

```
Met Thr Pro Leu Ser Leu Ser Ser Arg His Ser Phe Lys Gln Asn
1               5                   10                  15

Glu Thr Gln Asn Met Val Ser Leu Lys Leu Gln Ala Arg Leu Ala Ser
            20                  25                  30

Ser Ile Leu Gly Cys Gly Arg Ala Arg Val Trp Leu Asp Pro Asn Glu
        35                  40                  45

Ala Val Glu Ile Gln Asn Ala Asn Ser Arg Lys Ser Val Arg Lys Leu
    50                  55                  60

Ile Lys Asp Gly Phe Ile Ile Arg Lys Pro Val Lys Val His Ser Arg
65                  70                  75                  80

Ala Arg Trp Arg Lys Met Lys Glu Ala Lys Asp Met Gly Arg His Asn
                85                  90                  95

Gly Val Gly Arg Arg Glu Gly Ser Arg Glu Ala Arg Met Pro Ser Lys
            100                 105                 110

Glu Leu Trp Met Arg Arg Leu Arg Ile Leu Arg Arg Leu Leu Arg Lys
        115                 120                 125

Tyr Arg Ala Asp Lys Lys Ile Asp Arg His Val Tyr Arg Asp Leu Tyr
    130                 135                 140

Met Arg Ala Lys Gly Asn Val Phe Arg Asn Lys Arg Asn Leu Val Glu
145                 150                 155                 160

His Ile His Lys Ile Lys Asn Glu Lys Lys Glu Arg Gln Leu Ala
                165                 170                 175

Glu Gln Leu Ala Ala Lys His Leu Arg Asp Glu Gln Asn Arg Asn Lys
            180                 185                 190

Ala Arg Lys Gln Glu Leu Lys Lys Arg Glu Lys Glu Arg Glu Arg Ala
        195                 200                 205

Arg Arg Asp Asp Ala Ala Ala Ala Gln Lys Lys Ala Asp Ala
    210                 215                 220

Ala Lys Lys Ser Ala Ala Pro Ala Ala Lys Ser Ala Ala Pro Ala Ala
225                 230                 235                 240
```

```
Lys Ala Ala Ala Pro Ala Thr Lys Ala Ala Ala Pro Ala Thr
                245                 250                 255

Lys Gly Ala Ala Pro Val Lys Lys Ser Lys Lys
        260                 265
```

<210> SEQ ID NO 31
<211> LENGTH: 804
<212> TYPE: DNA
<213> ORGANISM: Leishmania major

<400> SEQUENCE: 31

```
atgacccctc tctccctctc ttcctcccgc cacagtttta agcagaacga aacgcagaac      60
atggtgtctc tgaagctgca ggctcgcctt gcgtcgagca tcctcggctg cggccgcgcc     120
cgcgtgtggc tggaccccaa cgaggcggtg gagatccaga cgcgaactc gcgcaagagc      180
gtgcgcaagc tgatcaagga tggcttcatc atccgcaagc cggtgaaggt gcactcgcgc     240
gcgcggtggc gtaaaatgaa ggaggcgaag gacatggggc gccacaacgg cgttgggcgc     300
cgcgagggta gccgcgaggc cgcatgccg agcaaggagt tgtggatgcg ccgcctgcgc      360
attctgcgcc gcctgctgcg caagtaccgc gcggacaaga agattgaccg ccacgtgtac     420
cgcgacctgt acatgcgcgc gaaggggtaac gtgttccgca acaagcgcaa ccttgtggag    480
cacatccaca agatcaagaa tgagaagaag aaggagcgcc agctggcgga gcagctcgcg    540
gcgaagcacc tgcgcgacga gcagaaccgc aacaaggctc gcaagcagga gctgaagaag   600
cgcgagaagg agcgcgagcg cgcgaggcgc gacgacgctg ctgccgctgc gcagaagaag   660
aaggcggacg ccgcgaagaa gtccgccgcg cctgctgcga gtccgccgc gcctgccgcg    720
aaggctgctg ccccccgccac gaaggccgct gctgctgccc ccgccacgaa gggtgctgcg   780
ccggtgaaga agtcgaagaa gtaa                                           804
```

<210> SEQ ID NO 32
<211> LENGTH: 273
<212> TYPE: PRT
<213> ORGANISM: Leishmania major

<400> SEQUENCE: 32

```
Met Ala Lys Lys His Leu Lys Arg Leu Tyr Ala Pro Lys Asp Trp Met
1               5                   10                  15

Leu Ser Lys Leu Thr Gly Val Phe Ala Pro Arg Pro Arg Pro Gly Pro
            20                  25                  30

His Lys Leu Arg Glu Cys Leu Pro Leu Leu Val Ile Ile Arg Asn Arg
        35                  40                  45

Leu Lys Tyr Ala Leu Asn Ala Arg Glu Gly Glu Met Ile Leu Arg Gln
    50                  55                  60

Gly Leu Val His Val Asp Asn His Pro Arg Arg Asp Gly Lys Tyr Pro
65                  70                  75                  80

Ala Gly Phe Met Asp Val Val Glu Ile Pro Lys Thr Gly Asp Arg Phe
                85                  90                  95

Arg Leu Met Tyr Asp Val Lys Gly Arg Phe Ala Leu Val Asn Leu Ser
            100                 105                 110

Glu Ala Glu Ala Gln Ile Lys Leu Met Lys Val Asn Leu Tyr Thr
        115                 120                 125

Ala Thr Gly Arg Val Pro Val Ala Val Thr His Asp Gly His Arg Ile
    130                 135                 140

Arg Tyr Pro Asp Pro His Thr Ser Ile Gly Asp Thr Ile Val Tyr Asn
145                 150                 155                 160
```

-continued

```
Val Lys Glu Lys Lys Cys Val Asp Leu Ile Lys Asn Arg Gln Gly Lys
            165                 170                 175

Ala Val Ile Val Thr Gly Gly Ala Asn Arg Gly Arg Ile Gly Glu Ile
        180                 185                 190

Val Lys Val Glu Cys His Pro Gly Ala Phe Asn Ile Ala His Leu Lys
    195                 200                 205

Asp Ala Ser Gly Ala Glu Phe Ala Thr Arg Ala Ala Asn Ile Phe Val
210                 215                 220

Ile Gly Lys Asp Leu Asn Asn Leu Gln Val Thr Val Pro Lys Gln Gln
225                 230                 235                 240

Gly Leu Arg Met Asn Val Ile Gln Glu Arg Glu Arg Leu Ile Ala
                245                 250                 255

Ala Glu Ala Arg Lys Asn Ala Pro Ala Arg Gly Ala Arg Arg Ala Arg
            260                 265                 270

Lys
```

<210> SEQ ID NO 33
<211> LENGTH: 822
<212> TYPE: DNA
<213> ORGANISM: Leishmania major

<400> SEQUENCE: 33

```
atggccaaga agcacctcaa gcgcttgtat gcgcccaagg actggatgct gagcaagctg      60
accggcgtgt tcgcgccgcg tccgcgtccg ggtccgcaca agctgcgcga gtgcctgccg     120
ctgctggtga tcatccgcaa ccggctgaag tacgcgctga cgcgcgcga gggtgagatg     180
atcctgcgcc agggtctggt gcacgtggac aaccaccgc gccgcgacgg caagtatccc     240
gccggtttca tggacgtggt cgagatcccg aagacgggcg accgcttccg cctgatgtac     300
gacgtcaagg gccgcttcgc gttggtgaac ctgtccgagg cggaggcgca gatcaagctg     360
atgaaggttg tgaacctgta cacggccacc ggccgcgtgc cggtcgctgt gacgcacgac     420
ggccaccgca tccgctaccc ggacccgcac acctccattg gtgacaccat cgtgtacaac     480
gtcaaggaga agaagtgcgt ggacctgatc aagaaccgcc agggcaaggc cgtgatcgtg     540
accggtggcg ccaaccgcgg ccgcatcggc gagatcgtga aggtggagtg ccaccccggt     600
gcgttcaaca ttgcgcacct gaaggacgcg tccggcgccg agttcgccac ccgcgccgcg     660
aacatcttcg tgatcggcaa ggacctgaac aacctgcagg taacggtgcc gaagcagcag     720
ggcctgcgca tgaacgtgat ccaggagcgc gaggagcgcc tgatcgcggc ggaggcccgc     780
aagaacgcgc cggctcgtgg tgcccgcagg gcccgcaagt ga                      822
```

<210> SEQ ID NO 34
<211> LENGTH: 249
<212> TYPE: PRT
<213> ORGANISM: Leishmania major

<400> SEQUENCE: 34

```
Met Lys Leu Asn Ile Ala Tyr Pro Arg Asn Gly Thr Val Lys Gln Phe
1               5                  10                  15

Glu Ile Ser Asp Glu Val Leu Arg Arg Val Gln Leu Gln Asp Tyr Arg
                20                  25                  30

Leu Gly Asn Glu Val Asp Gly Ala Ile Phe Gly Ser Glu Phe Lys Gly
            35                  40                  45

Tyr Ile Phe Arg Leu Arg Gly Gly Ser Asp Lys Asp Gly Phe Pro Met
        50                  55                  60
```

```
Val Pro Gly Val Leu Ala Ser Ser Arg Val Ser Leu Leu Val Lys Arg
 65                  70                  75                  80

Gly Ala Ile Gly Phe Asn Thr Phe Arg Gly Tyr Gln Gly Glu Arg Arg
                 85                  90                  95

Arg Lys Asn Val Arg Gly Cys Val Leu Ala Ser Asp Ile Ala Leu Val
            100                 105                 110

Asn Val Thr Ile Ser Lys Val Gly Asp Gln Pro Ile Glu Gly Val Thr
        115                 120                 125

Asp Thr Thr Ala Pro Arg Arg Leu Gly Pro Lys Arg Ala Ser Lys Ile
    130                 135                 140

Arg Lys Leu Phe Asn Leu Ser Arg Thr Glu Asp Val Arg Lys Tyr Val
145                 150                 155                 160

Val Arg Arg Arg Val Val Lys Ser Gly Lys Lys Asp Arg Leu Lys Ala
                165                 170                 175

Pro Lys Ile Gln Arg Leu Ile Thr Pro Arg Val Lys Ala Arg Arg Ala
            180                 185                 190

Lys Lys Ala Lys Asp Ala Ile Ala Lys Val Arg Ala Ser Ala Ala Glu
        195                 200                 205

Arg Arg Glu Tyr Leu Arg Leu Ile Ala Ser Asn Arg Arg Ala Leu Arg
    210                 215                 220

Gln Arg Asp His Ser Lys Lys His Thr Arg Lys Val His Ala Gln Arg
225                 230                 235                 240

Ala Glu Val Ala Ala Phe Gln Lys Lys
                245

<210> SEQ ID NO 35
<211> LENGTH: 750
<212> TYPE: DNA
<213> ORGANISM: Leishmania major

<400> SEQUENCE: 35
atgaagctca acatcgcgta cccccgcaac gggacggtga agcagttcga gatctcggac      60
gaggtgctcc gccgcgtgca gctgcaggac taccgcctcg caacgaggt ggacggcgcc     120 atctttggta gcgagttcaa gggctacatc ttccgcctgc gcgtggctc ggacaaggat     180 ggtttcccga tggtccctgg cgtgcttgcc tccagccgtg tgtcgctgct ggtgaagcgc     240
ggtgcgatcg gcttcaacac cttccgcggc taccagggtg agcgccgccg caagaacgtt     300
cgcggctgcg tgctcgcgag cgacattgcg ctggtgaacg tgaccatctc caaggtcggt     360
gaccagccga tcgagggtgt gacggacacc acggctcccc gccgtctggg tccgaagcgc     420
gcgagcaaga tccgcaagct cttcaacctg tcccgcaccg aagacgtgcg gaagtacgtt     480
gttcgccgcc gcgtcgtgaa gagcggcaag aaggaccggc tgaaggcccc gaagatccag     540
cgtctgatca cgccgagggt caaggcccgc cgtgccaaga aggccaagga cgccatcgcc     600
aaggtgcgcg cgtctgccgc tgagcgccgt gagtacctgc gccttatcgc ctcgaaccgc     660
cgtgcgctgc gccagcgtga ccactccaag aagcacaccc ggaaggtgca cgcccagcgc     720
gctgaggtgg cagcattcca gaagaagtaa                                      750

<210> SEQ ID NO 36
<211> LENGTH: 1436
<212> TYPE: DNA
<213> ORGANISM: artificial
<220> FEATURE:
<223> OTHER INFORMATION: protein Q
```

<400> SEQUENCE: 36

```
atgagaggat ctcaccatca ccatcaccat acggatccgc atgcgagctc gaacaacaac      60
aacaataaca ataacaacaa cctcgggatc gagggaaggc ctttagctac tcctcgcagc     120
gccaagaagg ccgtccgcaa gagcggctcc aagtccgcga aatgtggtct gatcttcccg     180
gtgggccgcg tcggcgggat gatgcgccgc ggccagtacg ctcgccgcat cggtgcctct     240
ggcgccccca ggatttcaga attctccgtg aaggcggccg cgcagagcgg aagaagcgg      300
tgccgcctga acccgcgcac cgtgatgctg gccgcgcgcc acgacgacga catcggcacg     360
cttctgaaga acgtgacctt gtctcacagc ggcgttgtgc cgaacatcag caaggcgatg     420
gcaaagaaga agggcggcaa gaagggcaag gcgacaccga gcgcgcccga attcggatcc     480
tctagaccca tgtccaccaa gtacctcgcc gcgtacgctc tggcctccct gagcaaggcg     540
tccccgtctc aggcggacgt ggaggctatc tgcaaggccg tccacatcga cgtcgaccag     600
gccaccctcg cctttgtgat ggagagcgtt acgggacgcg acgtggccac cctgatcgcg     660
gagggcgccg cgaagatgag cgcgatgccg gcggccagct ctggtgccgc tgctggcgtc     720
actgcttccg ctgcgggtga tgcggctccg gctgccgccg ccgcgaagaa ggacgagccc     780
gaggaggagg ccgacgacga catgggcccc tctagagtcg accccatgca gtacctcgcc     840
gcgtacgccc tcgtggcgct gtctggcaag acgccgtcga aggcggacgt tcaggctgtc     900
ctgaaggccg ccggcgttgc cgtggatgcc tcccgcgtgg atgccgtctt ccaggaggtg     960
gagggcaaga gcttcgatgc gctggtggcc gagggccgca cgaagctggt gggctctggc    1020
tctgccgctc ctgctggcgc tgtctccact gctggtgccg ccgctggcgc ggtggccgag    1080
gcgaagaagg aggagcccga ggaggaggag gccgatgatg acatgggccc cgtcgacctg    1140
cagcccgccg ctgccgcgcc ggccgcccct agcgccgctg ccaaggagga gccggaggag    1200
agcgacgagg acgacttcgg catgggcggt ctcttctaag cgactcgcca tctcttagcc    1260
tccttgtggt gcgcttgagg tgctctcgct ctgcttctcc ttgcagtgtt ggctgactct    1320
ggcgggtatg tgccgtcgca ttacacccac ctctcccacc cctttgccct acgcgctcgc    1380
atgcgcaatc cgtgaatcat cgagggaagt ctctctgggt ggcagtgggt aagctt        1436
```

<210> SEQ ID NO 37
<211> LENGTH: 412
<212> TYPE: PRT
<213> ORGANISM: artificial
<220> FEATURE:
<223> OTHER INFORMATION: protein Q

<400> SEQUENCE: 37

```
Met Arg Gly Ser His His His His His His Thr Asp Pro His Ala Ser
1               5                   10                  15

Ser Asn Asn Asn Asn Asn Asn Asn Asn Asn Leu Gly Ile Glu Gly
            20                  25                  30

Arg Pro Leu Ala Thr Pro Arg Ser Ala Lys Lys Ala Val Arg Lys Ser
        35                  40                  45

Gly Ser Lys Ser Ala Lys Cys Gly Leu Ile Phe Pro Val Gly Arg Val
    50                  55                  60

Gly Gly Met Met Arg Arg Gly Gln Tyr Ala Arg Arg Ile Gly Ala Ser
65                  70                  75                  80

Gly Ala Pro Arg Ile Ser Glu Phe Ser Val Lys Ala Ala Ala Gln Ser
                85                  90                  95
```

Gly Lys Lys Arg Cys Arg Leu Asn Pro Arg Thr Val Met Leu Ala Ala
             100                 105                 110

Arg His Asp Asp Asp Ile Gly Thr Leu Leu Lys Asn Val Thr Leu Ser
        115                 120                 125

His Ser Gly Val Val Pro Asn Ile Ser Lys Ala Met Ala Lys Lys Lys
    130                 135                 140

Gly Gly Lys Lys Gly Lys Ala Thr Pro Ser Ala Pro Glu Phe Gly Ser
145                 150                 155                 160

Ser Arg Pro Met Ser Thr Lys Tyr Leu Ala Tyr Ala Leu Ala Ser
                165                 170                 175

Leu Ser Lys Ala Ser Pro Ser Gln Ala Asp Val Glu Ala Ile Cys Lys
            180                 185                 190

Ala Val His Ile Asp Val Asp Gln Ala Thr Leu Ala Phe Val Met Glu
        195                 200                 205

Ser Val Thr Gly Arg Asp Val Ala Thr Leu Ile Ala Glu Gly Ala Ala
    210                 215                 220

Lys Met Ser Ala Met Pro Ala Ala Ser Ser Gly Ala Ala Ala Gly Val
225                 230                 235                 240

Thr Ala Ser Ala Ala Gly Asp Ala Ala Pro Ala Ala Ala Ala Ala Lys
                245                 250                 255

Lys Asp Glu Pro Glu Glu Ala Asp Asp Met Gly Pro Ser Arg
            260                 265                 270

Val Asp Pro Met Gln Tyr Leu Ala Ala Tyr Ala Leu Val Ala Leu Ser
                275                 280                 285

Gly Lys Thr Pro Ser Lys Ala Asp Val Gln Ala Val Leu Lys Ala Ala
290                 295                 300

Gly Val Ala Val Asp Ala Ser Arg Val Asp Ala Val Phe Gln Glu Val
305                 310                 315                 320

Glu Gly Lys Ser Phe Asp Ala Leu Val Ala Glu Gly Arg Thr Lys Leu
                325                 330                 335

Val Gly Ser Gly Ser Ala Ala Pro Ala Gly Ala Val Ser Thr Ala Gly
            340                 345                 350

Ala Ala Ala Gly Ala Val Ala Glu Ala Lys Lys Glu Glu Pro Glu Glu
        355                 360                 365

Glu Glu Ala Asp Asp Asp Met Gly Pro Val Asp Leu Gln Pro Ala Ala
    370                 375                 380

Ala Ala Pro Ala Ala Pro Ser Ala Ala Ala Lys Glu Glu Pro Glu Glu
385                 390                 395                 400

Ser Asp Glu Asp Asp Phe Gly Met Gly Gly Leu Phe
                405                 410

<210> SEQ ID NO 38
<211> LENGTH: 21
<212> TYPE: DNA
<213> ORGANISM: Artificial
<220> FEATURE:
<223> OTHER INFORMATION: primer

<400> SEQUENCE: 38
aacacgaagg agggcaaggt c                                            21

<210> SEQ ID NO 39
<211> LENGTH: 22
<212> TYPE: DNA
<213> ORGANISM: Artificial
<220> FEATURE:
<223> OTHER INFORMATION: primer

```
<400> SEQUENCE: 39
cttcttcgcg gcctttgcct tg                                    22

<210> SEQ ID NO 40
<211> LENGTH: 22
<212> TYPE: DNA
<213> ORGANISM: Artificial
<220> FEATURE:
<223> OTHER INFORMATION: primer

<400> SEQUENCE: 40
tgcacgctgg caaattgggt ac                                    22

<210> SEQ ID NO 41
<211> LENGTH: 20
<212> TYPE: DNA
<213> ORGANISM: Artificial
<220> FEATURE:
<223> OTHER INFORMATION: primer

<400> SEQUENCE: 41
cttcttcgtg cgcacagcag                                       20

<210> SEQ ID NO 42
<211> LENGTH: 22
<212> TYPE: DNA
<213> ORGANISM: Artificial
<220> FEATURE:
<223> OTHER INFORMATION: primer

<400> SEQUENCE: 42
cttcttcgcg gcctttgcct tg                                    22

<210> SEQ ID NO 43
<211> LENGTH: 20
<212> TYPE: DNA
<213> ORGANISM: Artificial
<220> FEATURE:
<223> OTHER INFORMATION: primer

<400> SEQUENCE: 43
cttcttcgtg cgcacagcag                                       20

<210> SEQ ID NO 44
<211> LENGTH: 29
<212> TYPE: DNA
<213> ORGANISM: Artificial
<220> FEATURE:
<223> OTHER INFORMATION: primer

<400> SEQUENCE: 44
cgggatccat gtctcactgc aagttcgag                             29

<210> SEQ ID NO 45
<211> LENGTH: 28
<212> TYPE: DNA
<213> ORGANISM: Artificial
<220> FEATURE:
<223> OTHER INFORMATION: primer

<400> SEQUENCE: 45
aactgcagtt acttcttcgc ggcctttg                              28
```

-continued

```
<210> SEQ ID NO 46
<211> LENGTH: 28
<212> TYPE: DNA
<213> ORGANISM: Artificial
<220> FEATURE:
<223> OTHER INFORMATION: primer

<400> SEQUENCE: 46
cgggatccat gtgcacgctg gcaaattg                                        28

<210> SEQ ID NO 47
<211> LENGTH: 29
<212> TYPE: DNA
<213> ORGANISM: Artificial
<220> FEATURE:
<223> OTHER INFORMATION: primer

<400> SEQUENCE: 47
cccaagcttt tacttgccga ggcgctcgc                                       29

<210> SEQ ID NO 48
<211> LENGTH: 419
<212> TYPE: PRT
<213> ORGANISM: Leishmania infantum

<400> SEQUENCE: 48

Met Ser His Cys Lys Phe Glu His Pro Arg Gly His Leu Gly Phe
1               5                   10                  15

Leu Pro Arg Lys Arg Ser Arg Gln Ile Arg Gly Arg Ala Arg Ala Phe
                20                  25                  30

Pro Lys Asp Asp Ala Thr Gln Lys Pro His Leu Thr Ser Phe Met Val
            35                  40                  45

Phe Lys Ala Gly Met Thr His Ile Val Arg Asp Val Asp Arg Pro Gly
    50                  55                  60

Ser Lys Val Asn Lys Lys Glu Val Val Glu Pro Val Thr Ile Leu Glu
65                  70                  75                  80

Ala Pro Pro Met Val Ile Val Gly Ile Val Gly Tyr Arg Gln Thr Pro
                85                  90                  95

Val Gly Leu Lys Thr Ile Gly Thr Val Trp Ala His His Thr Ser Val
            100                 105                 110

Glu Phe Arg Arg Arg Tyr Tyr Lys Asn Trp Lys Gln Ser Ala Gln Leu
        115                 120                 125

Ala Phe Ser Arg Gln Lys Gln Phe Ala Asn Thr Lys Glu Gly Lys Val
    130                 135                 140

Ala Glu Ala Arg Thr Leu Asn Ala Phe Ala Lys Lys Ala Ser Val Ile
145                 150                 155                 160

Arg Val Ile Ala His Thr Gln Leu Arg Lys Leu Arg Asn His Arg Val
                165                 170                 175

Gly Val Lys Lys Ala His Val Gln Glu Ile Gln Val Asn Gly Gly Ser
            180                 185                 190

Val Ala Ala Lys Ile Ala Leu Ala Lys Ser Leu Leu Glu Lys Glu Val
        195                 200                 205

Arg Val Asp Ser Val Phe Gln Gln Ser Glu Ala Cys Asp Val Cys Ser
    210                 215                 220

Val Thr Lys Gly His Gly Thr Glu Gly Val Val Lys Arg Trp Gly Val
225                 230                 235                 240

Ala Cys Leu Pro Arg Lys Thr His Arg Gly Leu Arg Lys Val Ala Cys
                245                 250                 255
```

```
Ile Gly Ala Trp His Pro Arg Val Met Tyr Thr Val Ala Arg Ala
            260                 265                 270

Gly Gln His Gly Tyr His His Arg Thr Gln Leu Asn Lys Lys Ile Tyr
        275                 280                 285

Gln Ile Gly Arg Ser Val Ala Val Glu Pro Asn Gln Ala Thr Thr Thr
290                 295                 300

Tyr Asp Leu Thr Ala Lys Thr Ile Thr Pro Met Gly Gly Phe Val Gly
305                 310                 315                 320

Tyr Gly Thr Val Arg Asn Asp Tyr Val Met Leu Lys Gly Ser Val Ser
                325                 330                 335

Gly Pro Arg Arg Arg Val Met Thr Leu Arg Arg Pro Met Ala Pro Gln
            340                 345                 350

Thr Ser Arg His Leu Lys Glu Lys Ile Val Leu Lys Phe Ile Asp Thr
        355                 360                 365

Ser Ser Lys Ile Gly His Gly Arg Phe Gln Thr Lys Lys Glu Lys Asn
    370                 375                 380

Gln Trp Phe Gly Pro Leu Lys Lys Asp Arg Ile Arg Arg Glu Glu Arg
385                 390                 395                 400

Leu Arg Lys Glu Arg Ala Ala Arg Ala Val Glu Arg Lys Ala Lys Val
                405                 410                 415

Ala Lys Lys

<210> SEQ ID NO 49
<211> LENGTH: 1260
<212> TYPE: DNA
<213> ORGANISM: Leishmania infantum

<400> SEQUENCE: 49
atgtctcact gcaagttcga gcaccccgc cacggccatc tcggcttcct gccgcgcaag      60
cgctcgcgcc agatccgcgg ccgcgcgcgc gcgttcccca aggacgacgc gacgcagaag     120
ccccacctga cgagtttcat ggtgttcaag gccggcatga cgcacattgt gcgtgatgtc     180
gatcgccctg gatcgaaggt gaacaagaag gaggtggtgg agccggtgac gattctggag     240
gcgccgccga tggtgattgt cggcattgtg ggctaccgcc aaacgccggt cggcctgaag     300
acgatcggca ccgtgtgggc gcaccacacg agcgtcgagt ccgccgccg ctactacaag     360 aactggaagc agtctgcgca actggccttc tcccgccaga gcagtttgc gaacacgaag     420 gagggcaagg tcgccgaggc gcgcacgctg aacgcgttcg cgaagaaggc gtccgtcatc     480
cgcgtgatcg cgcacacgca gctgcgcaag cttcgcaacc accgcgtggg cgtgaagaag     540
gcgcacgtgc aggagatcca ggtcaacggc ggcagcgttg cggcgaagat cgcgctggcc     600
aagtccctgc tggagaagga ggtgcgcgtg gactccgtgt ccagcagtc ggaggcgtgc     660 gacgtgtgct ccgtgacgaa aggccacggt acggagggcg tggtgaagcg ctggggcgtt     720
gcctgcctgc cacgcaagac gcaccgcggt ctgcgcaagg ttgcgtgcat cggcgcgtgg     780
caccctgccc gcgtcatgta cactgtcgcg cgcgccggtc agcacggtta ccaccaccgc     840
acgcagctga caagaagat ctaccagatc ggccgctccg ttgctgtgga accgaaccag     900
gcgacgacga cctacgatct gacggccaag acgatcacac ccatgggtgg cttcgtcggc     960
tacggcacgg tgcgcaacga ctacgtgatg ctgaagggct ccgtgtctgg tccgcgccgc    1020
cgtgtgatga cgctccgccg cccgatggca ccgcagacgt cgcgccacct gaaggagaag    1080
atcgtgctga agttcatcga cactagctcg aagattggcc acggccgctt ccagacgaag    1140
```

```
aaggagaaga accagtggtt cggcccgctc aagaaggacc gcatccgccg cgaggagcgc    1200
ctgcgcaagg agcgcgctgc ccgcgccgtg gagcgcaagg caaaggtcgc gaagaagtaa    1260
```

<210> SEQ ID NO 50
<211> LENGTH: 419
<212> TYPE: PRT
<213> ORGANISM: Leishmania mexicana

<400> SEQUENCE: 50

```
Met Ser His Cys Lys Phe Glu His Pro Arg His Gly His Leu Gly Phe
1               5                   10                  15

Leu Pro Arg Lys Arg Ser Arg Gln Ile Arg Gly Arg Ala Arg Ala Phe
            20                  25                  30

Pro Lys Asp Asp Ala Thr Gln Lys Pro His Leu Thr Ser Phe Met Val
        35                  40                  45

Phe Lys Ala Gly Met Thr His Ile Val Arg Asp Val Asp Arg Pro Gly
    50                  55                  60

Ser Lys Val Asn Lys Lys Glu Val Val Glu Pro Val Thr Ile Leu Glu
65                  70                  75                  80

Ala Pro Pro Met Val Ile Val Gly Ile Val Gly Tyr Arg Gln Thr Pro
                85                  90                  95

Val Gly Leu Lys Thr Ile Gly Thr Val Trp Ala His His Thr Ser Val
            100                 105                 110

Glu Phe Arg Arg Arg Tyr Tyr Lys Asn Trp Lys Gln Ser Ala Gln Leu
        115                 120                 125

Ala Phe Ser Arg Gln Lys Gln Phe Ala Asn Thr Lys Glu Gly Arg Ile
    130                 135                 140

Ala Glu Ala Arg Thr Leu Asn Ala Phe Ala Lys Ala Ser Val Ile
145                 150                 155                 160

Arg Val Ile Ala His Thr Gln Leu Arg Lys Leu Arg Asn His Arg Val
                165                 170                 175

Gly Val Lys Lys Ala His Val Gln Glu Ile Gln Ile Asn Gly Gly Asn
            180                 185                 190

Val Ala Ala Lys Ile Ala Leu Ala Lys Ser Leu Leu Glu Lys Glu Val
        195                 200                 205

Arg Val Asp Ser Val Phe Gln Gln Ser Glu Ala Cys Asp Val Cys Ser
    210                 215                 220

Val Thr Lys Gly His Gly Thr Glu Gly Val Val Lys Arg Trp Gly Val
225                 230                 235                 240

Ala Cys Leu Pro Arg Lys Thr His Arg Gly Leu Arg Lys Val Ala Cys
                245                 250                 255

Ile Gly Ala Trp His Pro Ala Arg Val Met Tyr Thr Val Ala Arg Ala
            260                 265                 270

Gly Gln His Gly Tyr His His Arg Thr Gln Leu Asn Lys Lys Ile Tyr
        275                 280                 285

Gln Ile Gly Arg Ser Val Ala Val Glu Pro Asn Gln Ala Thr Thr Thr
    290                 295                 300

Tyr Asp Leu Thr Ala Lys Thr Ile Thr Pro Met Gly Gly Phe Val Gly
305                 310                 315                 320

Tyr Gly Thr Val Arg Asn Asp Tyr Val Met Leu Lys Gly Ser Val Ser
                325                 330                 335

Gly Pro Arg Arg Arg Val Met Thr Leu Arg Arg Pro Met Ala Pro Gln
            340                 345                 350
```

Thr Ser Arg Gln Leu Lys Glu Lys Ile Val Leu Lys Phe Ile Asp Thr
            355                 360                 365

Ser Ser Lys Ile Gly His Gly Arg Phe Gln Thr Lys Lys Glu Lys Ser
        370                 375                 380

Gln Trp Phe Gly Pro Leu Lys Lys Asp Arg Ile Arg Arg Glu Arg
385                 390                 395                 400

Leu Arg Lys Glu Arg Ala Ala Arg Ala Val Glu Arg Lys Ala Lys Ala
                405                 410                 415

Ala Lys Lys

<210> SEQ ID NO 51
<211> LENGTH: 1260
<212> TYPE: DNA
<213> ORGANISM: Leishmania mexicana

<400> SEQUENCE: 51

```
atgtctcact gcaagttcga gcaccccgc cacggccatc tcggcttcct gccgcgcaag      60
cgctcgcgcc agatccgcgg ccgcgcgcgc gcgttcccca aggacgacgc gacgcagaag    120
ccccacctaa cgagcttcat ggtgttcaag gctggcatga cgcacattgt gcgtgatgtc    180
gaccgccctg gatcgaaggt gaacaagaag gaggtggtgg agccggtgac gatcctggag    240
gcgccgccga tggtgattgt cggcattgtg ggctaccgcc aaacgccggt tggcctgaag    300
acgatcggca ccgtgtgggc gcaccacacg agcgtggagt ccgccgccg ctactacaag     360
aactggaagc agtctgcgca gctggccttc tcccgccaga agcagttcgc gaacacgaag    420
gagggcagga tcgctgaggc gcgcacgctg aacgcgttcg cgaagaaggc gtccgtcatc    480
cgcgtgatcg cgcacacgca gctgcgcaag cttcgcaacc accgcgtggg cgtgaagaag    540
gcgcacgtgc aggagatcca gatcaacggc ggcaacgttg cggcgaagat cgcgctggcc    600
aagtccctgc tggagaagga ggtgcgcgtc gactccgtgt ccagcagtc ggaggcgtgc     660
gacgtgtgct ccgtgacgaa aggtcacggt acggagggcg tggtgaagcg ctggggcgtt    720
gcctgcctgc cgcgcaagac acaccgcggc ctgcgcaagg tggcgtgcat cggcgcgtgg    780
caccctgccc gcgtcatgta cactgtcgcg cgcgccggtc agcacggcta ccaccaccgc    840
acgcagctga caagaagat ctaccagatc ggccgctccg ttgctgtgga gccgaaccag     900
gcgacgacga cctacgatct gacggccaag acgatcacgc ccatgggcgg cttcgtcggc    960
tacggtacgg tgcgcaacga ctacgtgatg ctgaagggct ccgtgtctgg cccgcgccgc   1020
cgtgtgatga cgctgcgacg cccgatggcg ccgcagacgt cgcgccagct gaaggagaag   1080
atcgtgctga gttcatcga cacgagctcg aagatcggcc acggccgctt ccagacgaag   1140
aaggagaaga gccagtggtt cggcccgctc aagaaggacc gcatccgccg cgaggagcgc   1200
ctgcgcaagg agcgcgctgc ccgcgccgtg gagcgcaagg caaaggccgc gaagaagtaa   1260
```

<210> SEQ ID NO 52
<211> LENGTH: 305
<212> TYPE: PRT
<213> ORGANISM: Leishmania infantum

<400> SEQUENCE: 52

Met Pro Phe Val Lys Val Val Lys Asn Lys Ala Tyr Phe Lys Arg Phe
1               5                   10                  15

Gln Val Lys Tyr Arg Arg Arg Arg Glu Gly Lys Thr Asp Tyr His Ala
                20                  25                  30

```
Arg Arg Gln Met Val Leu Gln Asp Lys Thr Lys Phe Gly Ser Pro Lys
            35                  40                  45
Tyr Arg Leu Val Val Arg Ile Thr Asn Lys Asp Ile Ile Ala Gln Ile
 50                  55                  60
Val Gln Ala Lys Ile Val Gly Asp Glu Val Val Met Ala Ala Tyr Ala
 65                  70                  75                  80
His Glu Leu Pro Ala Phe Gly Ile Glu His Gly Leu Thr Asn Tyr Ala
                 85                  90                  95
Ala Ala Tyr Ala Thr Gly Leu Leu Leu Ala Arg Arg Thr Leu Ala Lys
                100                 105                 110
Leu Gly Ile Ala Asp Lys Phe Gln Gly Ala Lys Glu Ala Asp Gly Ser
            115                 120                 125
Tyr Ser Ala Val Arg Thr Lys Lys Asp Asp Glu Gly Asp Asp Glu Glu
130                 135                 140
Arg Phe Pro Phe Lys Ala Ile Leu Asp Val Gly Leu Ala Arg Thr Thr
145                 150                 155                 160
Thr Gly Ala Arg Val Phe Gly Val Leu Lys Gly Ala Val Asp Gly Gly
                165                 170                 175
Met Ala Val Pro His Arg Pro Asn Arg Phe Pro Gly Tyr Asn Lys Glu
            180                 185                 190
Lys Ser Ser Leu Asp Ala Lys Val His Arg Asp Arg Ile Phe Gly Lys
            195                 200                 205
His Val Ala Glu Tyr Leu Lys Gln Val Lys Glu Ala Ser Ser Asn
            210                 215                 220
Pro Asp Glu Lys Cys Val Gln Phe Ser Arg Tyr Met Ala Ala Lys Val
225                 230                 235                 240
Leu Pro Glu Ser Ile Glu Gly Met Tyr Lys Lys Ala His Ala Ile
                245                 250                 255
Arg Ala Asp Pro Ser Lys Ser Leu Pro Lys Lys Ala Lys Lys Glu Gly
            260                 265                 270
Val Ala His Lys Ser Tyr Lys Thr Lys Lys Leu Ser Gly Ala Glu Lys
            275                 280                 285
Arg Ala Ala Ala Lys Ala Lys Val Ala Ala Ile Arg Glu Arg Leu Gly
 290                 295                 300
Lys
305

<210> SEQ ID NO 53
<211> LENGTH: 918
<212> TYPE: DNA
<213> ORGANISM: Leishmania infantum

<400> SEQUENCE: 53
atgccgttcg tcaaggtcgt gaagaacaag gcgtacttca gcgcttcca ggtgaagtac      60 cgccgtcgcc gcgagggcaa gacggactac cacgcgcgcc gccagatggt gctgcaggac    120
aagacgaagt tcggctcgcc caagtaccgc cttgttgtgc gcatcacgaa caaggacatc    180
attgcgcaga tcgtgcaggc gaagatcgtc ggcgacgagg tggtgatggc cgcgtacgcg    240
cacgagctgc ctgcgttcgg cattgagcac ggcctgacaa actacgctgc tgcgtacgcg    300
actggtctgc tgctggcgcg ccgcacgctg gcgaagctgg gcatcgcgga caagttccag    360
ggcgcgaagg aggcggacgg ctcgtactct gctgtgcgca cgaagaagga cgacgagggc    420
gacgacgagg agcgcttccc gttcaaggcg atcctggacg tcgggcttgc cgcacgacg    480 accggcgccc gcgtgttcgg cgtgctgaag ggcgcggtgg acggcggtat ggctgtgccg    540
```

```
caccgcccca accgcttccc cggctacaac aaggagaaga gctcgctgga cgcgaaggtg      600
caccgcgacc gcatctttgg caagcacgtg gcggagtacc tgaagcaggt gaaggaggag      660
gcgagctcga accccgacga gaagtgcgtg cagttctcga ggtacatggc cgcgaaggtt      720
ttgccggaga gcatcgaggg catgtacaag aaggcgcacg cggcgatccg cgcggacccg      780
tcgaagtcgc tgccgaagaa ggcgaagaag gagggcgtcg cgcacaagag ctacaagacg      840
aagaagctga gcggcgcgga agagggcc gccgcgaagg cgaaggtcgc ggccatccgc      900
gagcgcctcg gcaagtaa                                                   918
```

```
<210> SEQ ID NO 54
<211> LENGTH: 305
<212> TYPE: PRT
<213> ORGANISM: Leishmania mexicana

<400> SEQUENCE: 54
```

Met Pro Phe Val Lys Val Val Lys Asn Lys Ala Tyr Phe Lys Arg Phe
 1               5                  10                  15

Gln Val Lys Tyr Arg Arg Arg Glu Gly Lys Thr Asp Tyr His Ala
            20                  25                  30

Arg Arg Gln Met Val Leu Gln Asp Lys Thr Lys Phe Gly Ser Pro Lys
        35                  40                  45

Tyr Arg Leu Val Val Arg Ile Thr Asn Lys Asp Ile Ile Ala Gln Ile
    50                  55                  60

Val Gln Ala Lys Ile Val Gly Asp Glu Val Val Met Ala Ala Tyr Ala
65                  70                  75                  80

His Glu Leu Pro Ala Phe Gly Ile Glu His Gly Leu Thr Asn Tyr Ala
                85                  90                  95

Ala Ala Tyr Ala Thr Gly Leu Leu Leu Ala Arg Arg Thr Leu Ala Lys
            100                 105                 110

Leu Gly Ile Ala Asp Lys Phe Gln Gly Ala Lys Glu Ala Asp Gly Ser
        115                 120                 125

Tyr Ser Ala Val Arg Thr Lys Lys Asp Asp Glu Gly Asp Glu Glu
    130                 135                 140

Arg Phe Pro Phe Lys Ala Ile Leu Asp Val Gly Leu Ala Arg Thr Thr
145                 150                 155                 160

Thr Gly Ala Arg Val Phe Gly Val Leu Lys Gly Ala Val Asp Gly Gly
                165                 170                 175

Met Ala Val Pro His Arg Pro Asn Arg Phe Pro Gly Tyr Asn Lys Glu
            180                 185                 190

Lys Ser Ser Leu Asp Ala Lys Val His Arg Asp Arg Ile Phe Gly Lys
        195                 200                 205

His Val Ala Glu Tyr Leu Lys Gln Val Lys Glu Ala Ser Ser Asn
    210                 215                 220

Pro Asp Glu Lys Cys Val Gln Phe Ser Lys Tyr Met Ala Ala Lys Val
225                 230                 235                 240

Leu Pro Glu Ser Ile Glu Gly Met Tyr Lys Lys Ala His Ala Ala Ile
                245                 250                 255

Arg Ala Asp Pro Ser Lys Ser Leu Pro Lys Lys Ala Lys Lys Glu Ser
            260                 265                 270

Val Ala His Lys Ser Tyr Lys Thr Lys Lys Leu Ser Gly Ala Glu Lys
        275                 280                 285

```
Arg Ala Ala Ala Lys Ala Lys Val Ala Ala Ile Arg Glu Arg Leu Gly
        290                 295                 300

Lys
305
```

<210> SEQ ID NO 55
<211> LENGTH: 918
<212> TYPE: DNA
<213> ORGANISM: Leishmania mexicana

<400> SEQUENCE: 55

```
atgccgttcg tcaaggtcgt gaagaacaag gcgtacttca agcgctttca ggtgaagtac      60
cgccgtcgcc gcgagggcaa gacggactac cacgcgcgcc gccagatggt gctgcaggac     120
aagacgaagt tggctcgcc caagtaccgc cttgttgtgc gcatcacgaa caaggacatc      180
attgcgcaga tcgtgcaggc gaagatcgtc ggcgacgagg tggtgatggc cgcgtacgcg     240
cacgagctgc ctgcgttcgg gattgagcac ggcctgacaa actacgccgc tgcgtacgcg     300
actgggctgc tgctggcgcg ccgcacgctg gcgaagctgg gcatcgcgga caagttccag     360
ggcgcgaagg aggcggacgg ctcgtactct gctgtgcgca cgaagaagga cgacgagggc     420
gacgacgagg agcgcttccc gttcaaggcg atcctggacg tcggcctcgc gcgcacgacg     480
accggtgccc gcgtgttcgg cgtgctgaag ggcgcggtgg acggcggtat ggctgtgccg     540
caccgccccca accgcttccc cggctacaac aaggagaaga gctcactgga cgcgaaggtg     600
caccgcgacc gcatctttgg caagcacgtt gcggagtacc tgaagcaggt gaaggaggag     660
gcgagctcga accccgacga gaagtgcgtg cagttctcga agtacatggc cgcgaaggtt     720
ttgccggaga gcatcgaggg catgtacaag aaggcgcacg cggcgatccg cgcggacccg     780
tcgaagtcgc tgccgaagaa ggcgaagaag gagagcgtcg cgcacaagag ctacaagacg     840
aagaagctga gcggcgcgga aagagggcc gccgcgaagg cgaaggtcgc ggccatccgc     900
gagcgcctcg gcaagtaa                                                   918
```

<210> SEQ ID NO 56
<211> LENGTH: 305
<212> TYPE: PRT
<213> ORGANISM: Leishmania braziliensis

<400> SEQUENCE: 56

```
Met Pro Phe Val Lys Val Val Lys Asn Lys Ala Tyr Phe Lys Arg Phe
1               5                  10                  15

Gln Val Lys Tyr Arg Arg Arg Glu Gly Lys Thr Asp Tyr His Ala
            20                  25                  30

Arg Arg Gln Met Val Leu Gln Asp Lys Thr Lys Phe Gly Ser Pro Lys
        35                  40                  45

Tyr Arg Leu Val Val Arg Thr Thr Asn Lys Asp Ile Ile Ala Gln Ile
    50                  55                  60

Val Gln Ala Lys Ile Ala Gly Asp Glu Val Leu Met Ala Ala Tyr Ala
65                  70                  75                  80

His Glu Leu Pro Ala Phe Gly Ile Glu His Gly Leu Thr Asn Tyr Ala
                85                  90                  95

Ala Ala Tyr Ala Thr Gly Leu Leu Leu Ala Arg Arg Thr Leu Ala Lys
            100                 105                 110

Leu Gly Ile Ala Asp Lys Phe Gln Gly Ala Lys Glu Ala Asp Gly Ser
        115                 120                 125
```

```
Tyr Ser Ala Val Arg Thr Lys Lys Asp Asp Gln Gly Asp Asp Glu Ala
            130                 135                 140

Arg Phe Pro Phe Lys Ala Ile Leu Asp Val Gly Leu Ala Arg Thr Thr
145                 150                 155                 160

Thr Gly Ala Arg Val Phe Gly Val Leu Lys Gly Ala Val Asp Gly Gly
                165                 170                 175

Ile Ser Val Pro His Arg Pro Asn Arg Phe Pro Gly Tyr Ser Lys Glu
                180                 185                 190

Lys Ser Ala Leu Asp Ala Lys Val His Arg Asp Arg Ile Phe Gly Lys
                195                 200                 205

His Val Ala Glu Tyr Leu Lys Gln Val Lys Glu Glu Ala Ser Ser Asn
            210                 215                 220

Pro Asp Glu Lys Cys Val Gln Phe Ser Lys Tyr Met Glu Ala Lys Val
225                 230                 235                 240

Ala Pro Glu Ser Ile Glu Cys Met Tyr Lys Lys Ala His Ala Ala Ile
                245                 250                 255

Arg Ala Asp Pro Ser Lys Ser Leu Pro Lys Ala Lys Lys Glu Gly
                260                 265                 270

Ala Lys His Lys Ser Tyr Lys Thr Lys Lys Met Ser Gly Ala Glu Lys
                275                 280                 285

Arg Ala Ala Ala Lys Ala Lys Val Ala Ala Ile Arg Glu Arg Leu Gly
            290                 295                 300

Lys
305

<210> SEQ ID NO 57
<211> LENGTH: 29
<212> TYPE: DNA
<213> ORGANISM: artificial
<220> FEATURE:
<223> OTHER INFORMATION: primer

<400> SEQUENCE: 57
cgggatccat gtctcactgc aagttcgag                                           29

<210> SEQ ID NO 58
<211> LENGTH: 30
<212> TYPE: DNA
<213> ORGANISM: artificial
<220> FEATURE:
<223> OTHER INFORMATION: primer

<400> SEQUENCE: 58
gcgatatctc ccttcttcgc ggcctttgcc                                          30

<210> SEQ ID NO 59
<211> LENGTH: 32
<212> TYPE: DNA
<213> ORGANISM: artificial
<220> FEATURE:
<223> OTHER INFORMATION: primer

<400> SEQUENCE: 59
gcgatatcgg gatggccaag aagcacctca ag                                       32

<210> SEQ ID NO 60
<211> LENGTH: 28
<212> TYPE: DNA
<213> ORGANISM: artificial
<220> FEATURE:
<223> OTHER INFORMATION: primer
```

<400> SEQUENCE: 60
cggaattctc ccttgcgggc cctgcggg                                          28

<210> SEQ ID NO 61
<211> LENGTH: 32
<212> TYPE: DNA
<213> ORGANISM: artificial
<220> FEATURE:
<223> OTHER INFORMATION: primer

<400> SEQUENCE: 61
cggaattcgg gatgaagctc aacatcgcgt ac                                     32

<210> SEQ ID NO 62
<211> LENGTH: 32
<212> TYPE: DNA
<213> ORGANISM: artificial
<220> FEATURE:
<223> OTHER INFORMATION: primer

<400> SEQUENCE: 62
gcgatatctc ccttcttctg gaatgctgcc ac                                     32

<210> SEQ ID NO 63
<211> LENGTH: 31
<212> TYPE: DNA
<213> ORGANISM: artificial
<220> FEATURE:
<223> OTHER INFORMATION: primer

<400> SEQUENCE: 63
gcgatatcgg gatgtgcacg ctggcaaatt g                                      31

<210> SEQ ID NO 64
<211> LENGTH: 34
<212> TYPE: DNA
<213> ORGANISM: artificial
<220> FEATURE:
<223> OTHER INFORMATION: primer

<400> SEQUENCE: 64
ggggtaccgg atccttactt gccgaggcgc tcgc                                   34

<210> SEQ ID NO 65
<211> LENGTH: 918
<212> TYPE: DNA
<213> ORGANISM: Leishmania braziliensis

<400> SEQUENCE: 65
atgccgttcg tcaaggtcgt gaagaacaag gcgtacttca agcgcttcca ggtgaagtac        60
cgccgtcgcc gcgagggcaa gacggactac cacgcacgcc gccagatggt gctgcaggac       120
aagacgaagt ttggctcacc caagtaccgc cttgttgtgc gcacgacgaa caaggacatc       180
attgcgcaga tcgtgcaggc gaagatcgcc ggcgacgagg tgctgatggc tgcgtacgcg       240
cacgagctgc ctgcgttcgg gattgagcac ggcctgacga actacgctgc ggcgtacgcg       300
acgggcctgc tgctggcgcg ccgcacgctg gcgaagttgg gcatcgcgga caagttccag       360
ggcgcgaagg aggcggacgg ctcgtactct gctgtgcgca cgaagaagga cgaccagggc       420
gacgacgagg cgcgcttccc gttcaaggcg atcctggacg ttggtcttgc gcgcacgacg       480
acgggtgccc gcgtgttcgg cgtgctgaag ggcgctgtgg acggcggcat ctcggtgccg       540
caccgcccca accgcttccc cggctacagc aaggagaaga gcgccctgga cgcgaaggtg       600

| | |
|---|---|
| caccgtgacc gcatcttcgg caagcacgtt gcggagtacc tgaagcaggt gaaggaggag | 660 |
| gcgagctcga accctgacga gaagtgcgtg cagttctcga agtacatgga ggcgaaggtt | 720 |
| gcgccagaga gcatcgagtg catgtacaag aaggcacacg cggcgatccg cgcggacccg | 780 |
| tcgaagtcgc tgccgaagaa ggcgaagaag gagggcgcca agcacaagag ctacaagacg | 840 |
| aagaagatga gcggcgcgga aagagggcc gccgcgaagg cgaaggtcgc cgccattcgc | 900 |
| gagcgccttg gcaagtga | 918 |

<210> SEQ ID NO 66
<211> LENGTH: 3846
<212> TYPE: DNA
<213> ORGANISM: Artificial
<220> FEATURE:
<223> OTHER INFORMATION: Chimeric DNA encoding L3-S4-S6-L5

<400> SEQUENCE: 66

| | |
|---|---|
| atgtctcact gcaagttcga gcaccccgc cacggccatc tcggcttcct gccgcgcaag | 60 |
| cgctcgcgcc agatccgcgg ccgtgcgcgc gcgttcccca aggacgacgc gacgcagaag | 120 |
| ccccacctga cgagcttcat ggtgttcaag gccggtatga cgcacattgt gcgtgatgtc | 180 |
| gatcgccctg gatcgaaggt gaacaagaag gaagtggtgg agccggtgac gatcctggag | 240 |
| gcgccgccga tggtgattgt cggcattgtg ggctaccgcc aaacgccggt tggcctgaag | 300 |
| acgatcggca ccgtgtgggc gcaccacacg agcgtcgagt ccgccgccg ctactacaag | 360 |
| aactggaagc agtctgcgca actggccttc tcccgccaga gcagtttgc gaacacgaag | 420 |
| gagggcaagg tcgccgaggc gcgcacgctg aacgcgttcg cgaagaaggc gtccgtcatc | 480 |
| cgcgtgatcg cgcacacgca gctgcgcaag cttcgcaacc accgcgtggg cgtgaagaag | 540 |
| gcgcacgtgc aggagatcca ggtcaacggc ggcagcgttg cggcgaagat cgcgctggcc | 600 |
| aagtccctgc tggagaagga ggtgcgcgtc gactccgtgt ccagcagtc cgaggcgtgc | 660 |
| gacgtgtgct ccgtcacgaa aggccacggt acggagggcg tggtgaagcg ctggggcgtt | 720 |
| gcctgcctgc cacgcaagac gcaccgcggt ctgcgcaagg ttgcgtgcat cggcgcgtgg | 780 |
| cacccctgccc cgcgtcatgta cactgtcgcg cgcgccggtc agcacggtta ccaccaccgc | 840 |
| acgcagctga caagaagat ctaccagatc ggccgctccg ttgctgtgga gccgaaccag | 900 |
| gcgacgacga cctacgatct gacagccaag acgatcacgc ccatgggtgg cttcgtcggc | 960 |
| tacggtacgg tgcgcaacga ctacgtgatg ctgaagggct ccgtgtctgg cccgcgccgc | 1020 |
| cgtgtgatga cgctgcgccg cccgatggcg ccgcagacgt cgcgccagct gaaggagaag | 1080 |
| atcgtgctga agttcatcga cacgagctcg aagatcggcc acggccgctt ccagacgaag | 1140 |
| aaggagaaga accagtggtt cggcccgctc aagaaggacc gcatccgccg cgaggagcgc | 1200 |
| ctgcgcaagg agcgcgctgc ccgcgccgtg gagcgcaagg caaaggccgc gaagaaggga | 1260 |
| gatatcggga tggccaagaa gcacctcaag cgcttgtatg cgcccaagga ctggatgctg | 1320 |
| agcaagctga ccggcgtgtt cgcgccgcgt ccgcgtccgg gtccgcacaa gctgcgcgag | 1380 |
| tgcctgccgc tgctggtgat catccgcaac cggctgaagt acgcgctgaa cgcgcgcgag | 1440 |
| ggtgagatga tcctgcgcca gggtctggtg cacgtggaca accacccgcg ccgcgacggc | 1500 |
| aagtatcccg ccggtttcat ggacgtggtc gagatcccga gacgggcga ccgcttccgc | 1560 |
| ctgatgtacg acgtcaaggg ccgcttcgcg ttggtgaacc tgtccgaggc ggaggcgcag | 1620 |
| atcaagctga tgaaggttgt gaacctgtac acggccaccg gcgcgtgcc ggtcgctgtg | 1680 |
| acgcacgacg gccaccgcat ccgctacccg gacccgcaca cctccattgg tgacaccatc | 1740 |

```
gtgtacaacg tcaaggagaa gaagtgcgtg gacctgatca agaaccgcca gggcaaggcc    1800
gtgatcgtga ccggtggcgc caaccgcggc cgcatcggcg agatcgtgaa ggtggagtgc    1860
caccccggtg cgttcaacat tgcgcacctg aaggacgcgt ccggcgccga gttcgccacc    1920
cgcgccgcga acatcttcgt gatcggcaag gacctgaaca acctgcaggt aacggtgccg    1980
aagcagcagg gcctgcgcat gaacgtgatc caggagcgcg aggagcgcct gatcgcggcg    2040
gaggcccgca gaacgcgcc ggctcgtggt gcccgcaggg cccgcaaggg agaattcggg    2100
atgaagctca acatcgcgta ccccgcaac gggacggtga agcagttcga gatctcggac    2160
gaggtgctcc gccgcgtgca gctgcaggac taccgcctcg caacgaggt ggacggcgcc    2220 atctttggta gcgagttcaa gggctacatc ttccgcctgc gcggtggctc ggacaaggat    2280
ggtttcccga tggtccctgg cgtgcttgcc tccagccgtg tgtcgctgct ggtgaagcgc    2340
ggtgcgatcg gcttcaacac cttccgcggc taccagggtg agcgccgccg caagaacgtt    2400
cgcggctgcg tgctcgcgag cgacattgcg ctggtgaacg tgaccatctc caaggtcggt    2460
gaccagccga tcgagggtgt gacggacacc acggctcccc gccgtctggg tccgaagcgc    2520
gcgagcaaga tccgcaagct cttcaacctg tcccgcaccg aagacgtgcg gaagtacgtt    2580
gttcgccgcc gcgtcgtgaa gagcggcaag aaggaccggc tgaaggcccc gaagatccag    2640
cgtctgatca cgccgagggt caaggcccgc cgtgccaaga aggccaagga cgccatcgcc    2700
aaggtgcgcg cgtctgccgc tgagcgccgt gagtacctgc gccttatcgc ctcgaaccgc    2760
cgtgcgctgc gccagcgtga ccactccaag aagcacaccc ggaaggtgca cgcccagcgc    2820
gctgaggtgg cagcattcca gaagaaggga gatatcggga tgtgcacgct ggcaaattgg    2880
gtacgcgcta tcatcaagaa acactcaaca ctcgcccaca cactcgagat gccgttcgtc    2940
aaggtcgtga agaacaaggc gtacttcaag cgcttccagg tgaagtaccg ccgtcgccgc    3000
gagggcaaga cggactacca cgcgcgccgg cagatggtgc tgcaggacaa gacgaagttc    3060
ggctcgccca gtaccgcct tgttgtgcgc atcacgaaca aggacatcat tgcgcagatc    3120
gtgcaggcga agatcgtcgg cgacgaggtg gtgatggccg cgtacgcgca cgagctgcct    3180
gcgttcggca ttgagcacgg cctgacaaac tacgctgctg cgtacgcgac tggtctgctg    3240
ctggcgcgcc gcacgctggc gaagctgggc atcgcggaca agttccaggg cgcgaaggag    3300
gcggacggct cgtactctgc tgtgcgcacg aagaaggacg acgagggcga cgacgaggag    3360 cgcttttccgt tcaaggcgat cctggacgtc ggccttgcgc gcacgacgac cggcgcccgc    3420
gtgttcggcg tgctgaaggg cgcggtggac ggcgtatgg ctgtgccgca ccgccccaac    3480
cgcttccccg gctacaacaa ggagaagagc tcgctggacg cgaaggtgca ccgcgaccgc    3540
atctttggca gcacgtggc ggactacctg aagcaggtga aggaggaggc gagctcgaac    3600
cctgacgaga agtgcgtgca gttctcgaag tacatggccg cgaaggtttt gccggagagc    3660
atcgagggca tgtacaagaa ggcgcacgcg gcgatccgcg cggacccgtc gaagtcgctg    3720
ccgaagaagg cgaagaagga gggcgtcgcg cacaagagct acaagacgaa gaagctgagc    3780
ggcgcggaga gagggccgc cgcgaaggcg aaggtcgcgg ccatccgcga gcgcctcggc    3840
aagtaa                                                               3846
```

<210> SEQ ID NO 67
<211> LENGTH: 1281
<212> TYPE: PRT
<213> ORGANISM: Artificial
<220> FEATURE:
<223> OTHER INFORMATION: Chimeric protein L3-S4-S6-L5

```
<400> SEQUENCE: 67

Met Ser His Cys Lys Phe Glu His Pro Arg His Gly His Leu Gly Phe
1               5                   10                  15

Leu Pro Arg Lys Arg Ser Arg Gln Ile Arg Gly Arg Ala Arg Ala Phe
            20                  25                  30

Pro Lys Asp Asp Ala Thr Gln Lys Pro His Leu Thr Ser Phe Met Val
        35                  40                  45

Phe Lys Ala Gly Met Thr His Ile Val Arg Asp Val Asp Arg Pro Gly
    50                  55                  60

Ser Lys Val Asn Lys Lys Glu Val Val Glu Pro Val Thr Ile Leu Glu
65                  70                  75                  80

Ala Pro Pro Met Val Ile Val Gly Ile Val Gly Tyr Arg Gln Thr Pro
                85                  90                  95

Val Gly Leu Lys Thr Ile Gly Thr Val Trp Ala His His Thr Ser Val
            100                 105                 110

Glu Phe Arg Arg Arg Tyr Tyr Lys Asn Trp Lys Gln Ser Ala Gln Leu
        115                 120                 125

Ala Phe Ser Arg Gln Lys Gln Phe Ala Asn Thr Lys Glu Gly Lys Val
    130                 135                 140

Ala Glu Ala Arg Thr Leu Asn Ala Phe Ala Lys Lys Ala Ser Val Ile
145                 150                 155                 160

Arg Val Ile Ala His Thr Gln Leu Arg Lys Leu Arg Asn His Arg Val
                165                 170                 175

Gly Val Lys Lys Ala His Val Gln Glu Ile Gln Val Asn Gly Gly Ser
            180                 185                 190

Val Ala Ala Lys Ile Ala Leu Ala Lys Ser Leu Leu Glu Lys Glu Val
        195                 200                 205

Arg Val Asp Ser Val Phe Gln Gln Ser Glu Ala Cys Asp Val Cys Ser
    210                 215                 220

Val Thr Lys Gly His Gly Thr Glu Gly Val Val Lys Arg Trp Gly Val
225                 230                 235                 240

Ala Cys Leu Pro Arg Lys Thr His Arg Gly Leu Arg Lys Val Ala Cys
                245                 250                 255

Ile Gly Ala Trp His Pro Ala Arg Val Met Tyr Thr Val Ala Arg Ala
            260                 265                 270

Gly Gln His Gly Tyr His His Arg Thr Gln Leu Asn Lys Lys Ile Tyr
        275                 280                 285

Gln Ile Gly Arg Ser Val Ala Val Glu Pro Asn Gln Ala Thr Thr Thr
    290                 295                 300

Tyr Asp Leu Thr Ala Lys Thr Ile Thr Pro Met Gly Gly Phe Val Gly
305                 310                 315                 320

Tyr Gly Thr Val Arg Asn Asp Tyr Val Met Leu Lys Gly Ser Val Ser
                325                 330                 335

Gly Pro Arg Arg Arg Val Met Thr Leu Arg Arg Pro Met Ala Pro Gln
            340                 345                 350

Thr Ser Arg Gln Leu Lys Glu Lys Ile Val Leu Lys Phe Ile Asp Thr
        355                 360                 365

Ser Ser Lys Ile Gly His Gly Arg Phe Gln Thr Lys Lys Glu Lys Asn
    370                 375                 380

Gln Trp Phe Gly Pro Leu Lys Lys Asp Arg Ile Arg Arg Glu Glu Arg
385                 390                 395                 400

Leu Arg Lys Glu Arg Ala Ala Arg Ala Val Glu Arg Lys Ala Lys Ala
                405                 410                 415
```

```
Ala Lys Lys Gly Asp Ile Gly Met Ala Lys Lys His Leu Lys Arg Leu
                420                 425                 430

Tyr Ala Pro Lys Asp Trp Met Leu Ser Lys Leu Thr Gly Val Phe Ala
                435                 440                 445

Pro Arg Pro Arg Pro Gly Pro His Lys Leu Arg Glu Cys Leu Pro Leu
            450                 455                 460

Leu Val Ile Ile Arg Asn Arg Leu Lys Tyr Ala Leu Asn Ala Arg Glu
465                 470                 475                 480

Gly Glu Met Ile Leu Arg Gln Gly Leu Val His Val Asp Asn His Pro
                485                 490                 495

Arg Arg Asp Gly Lys Tyr Pro Ala Gly Phe Met Asp Val Val Glu Ile
            500                 505                 510

Pro Lys Thr Gly Asp Arg Phe Arg Leu Met Tyr Asp Val Lys Gly Arg
            515                 520                 525

Phe Ala Leu Val Asn Leu Ser Glu Ala Glu Ala Gln Ile Lys Leu Met
            530                 535                 540

Lys Val Val Asn Leu Tyr Thr Ala Thr Gly Arg Val Pro Val Ala Val
545                 550                 555                 560

Thr His Asp Gly His Arg Ile Arg Tyr Pro Asp Pro His Thr Ser Ile
                565                 570                 575

Gly Asp Thr Ile Val Tyr Asn Val Lys Glu Lys Cys Val Asp Leu
            580                 585                 590

Ile Lys Asn Arg Gln Gly Lys Ala Val Ile Val Thr Gly Gly Ala Asn
            595                 600                 605

Arg Gly Arg Ile Gly Glu Ile Val Lys Val Glu Cys His Pro Gly Ala
            610                 615                 620

Phe Asn Ile Ala His Leu Lys Asp Ala Ser Ala Glu Phe Ala Thr
625                 630                 635                 640

Arg Ala Ala Asn Ile Phe Val Ile Gly Lys Asp Leu Asn Asn Leu Gln
                645                 650                 655

Val Thr Val Pro Lys Gln Gln Gly Leu Arg Met Asn Val Ile Gln Glu
                660                 665                 670

Arg Glu Glu Arg Leu Ile Ala Ala Glu Ala Arg Lys Asn Ala Pro Ala
            675                 680                 685

Arg Gly Ala Arg Arg Ala Arg Lys Gly Glu Phe Gly Met Lys Leu Asn
            690                 695                 700

Ile Ala Tyr Pro Arg Asn Gly Thr Val Lys Gln Phe Glu Ile Ser Asp
705                 710                 715                 720

Glu Val Leu Arg Arg Val Gln Leu Gln Asp Tyr Arg Leu Gly Asn Glu
                725                 730                 735

Val Asp Gly Ala Ile Phe Gly Ser Glu Phe Lys Gly Tyr Ile Phe Arg
            740                 745                 750

Leu Arg Gly Gly Ser Asp Lys Asp Gly Phe Pro Met Val Pro Gly Val
            755                 760                 765

Leu Ala Ser Ser Arg Val Ser Leu Leu Val Lys Arg Gly Ala Ile Gly
            770                 775                 780

Phe Asn Thr Phe Arg Gly Tyr Gln Gly Glu Arg Arg Arg Lys Asn Val
785                 790                 795                 800

Arg Gly Cys Val Leu Ala Ser Asp Ile Ala Leu Val Asn Val Thr Ile
                805                 810                 815

Ser Lys Val Gly Asp Gln Pro Ile Glu Gly Val Thr Asp Thr Thr Ala
            820                 825                 830
```

```
Pro Arg Arg Leu Gly Pro Lys Arg Ala Ser Lys Ile Arg Lys Leu Phe
        835                 840                 845

Asn Leu Ser Arg Thr Glu Asp Val Arg Lys Tyr Val Arg Arg Arg
    850                 855                 860

Val Val Lys Ser Gly Lys Lys Asp Arg Leu Lys Ala Pro Lys Ile Gln
865                 870                 875                 880

Arg Leu Ile Thr Pro Arg Val Lys Ala Arg Arg Ala Lys Lys Ala Lys
                885                 890                 895

Asp Ala Ile Ala Lys Val Arg Ala Ser Ala Ala Glu Arg Glu Tyr
                900                 905                 910

Leu Arg Leu Ile Ala Ser Asn Arg Arg Ala Leu Arg Gln Arg Asp His
        915                 920                 925

Ser Lys Lys His Thr Arg Lys Val His Ala Gln Arg Ala Glu Val Ala
    930                 935                 940

Ala Phe Gln Lys Lys Gly Asp Ile Gly Met Cys Thr Leu Ala Asn Trp
945                 950                 955                 960

Val Arg Ala Ile Ile Lys Lys His Ser Thr Leu Ala His Thr Leu Glu
                965                 970                 975

Met Pro Phe Val Lys Val Lys Asn Lys Ala Tyr Phe Lys Arg Phe
        980                 985                 990

Gln Val Lys Tyr Arg Arg Arg Glu Gly Lys Thr Asp Tyr His Ala
        995                 1000                1005

Arg Arg Gln Met Val Leu Gln Asp Lys Thr Lys Phe Gly Ser Pro
    1010                1015                1020

Lys Tyr Arg Leu Val Val Arg Ile Thr Asn Lys Asp Ile Ile Ala
    1025                1030                1035

Gln Ile Val Gln Ala Lys Ile Val Gly Asp Glu Val Val Met Ala
    1040                1045                1050

Ala Tyr Ala His Glu Leu Pro Ala Phe Gly Ile Glu His Gly Leu
    1055                1060                1065

Thr Asn Tyr Ala Ala Ala Tyr Ala Thr Gly Leu Leu Leu Ala Arg
    1070                1075                1080

Arg Thr Leu Ala Lys Leu Gly Ile Ala Asp Lys Phe Gln Gly Ala
    1085                1090                1095

Lys Glu Ala Asp Gly Ser Tyr Ser Ala Val Arg Thr Lys Lys Asp
    1100                1105                1110

Asp Glu Gly Asp Asp Glu Glu Arg Phe Pro Phe Lys Ala Ile Leu
    1115                1120                1125

Asp Val Gly Leu Ala Arg Thr Thr Thr Gly Ala Arg Val Phe Gly
    1130                1135                1140

Val Leu Lys Gly Ala Val Asp Gly Gly Met Ala Val Pro His Arg
    1145                1150                1155

Pro Asn Arg Phe Pro Gly Tyr Asn Lys Glu Lys Ser Ser Leu Asp
    1160                1165                1170

Ala Lys Val His Arg Asp Arg Ile Phe Gly Lys His Val Ala Asp
    1175                1180                1185

Tyr Leu Lys Gln Val Lys Glu Ala Ser Ser Asn Pro Asp Glu
    1190                1195                1200

Lys Cys Val Gln Phe Ser Tyr Met Ala Ala Lys Val Leu Pro
    1205                1210                1215

Glu Ser Ile Glu Gly Met Tyr Lys Lys Ala His Ala Ala Ile Arg
    1220                1225                1230
```

```
Ala Asp Pro Ser Lys Ser Leu Pro Lys Lys Ala Lys Lys Glu Gly
    1235                1240                1245

Val Ala His Lys Ser Tyr Lys Thr Lys Lys Leu Ser Gly Ala Glu
    1250                1255                1260

Lys Arg Ala Ala Ala Lys Ala Lys Val Ala Ala Ile Arg Glu Arg
    1265                1270                1275

Leu Gly Lys
    1280

<210> SEQ ID NO 68
<211> LENGTH: 399
<212> TYPE: DNA
<213> ORGANISM: Leishmania infantum

<400> SEQUENCE: 68
atggctactc ctcgcagcgc caagaaggcc gtccgcaaga gcggctccaa gtccgcgaaa      60
tgtggtctga tcttcccggt gggccgcgtc ggcgggatga tgcgccgcgg ccagtacgct     120
cgccgcatcg gtgcctctgg cgccgtgtac ctggccgccg tgctggagta cctgacggcg     180
gagctgctgg agctgtccgt gaaggcggcc gcgcagagcg ggaagaagcg gtgccgcctg     240
aacccgcgca ccgtgatgct ggccgcgcgc cacgacgacg acatcggcac gcttctgaag     300
aacgtgacct tgtctcacag cggcgttgtg ccgaacatca gcaaggcgat ggcaaagaag     360
aagggcggca agaagggcaa ggcgacaccg agcgcgtaa                            399

<210> SEQ ID NO 69
<211> LENGTH: 336
<212> TYPE: DNA
<213> ORGANISM: Leishmania infantum

<400> SEQUENCE: 69
atggcctctt ctcgctctgc tccccgcaag gcttcccacg cgcacaagtc gcaccgcaag      60
ccgaagcgct cgtggaacgt gtacgtgggc cgctcgctga aggcgatcaa cgcccagatg     120
tcgatgtcgc accgcacgat gagcatcgtg aactcgtacg tgaacgacgt gatggagcgc     180
atctgcatgg aggccgcgtc gatcgttcgc gcgaacaaga gcgcacgtt gggtgcgcgc     240 gaggtgcaga cggcggtgcg cattgtgctg ccggcggagc tcgcgaagca cgccatggct     300
gagggcacga aggccgtgtc gagcgcgtcg gcttga                               336

<210> SEQ ID NO 70
<211> LENGTH: 390
<212> TYPE: DNA
<213> ORGANISM: Leishmania infantum

<400> SEQUENCE: 70
atgtcccgca ccaaggagac cgcccgcgcg aagcgcacca tcacgtcgaa gaagagcaag      60
aaggcgccga gcggggcgtc cggcgtgaag aggtcgcatc gccgctggcg cccgggcacc     120
tgcgcgatcc gcgagatccg caagttccag aagagtacga gctgctgat ccagtgcgcg     180 ccgttccagc gcctggtgcg aggtgtcgag cggcagaagg agggcctgcg cttccagagc     240
agcgctatca tggcgctgca ggaggcgacg gaggcgtaca ttgtgtcgct gatggcggac     300
acgaacctcg cctgcatcca cgcgaagcgc gtgacgatcc agccgaagga catccagctg     360
gcgctgcgcc tgcgcggtga cgccactag                                       390
```

```
<210> SEQ ID NO 71
<211> LENGTH: 303
<212> TYPE: DNA
<213> ORGANISM: Leishmania infantum

<400> SEQUENCE: 71
atggccaagg gcaagcgttc cactgatgcc aagggcagcc agaggcgcca gaagaaggtg      60
ctgcgcgaca acatccgcgg catcactcgc ggctgcgtcc gccgcatggc gcgccgcggt     120
ggcgtgaagc gcatctcgac cgaggtgtac gaagaggtgc gccgtgtgct gaaggcctac     180
gtggaggaca ttgtgcgctg cagcacggcc tacaccgagt acgcgcgcaa gaagaccgtg     240
acggcgtgcg atgttgtgac cgcgctgcgc aagcaaggcc acatcctgta cggctacgcg     300
taa                                                                   303

<210> SEQ ID NO 72
<211> LENGTH: 336
<212> TYPE: DNA
<213> ORGANISM: Leishmania infantum

<400> SEQUENCE: 72
atgtccacca agtacctcgc cgcgtacgct ctggcctccc tgagcaaggc gtccccgtct      60
caggcggacg tggaggctat ctgcaaggcc gtccacatcg acgtcgacca ggccacccctc    120 gcctttgtga tggagagcgt tacgggacgc gacgtggcca ccctgatcgc ggagggcgcc    180
gcgaagatga gcgcgatgcc ggcggccagc tctggtgccg ctgctggcgt cactgcttcc    240
gctgcgggtg atgcggcccc ggctgccgcc gccgcgaaga aggacgagcc cgaggaggag    300
gccgacgacg acatgggctt cggtctgttc gactaa                              336

<210> SEQ ID NO 73
<211> LENGTH: 972
<212> TYPE: DNA
<213> ORGANISM: Leishmania infantum

<400> SEQUENCE: 73
atgccgtcta tcaccactgc caagcgcgag tacgaggagc gcctcgtcga ctgcctgacc      60
aagtacagct gcgtgctgtt cgtgggcatg gacaacgtcc gctcgcagca ggtgcacgat     120
gtcggccgtg cgctgcgcgc gaaggccgag ttcatgatgg gcaagaagac gctgcagggc     180
aagatcgtgg agaagcgcgc gcaagccaag gacgcgagcc ccgaggcgaa gcacttcaac     240
gatcagtgtg aggagtacaa cctgctgagc ggcaacaccg gcctcatctt cacgaacaac     300
gctgtccagg agatcacgtc tgtgcttgac gcgcaccgcg tgaagcgcgc ggcgcgtgtc     360
ggagcgattt ccccgtgtga cgtgattgtc gctgctggca gcaccggcat ggagccgacc     420
cagacgtcct tcttccaggc gctgaacatt gcgacgaaga ttgccaaggg tatggtggag     480
atcgtgacgg agaagaaggt gctgagcgtc ggcgacaagg tggacaactc gacggcgacg     540
ctgctgcaaa agctgaacat cagcccgttc tactaccagg tgaatgtgct gtccgtgtgg     600
gaccgcggtg tgctgttcac ccgcgaggac ctgatgatga cggaggacat ggtggagaag     660
atgctgatgg aaggcctgag caacgttgcg cgatggcgc tgggtgctgg catcccgacg      720
tcttcgacga ttggcccgat gctggtggac gccttcaaga acctgctggc tgtctctgtg     780
gcgacctcgt acgagttcga ggagcacaac ggcaaggagc tgcgcgaggc cgcgatcaac     840
ggcctgctgg ccggctcttg ctcggctgct gcggagcccg ccgctgccgc gccggccgcc     900
```

| | |
|---|---|
| cctagcgccg ctgccaagga ggagccggag gagagcgacg aggacgactt cggcatgggc | 960 |
| ggtctcttct aa | 972 |